US009522945B2

(12) United States Patent
Fima et al.

(10) Patent No.: US 9,522,945 B2
(45) Date of Patent: Dec. 20, 2016

(54) LONG-ACTING OXYNTOMODULIN VARIANTS AND METHODS OF PRODUCING SAME

(71) Applicant: OPKO Biologics Ltd., Nes Ziona (IL)

(72) Inventors: Udi Eyal Eyal Fima, Beer-Sheva (IL); Oren Hershkovitz, Rishon Lezion (IL)

(73) Assignee: OPKO BIOLOGICS LTD., Nes Ziona (IL)

( * ) Notice: Subject to any disclaimer, the term of this patent is extended or adjusted under 35 U.S.C. 154(b) by 0 days.

(21) Appl. No.: 14/395,441

(22) PCT Filed: Apr. 17, 2013

(86) PCT No.: PCT/IL2013/050332
§ 371 (c)(1),
(2) Date: Oct. 17, 2014

(87) PCT Pub. No.: WO2013/157002
PCT Pub. Date: Oct. 24, 2013

(65) Prior Publication Data

US 2015/0072924 A1 Mar. 12, 2015

Related U.S. Application Data

(60) Provisional application No. 61/635,483, filed on Apr. 19, 2012.

(51) Int. Cl.

| | |
|---|---|
| ***A61K 38/24*** | (2006.01) |
| ***C07K 14/575*** | (2006.01) |
| ***A61K 38/26*** | (2006.01) |
| ***A61K 9/00*** | (2006.01) |
| ***C07K 14/59*** | (2006.01) |
| *A61K 38/00* | (2006.01) |

(52) U.S. Cl.
CPC ........... *C07K 14/575* (2013.01); *A61K 9/0019* (2013.01); *A61K 38/24* (2013.01); *A61K 38/26* (2013.01); *C07K 14/59* (2013.01); *A61K 38/00* (2013.01); *C07K 2319/75* (2013.01)

(58) Field of Classification Search
None
See application file for complete search history.

(56) References Cited

U.S. PATENT DOCUMENTS

| | | | |
|---|---|---|---|
| 3,791,932 | A | 2/1974 | Schuurs et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,400,316 | A | 8/1983 | Katsuragi et al. |
| 4,666,828 | A | 5/1987 | Gusella |
| 4,683,202 | A | 7/1987 | Mullis |
| 4,801,531 | A | 1/1989 | Frossard |
| 4,853,332 | A | 8/1989 | Mark et al. |
| 4,873,316 | A | 10/1989 | Meade et al. |
| 4,879,219 | A | 11/1989 | Wands et al. |
| 4,880,634 | A | 11/1989 | Speiser |
| 4,911,691 | A | 3/1990 | Aniuk et al. |
| 5,011,771 | A | 4/1991 | Bellet et al. |
| 5,118,666 | A | 6/1992 | Habener |
| 5,177,193 | A | 1/1993 | Boime et al. |
| 5,192,659 | A | 3/1993 | Simons |
| 5,272,057 | A | 12/1993 | Smulson et al. |
| 5,281,521 | A | 1/1994 | Trojanowski et al. |
| 5,338,835 | A | 8/1994 | Boime |
| 5,405,945 | A | 4/1995 | Boime et al. |
| 5,464,764 | A | 11/1995 | Capecchi et al. |
| 5,487,992 | A | 1/1996 | Capecchi et al. |
| 5,585,345 | A | 12/1996 | Boime |
| 5,597,797 | A | 1/1997 | Clark |

(Continued)

FOREIGN PATENT DOCUMENTS

| | | |
|---|---|---|
| EP | 0264166 | 8/1996 |
| EP | 2532674 | 12/2012 |

(Continued)

OTHER PUBLICATIONS

Morgan et al., "The amino acid sequence of human chorionic gonadotropin: the α subunit and β subunit," J. Biol. Chem. 250:5247-5258 (1975).*

Bouloux et al., "First human exposure to FSH-CTP in hypogonadotrophic hypogonadal males," Hum. Reprod. Aug. 2001:16(8): 1592-7.*

Anson et al. "The gene structure of human anti-haemophilic factor DC", The EMBO Ioumal (1984)3(5):1053-1060.

Askoy et al., "A study of the intracellular and secreted forms of the MUC2 mucin from the PC/AA intestinal cell line." Glycobiology 9.7: 739-746 (1999).

Beeley, Glycoprotein and proteoglycan techniques. Elsevier: 69-72 (1985).

(Continued)

*Primary Examiner* — Julie Ha
*Assistant Examiner* — Kristina M Hellman
(74) *Attorney, Agent, or Firm* — Mark Cohen; Pearl Cohen Zedek Latzer Baratz LLP

(57) ABSTRACT

This invention is directed to a chorionic gonadotrophin carboxy terminal peptide (CTP) modified dual GLP-1/glucagon receptor agonist, and methods of producing and using the same. In one embodiment, the present invention provides a CTP-modified polypeptide comprising a dual GLP-1/glucagon receptor agonist and at least one chorionic gonadotrophin carboxy terminal peptide (CTP) attached to the amino terminus or carboxy terminus of the agonist.

33 Claims, 10 Drawing Sheets

(56) References Cited

U.S. PATENT DOCUMENTS

| | | | |
|---|---|---|---|
| 5,643,575 | A | 7/1997 | Martinez et al. |
| 5,681,567 | A | 10/1997 | Martinez et al. |
| 5,705,478 | A | 1/1998 | Boime |
| 5,712,122 | A | 1/1998 | Boime et al. |
| 5,759,818 | A | 6/1998 | Boime |
| 5,792,460 | A | 8/1998 | Bomie |
| 5,919,455 | A | 7/1999 | Greenwald et al. |
| 5,929,028 | A | 7/1999 | Skrabanja et al. |
| 5,932,447 | A | 8/1999 | Siegall |
| 5,935,924 | A | 8/1999 | Bunting et al. |
| 5,958,737 | A | 9/1999 | Boime et al. |
| 6,028,177 | A | 2/2000 | Boime |
| 6,083,725 | A | 7/2000 | Selden et al. |
| 6,103,501 | A | 8/2000 | Boime et al. |
| 6,113,906 | A | 9/2000 | Greenwald et al. |
| 6,225,449 | B1 | 5/2001 | Boime |
| 6,238,890 | B1 | 5/2001 | Boime |
| 6,242,580 | B1 | 6/2001 | Boime et al. |
| 6,306,654 | B1 | 10/2001 | Boime et al. |
| 6,310,183 | B1 | 10/2001 | Johannessen et al. |
| 6,340,742 | B1 | 1/2002 | Burg et al. |
| 6,514,729 | B1 | 2/2003 | Bentzien |
| 6,897,039 | B2 | 5/2005 | Graversen et al. |
| 7,081,446 | B2 | 7/2006 | Lustbader |
| 7,091,326 | B2 | 8/2006 | Lee et al. |
| 7,094,566 | B2 | 8/2006 | Medlock et al. |
| 7,141,547 | B2 | 11/2006 | Rosen et al. |
| 7,202,215 | B2 | 4/2007 | Lustbader |
| 7,217,689 | B1 | 5/2007 | Elliott et al. |
| 7,371,372 | B2 | 5/2008 | Chaturvedi et al. |
| 7,371,373 | B2 | 5/2008 | Shirley et al. |
| 7,425,539 | B2 | 9/2008 | Donovan et al. |
| 7,442,684 | B2 | 10/2008 | Lustbader et al. |
| 7,459,429 | B2 | 12/2008 | Klima et al. |
| 7,459,435 | B2 | 12/2008 | Lehmann et al. |
| 7,459,436 | B2 | 12/2008 | Lehmann et al. |
| 7,553,940 | B2 | 6/2009 | Fares et al. |
| 7,553,941 | B2 | 6/2009 | Fares et al. |
| 7,585,837 | B2 | 9/2009 | Shechter et al. |
| 7,649,084 | B2 | 1/2010 | Ferguson |
| 7,666,835 | B2 | 2/2010 | Bloom et al. |
| 7,795,210 | B2 | 9/2010 | Defrees |
| 8,008,454 | B2 | 8/2011 | Lee et al. |
| 8,048,846 | B2 | 11/2011 | Chahal et al. |
| 8,048,848 | B2 | 11/2011 | Fares et al. |
| 8,048,849 | B2 | 11/2011 | Fares et al. |
| 8,063,015 | B2 | 11/2011 | Defrees et al. |
| 8,097,435 | B2 | 1/2012 | Fares et al. |
| 8,110,376 | B2 | 2/2012 | Fares et al. |
| 8,114,836 | B2 | 2/2012 | Fares et al. |
| 8,129,330 | B2 | 3/2012 | Martinez et al. |
| 8,426,166 | B2 | 4/2013 | Fares et al. |
| 8,450,269 | B2 | 5/2013 | Fares et al. |
| 8,465,958 | B2 | 6/2013 | Lopez De Leon et al. |
| 2001/0007757 | A1 | 7/2001 | Boime et al. |
| 2001/0028895 | A1 | 10/2001 | Bisgaier et al. |
| 2002/0127652 | A1 | 9/2002 | Schambye et al. |
| 2002/0160944 | A1 | 10/2002 | Boime et al. |
| 2003/0113871 | A1 | 6/2003 | Lee et al. |
| 2003/0143694 | A1 | 7/2003 | Lustbader |
| 2003/0216313 | A1 | 11/2003 | Lustbader et al. |
| 2004/0009902 | A1 | 1/2004 | Boime et al. |
| 2004/0018240 | A1 | 1/2004 | Ohmachi et al. |
| 2004/0053370 | A1 | 3/2004 | Glaesner et al. |
| 2004/0057996 | A1 | 3/2004 | Takada et al. |
| 2004/0115774 | A1 | 6/2004 | Kochendoerfer |
| 2005/0234221 | A1 | 10/2005 | Medlock et al. |
| 2006/0073571 | A1 | 4/2006 | Saxena et al. |
| 2006/0088595 | A1 | 4/2006 | Asakawa et al. |
| 2006/0160177 | A1 | 7/2006 | Okkels et al. |
| 2006/0171920 | A1 | 8/2006 | Shechter et al. |
| 2007/0184530 | A1 | 8/2007 | Fares et al. |
| 2007/0190610 | A1 | 8/2007 | Fares et al. |
| 2007/0190611 | A1 | 8/2007 | Fares et al. |
| 2007/0298041 | A1 | 12/2007 | Tomlinson |
| 2008/0064856 | A1 | 3/2008 | Warne et al. |
| 2009/0053185 | A1 | 2/2009 | Schulte et al. |
| 2009/0087411 | A1 | 4/2009 | Fares et al. |
| 2009/0130060 | A1 | 5/2009 | Weimer et al. |
| 2009/0221037 | A1 | 9/2009 | Lee et al. |
| 2009/0221485 | A1 | 9/2009 | James |
| 2009/0270489 | A1 | 10/2009 | Fares et al. |
| 2009/0275084 | A1 | 11/2009 | Fares et al. |
| 2009/0286733 | A1 | 11/2009 | Fares et al. |
| 2009/0312254 | A1 | 12/2009 | Fares et al. |
| 2010/0081614 | A1 | 4/2010 | Fares et al. |
| 2010/0144617 | A1 | 6/2010 | Sinha Roy et al. |
| 2010/0310546 | A1 | 12/2010 | Schuster et al. |
| 2010/0317585 | A1 | 12/2010 | Fima et al. |
| 2011/0004172 | A1 | 1/2011 | Eckstein et al. |
| 2011/0034374 | A1 | 2/2011 | Bloom et al. |
| 2011/0065660 | A1 | 3/2011 | Baron et al. |
| 2011/0152182 | A1 | 6/2011 | Alsina-Fernandez et al. |
| 2011/0166063 | A1 | 7/2011 | Bossard et al. |
| 2011/0223151 | A1 | 9/2011 | Behrens et al. |
| 2011/0286967 | A1 | 11/2011 | Fares et al. |
| 2012/0004286 | A1 | 1/2012 | Fares et al. |
| 2012/0015437 | A1 | 1/2012 | Fares et al. |
| 2012/0035101 | A1 | 2/2012 | Fares et al. |
| 2012/0114651 | A1 | 5/2012 | De Wildt et al. |
| 2012/0208759 | A1 | 8/2012 | Fima et al. |
| 2013/0184207 | A1 | 7/2013 | Fares et al. |
| 2013/0243747 | A1 | 9/2013 | Fima et al. |
| 2014/0113860 | A1 | 4/2014 | Fima et al. |
| 2014/0316112 | A1 | 10/2014 | Hershkovitz et al. |
| 2014/0371144 | A1 | 12/2014 | Fares et al. |
| 2015/0038413 | A1 | 2/2015 | Fares et al. |
| 2015/0079063 | A1 | 3/2015 | Fima et al. |
| 2015/0158926 | A1 | 6/2015 | Fares et al. |

FOREIGN PATENT DOCUMENTS

| | | | |
|---|---|---|---|
| EP | 2420251 | | 3/2013 |
| WO | WO8910756 | | 11/1989 |
| WO | WO 93/06844 | A1 | 4/1993 |
| WO | WO9424148 | | 10/1994 |
| WO | WO0023472 | | 4/2000 |
| WO | WO 02/36169 | A2 | 5/2002 |
| WO | WO0248194 | | 6/2002 |
| WO | WO 02/085311 | A2 | 10/2002 |
| WO | WO 03/038100 | A1 | 5/2003 |
| WO | WO 03/048210 | A1 | 6/2003 |
| WO | WO2004006756 | | 1/2004 |
| WO | WO 2004/089280 | | 10/2004 |
| WO | WO2005080544 | | 9/2005 |
| WO | WO 2006/134340 | | 12/2006 |
| WO | WO2007094985 | | 8/2007 |
| WO | WO2010007622 | | 1/2010 |
| WO | WO2010097077 | | 9/2010 |
| WO | WO 2011/004361 | A2 | 1/2011 |
| WO | WO 2011/087672 | | 7/2011 |
| WO | WO 2012/011752 | | 5/2012 |
| WO | WO 2012/167251 | | 12/2012 |
| WO | WO 2013/157002 | | 10/2013 |
| WO | WO 2013/183052 | | 12/2013 |
| WO | WO 2014/080401 | A2 | 5/2014 |

OTHER PUBLICATIONS

Butler et al., "The beta-subunit of human chorionic gonadotrophin exists as a homodimer." Journal of Molecular Endocrinology 22.2: 185-192 (1999).

Cawley et al. "Developing long-acting growth hormone formulations", Clin Endocrinol (Oxf). Sep. 2013;79(3):305-9.

Chan et al. "Plasma Insulin-Like Growth Factor-I and Prostate Cancer Risk: A Prospective Study", Science vol. 279:563-566, Jan. 1998.

Chen et al., "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).

(56) References Cited

OTHER PUBLICATIONS

Chen et al., "Glycoengineering Approach to Half-Life Extension of Recombinant Biotherapeutics." Bioconjugate Chemistry 23.8: 1524-1533 (2012).
Chen et al., "Modulating antibody pharmacokinetics using hydrophilic polymers." Expert Opinion on Drug Delivery 8.9: 1221-1236 (2011).
Eschbach et al. "Correction of the Anemia of End-Stage Renal Disease with Recombinant Human Erythropoietin", N Engl J Med. Jan. 8, 1987;316(2):73-8.
Fares, "The role of O-linked and N-linked oligosaccharides on the structure-function of glycoprotein hormones: development of agonists and antagonists", Biochimica et Biophysica Acta (BBA)—General Subjects 1760.4: 560-567 (2006).
Fingel et al., "The Pharmacological Basis of Therapeutics." Ch. I p. I. (1975).
Garcia-Campayo et al., "Unmasking a new recognition signal for *O*-linked glycosylation in the chorionic gonadotropin β subunit." Molecular and Cellular Endocrinology 194.1: 63-70 (2002).
Guitton et al., "Influence of in vitro non-enzymatic glycosylation on the physicochemical parameters of type I collagen." Collagen and Related Research 4.4: 253-264 (1984).
Kanda et al. "Genetic fusion of an alpha-subunit gene to the follicle-stimulating hormone and chorionic gonadotropin-beta subunit genes: production of a bifunctional protein", Mol Endocrinol. Nov. 1999;13(11):1873-81.
Kicman et al., "Human chorionic gonadotrophin and sport." British Journal of Sports Medicine 25.2 : 73-80 (1991).
Kontermann, "Half-Life Modulating Strategies—An Introduction." Therapeutic Proteins: Strategies to Modulate Their Plasma Half-Lives : 1-21 (2012).
Kontermann, "Strategies for extended serum half-life of protein therapeutics." Current opinion in Biotechnology 22.6: 868-876 (2011).
Knudsen et al. "Small-molecule agonists for the glucagon-like peptide 1 receptor", PNAS, Jan. 16, 2007, vol. 104, No. 3, 937-942.
Larsen et al., "Accumulation of magnetic iron oxide nanoparticles coated with variably sized polyethylene glycol in murine tumors." Nanoscale 4.7: 2352-2361 (2012).
Lentz et al., "Posttranslational modification of the carboxy-terminal region of the. beta. subunit of human chorionic gonadotropin." Biochemistry 23.22: 5330-5337 (1984).
Lopez-Berestein et al. "Treatment of systemic fungal infections with liposomal amphotericin B", Arch Intern Med. Nov. 1989;149(11):2533-6.
Maheshwari et al., "Manipulation of Electrostatic and Saccharide Linker Interactions in the Design of Efficient Glycopolypeptide-Based Cholera Toxin Inhibitors." Macromolecular bioscience 10.1: 68-81 (2010).
McAlister et al. "NMR analysis of the N-terminal SRCR domain of human CD5: engineering of a glycoprotein for superior characteristics in NMR experiments." Protein Engineering 11.10: 847-853 (1998).
Murray et al. "Dose titration and patient selection increases the efficacy of GH replacement in severely GH deficient adults", Clinical Endocrinology (1999) 50, pp. 749-757.
Ogle et al. "Renal effects of growth hormone. I. Renal function and kidney growth", Pediatr. Nephrol. vol. 6:394-398, 1992.
Pedrosa et al., "Selective neoglycosylation increases the structural stability of vicilin, the 7S storage globulin from pea seeds." Archives of Biochemistry and Biophysics 382.2: 203-210 (2000).
Pierce et al., "Glycoprotein hormones: structure and function." Annual review of biochemistry 50.1: 465-495 (1981).
Polizzotti et al., "Effects of saccharide spacing and chain extension on toxin inhibition by glycopolypeptides of well-defined architecture." Macromolecules 40.20: 7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Puett et al. Structure-Function relationships of the luteinizing hormone receptor Ann. NY Acad. Sci. 1061: 41-54, 2005.
Rebois et al., "Hydrodynamic properties of the gonadotropin receptor from a murine Leydig tumor cell line are altered by desensitization." Biochemistry 26.20: 6422-6428 (1987).
Reichel, "Sarcosyl-Page: a new electrophoretic method for the separation and immunological detection of PEGylated proteins." Protein Electrophoresis. Humana Press 65-79 (2012).
Runge et al. "Different domains of the glucagon and glucagon-like peptide-1 receptors provide the critical determinants of ligand selectivity", British Journal of Pharmacology (2003) 138, 787-794.
Sugahara et al., "Characterization of the O-glycosylation sites in the chorionic gonadotropin β subunit in vivo using site-directed mutagenesis and gene transfer." Journal of Biological Chemistry 271.34: 20797-20804 (1996).
Tape et al. "Apolipoprotein A-I and apolipoprotein SAA half-lives during acute inflammation and amyloidogenesis", Biochimica et Biophysica Acta (lipid and lipid metabolism) 1043: 295-300, 1990.
Venn et al., "Biosynthesis and metabolism in vivo of intervertebral-disc proteoglycans in the mouse." Biochem. J 215: 217-225 (1983).
Wildt et al., "The humanization of N-glycosylation pathways in yeast." Nature Reviews Microbiology 3.2: 119-128 (2005).
Wilken et al., "A novel four-amino acid determinant defines conformational freedom within chorionic gonadotropin β-subunits." Biochemistry 46.14: 4417-4424 (2007).
Zheng et al., "The impact of glycosylation on monoclonal antibody conformation and stability." MAbs. vol. 3. No. 6. Landes Bioscience (Nov.-Dec. 2011).
Fares et al., "Development of a Long-acting ertyhropoietin by fusing the carboxyl-terminal peptide of human chorionic gonadotropin beta-subunit to the coding sequence of human erythropoietin," Endocrinol. 148(10):5081-5087(2007).
U.S. Appl. No. 11/700,910, filed Feb. 1, 2007, Fares et al.
U.S. Appl. No. 11/700,911, filed Feb. 1, 2007, Fares et al.
U.S. Appl. No. 11/702,156, filed Feb. 5, 2007, Fares et al.
U.S. Appl. No. 12/216,989, filed Jul. 14, 2008, Fares et al.
U.S. Appl. No. 12/401,746, filed Mar. 11, 2009, Fares et al.
U.S. Appl. No. 12/401,755, filed Mar. 11, 2009, Fares et al.
U.S. Appl. No. 12/476,916, filed Jun. 2, 2009, Fares et al.
U.S. Appl. No. 60/764,761, filed Feb. 3, 2006, Fares et al.
U.S. Appl. No. 61/224,366, filed Jul. 9, 2009, Fima et al.
Coruzzi, Gloria, et al. "Tissue-specific and light-regulated expression of a pea nuclear gene encoding the small subunit of ribulose-1, 5-bisphosphate carboxylase." The EMBO journal 3.8 (1984): 1671-1679.
Cutfield et al., "Non-compliance with growth hormone treatment in children is common and impairs linear growth." PLoS One 6.1: e16223 (2011).
Database Geneseq [Online] 18 Mar. 24, 2005; "Epogen signal peptide", XP002685292, retrieved from EBI accession No. GSP:ADS64918, Database accession No. ADW649.
Database Geneseq [Online] Apr. 7, 2005, "Human interferon beta (without signal peptide)." XP002664024 retrieved from EBI accession No. GSP: ADW02285, Database accession No. ADW02285.
Davis CG et al. "Deletion of clustered O-linked carbohydrates does not impair function of low density lipoprotein receptor in transfected fibroblasts" J Biol Chem. 261(6):2828-38, Feb. 25, 1986.
Diederichs, J. E., and R. H. Müller. "Liposome in kosmetika und arzneimitteln." Pharmazeutische Industrie 56.3 (1994): 267-275.
Diness, et al. Lund-Hansen, and U. Hedner. "Effect of recombinant human FVIIA on warfarin-induced bleeding in rats." Thrombosis research 59.6 (1990): 921-929.
Dong et al. "The prolonged half-lives of new erythropoietin derivatives via peptide addition" Biochemical Research Communications, 339(1):380-385 (Jan. 6, 2006).
Drake et al., Optimizing GH therapy in adults and children, Endocr Rev., Aug. 2001; 22(4):425-50.
Edlund, Thomas, et al. "Cell-specific expression of the rat insulin gene: evidence for role of two distinct 5'flanking elements." Science 230.4728 (1985): 912-916.

(56) References Cited

OTHER PUBLICATIONS

Ameredes et al. "Growth Hormone Improves Body Mass Recovery with Refeeding after Chronic Undernutrition-Induced Muscle Atrophy in Aging Male Rats" Journal of Nutrition. 129:2264-2270 (1999).
Amirizahdeh et al. "Expression of biologically active recombinant B-domain-deleted human VIII in mammalian cells" Journal of Science, Islamic Republic of Iran. Abstract. 16(2):103-112, (2005).
Banerji et al. "A lymphocyte-specific cellular enhancer is located downstream of the joining region in immunoglobulin heavy chain genes" Cell 33:729-740 (1983).
Barker et al. "An immunomagnetic-base method for the purification of ovarian cancer cells from patient-derived ascites" (Gynecologic Oncology 82, 57-63, 2001).
Bengtsson et al. "Treatment of adults with growth hormone (GH) deficiency with recombinant human GH" J Clin Endocrinol Metab. Feb. 1993;76(2):309-17.
Berntorp et al. "The pharmacokinetics of clotting factor therapy"; Haemophilia (2003) 9:353-359.
Bitter, Grant A., et al. "Vectors Expression and secretion vectors for yeast." Methods in enzymology 153 (1987): 516-544.
Bjorkman et al. Pharmacokinetics of Coagulation Factors Clinical Relevance for Patients with Haemophilia. Clin Pharmacokinet vol. 40 (11): 815-832 (2001).
Bohl et al. "Improvement of erythropoiesis in b-thalassemic mice by continuous erythropoietin delivery from muscle" Blood 95:2793-2798 (2000).
Boissel et al. "Erythropoietin structure-function relationships" The Journal of Biological Chemistry 268(21):15983-15993 (1993).
Booth et al. "The use of a 'universal' yeast expression vector to produce an antigenic protein of *Mycobacterium leprae*" Immunol. Lett. 19:65-70 (1988).
Brisson et al. "Expression of a bacterial gene in plants by using a viral vector" Nature, 310:511-514 (1984).
Broglie, Richard, et al. "Light-regulated expression of a pea ribulose-1, 5-bisphosphate carboxylase small subunit gene in transformed plant cells." Science 224 (1984): 838-843.
Brunetti-Pierri et al. "Bioengineered factor IX molecules with increased catalytic activity improve the therapeutic index of gene therapy vectors for hemophilia B." Human Gene Therapy 20.5: 479-485 (2009).
Buchwald et al. "Long-term, continuous intravenous heparin administration by an implantable infusion pump in ambulatory patients with recurrent venous thrombosis" Surgery 88:507-516 (1980).
Byrne, G. W., and F. H. Ruddle. "Multiplex gene regulation: a two-tiered approach to transgene regulation in transgenic mice." Proceedings of the National Academy of Sciences 86.14 (1989): 5473-5477.
Calame, Kathryn, and Suzanne Eaton. "Transcriptional controlling elements in the immunoglobulin and T cell receptor loci." Advances in Immunology 43 (1988): 235-275.
Claxton et al., "A systematic review of the associations between dose regimens and medication compliance." Clinical Therapeutics 23.8: 1296-1310 (2001).
Coleman et al., "Dosing frequency and medication adherence in chronic disease." Journal of managed care pharmacy: JMCP 18.7: 527-539 (2012).
Eldem, T., Speiser, P., and Hinkal, A. , "Optimization of spray-dried and congelated lipid micropellets and characterization of their surface morphology by scanning electron microscopy," Pharmaceutical Research, vol. 8, issue 1 pp. 47-54, 1991.
European Search Report for Application No. 07749922 dated Oct. 8, 2009.
European Search Report for European Patent Application No. 10796803.4 dated Feb. 28, 2013.
European Search Report for European Patent Application No. 12150722.2 dated Jun. 4, 2012.
European Search Report for European Patent Application No. 12179805 dated Nov. 9, 2012.
European Search Report for European Patent Application No. 12179821 dated Nov. 12, 2012.
Extended European Search Report for EP patent application No. 09797630.2, dated Dec. 5, 2011.
Fares et al. "Design of a long-acting follitropin agonist by fusing the C-terminal sequence of the chorionic gonadotropin beta subunit to the follitropin beta subunit" Proc Natl Acad Sci U S A., 89(10): 4304-4308, May 15, 1992.
Fares et al. "Designing a long-acting human growth hormone (hGH) by fusing the carboxy-terminal peptide of human chorionic gonadotropin B-subunit to the coding sequence of hGH" Endocrinology 151(9):4410-4417 (2010).
Fares et al. "Development of a Long-Acting Erythropoietin by Fusing the Carboxyl-Terminal Peptide of Human Chorionic Gonadotropin β-Subunit to the Coding Sequence of Human Erythropoietin" (2007) Endocrinology 148(10):5081-5087.
Fares et al. "Growth hormone (GH) retardation of muscle damage due to immobilization in old rats. Possible intervention with a new long-acting recombinant GH" Ann N Y Acad Sci. 786:430-43 (Jun. 15, 1996).
Fares et al., Designing a Long Acting Erythropoietin by Fusing Three Carboxyl-Terminal Peptides of Human Chorionic Gonadotropin β Subunit to the N-Terminal and C-Terminal Coding Sequence, Int. J. Cell Biol. 2011;2011:275063.
Fayad et al. "Update of the M. D. Anderson Cancer Center experience with hyper-CVAD and rituximab for the treatment of mantle cell and Burkitt-type lymphomas" Clin Lymphoma Myeloma. Dec. 2007;8 Suppl 2:S57-62.
Fingl et al., "General Principles." The Pharmacological Basis of Therapeutics (ed. Goodman, LS & Gilman, A,): 1-46 (1975).
Freshney "Culture of animal cells: A manual of basic technique" (Culture of Animal Cells, A Manual of Basic Technique, Alan R. Liss, Inc., 1983, New York, p. 4).
Fuentes-Prior et al. "Structural basis for the anticoagulant activity of the thrombin-thrombomodulin complex" Nature. Mar. 30, 2000; 404 (6777):518-25.
Furuhashi et al. Fusing the carboxy-terminal peptide of the chorionic gonadotropin (CG) b-subunit to the common α-submit: Retention of O-linked glycosylation and enhanced in vivo bioactivity of chimeric human CG: Molecular Endocrinology 9(1):54-63 (1995).
Furuhashi et al. "Processing of O-linked glycosylation in the chimera consisting of alpha-subunit and carboxyl-terminal peptide of the human chorionic gonadotropin beta-subunit is affected by dimer formation with follicle-stimulating hormone beta-subunit" Endocrine Journal 51(1):53-59 (2004).
Gao et al., "Erythropoietin gene therapy leads to autoimmune anemia in macaques" Blood 103(9):3300-3302 (2004).
Gardella, Thomas J., et al. "Expression of human parathyroid hormone-(1-84) in *Escherichia coli* as a factor X-cleavable fusion protein." Journal of Biological Chemistry 265.26 (1990): 15854-15859.
Gellerfors et al. "Characterisation of a secreted form of recombinant derived human growth hormone, expressed in *Escherichia coli* cells", J Pharm Biomed Anal 7(2):173-83 (1989).
Ghosh et al., "Activity and regulation of factor VIIa analogs with increased potency at the endothelial cell surface." Journal of Thrombosis and Haemostasis 5.2: 336-346 (2007).
Gilboa et al., "Transfer and Expression of Cloned Genes Using Retroviral Vectors", Biotechniques, vol. 4:504-512, (1986).
Goodson, J. Max. "Dental applications." Medical Applications of Controlled Release, vol. 2 (1984): 115-138.
Gurley, William B., et al. "Upstream sequences required for efficient expression of a soybean heat shock gene." Molecular and Cellular Biology 6.2 (1986): 559-565.
Hacke et al. "Intravenous thrombolysis with recombinant tissue plasminogen activator for acute hemispheric stroke. The European Cooperative Acute Stroke Study (ECASS)" JAMA. 1995;274(13):1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).

(56) References Cited

OTHER PUBLICATIONS

Heffernan et al. "Effects of oral administration of a synthetic fragment of human growth hormone on lipid metabolism" Am J Physiol Endocrinol Metab 279: E501-E507, (2000).
Houdebine, L., "The methods to generate transgenic animals and to control transgene expression" Journal of Biotechnology 98:145-160 (2002).
Huston et al. "Protein engineering of antibody binding sites: Recovery of specific activity in an anti-digoxin single-chain Fv analogue produced in *Escherichia coli*" Proc. Natl. Acad. Sci. USA vol. 85, pp. 5879-5883, Biochemistry, Aug. 1988.
International Preliminary Report on Patentability for Application No. PCT/IL09/00700 dated Jan. 27, 2011.
International Preliminary Report on Patentability for Application No. PCT/US07/02767 dated Aug. 14, 2008.
International Preliminary Report on Patentability for Application No. PCT/IL2010/000532 dated Jan. 19, 2012.
International Preliminary Report on Patentability for Application No. PCT/US07/03014 dated Apr. 2, 2009.
International Search Report and Written Opinion for PCT Application No. PCT/IL09/00700 dated Feb. 4, 2010.
International Search Report and Written Opinion for PCT Application No. PCT/IL10/00532 dated Apr. 11, 2011.
International Search Report and Written Opinion for PCT Application No. PCT/IL13/50107 dated Jul. 10, 2013.
International Search Report and Written Opinion for PCT Application No. PCT/US07/02767 dated Feb. 15, 2008.
International Search Report and Written Opinion for PCT Application No. PCT/US07/03014 dated Sep. 22, 2008.
International Search Report for PCT Application No. PCT/IL12/50288 mailed Jan. 28, 2013.
Isgaard et al. "Effects of local administration of GH and IGF-1 on longitudinal bone growth in rats" Am J Physiol. Apr. 1986;250(4 Pt 1):E367-72.
Joshi et al., Recombinant thyrotropin containing beta-subunit chimera with the human chorionic gonadotropin-beta carboxy-terminus is biologically active, with a prolonged plasma half-life: role of carbohydrate in bioactivity and metabolic clearance, Endocrinology, Sep. 1995; 136(9):3839-48.
Kelly et al. "Outcomes of patients with Burkitt lymphoma older than age 40 treated with intensive chemotherapeutic regimens." Clin Lymphoma Myeloma. Aug. 2009;9(4):307-10.
Kessler et al. "Structure and location of the O-glycosidic carbohydrate units of human chorionic gonadotropin" J Biol Chem. 25;254(16):7909-14 , Aug. 1979.
Kessler et al., "Structures of N-Glycosidic Carbohydrate Units of Human Chorionic Gonadotropin" J Biol Chem. Aug. 25, 1979;254(16):7901-8.
Kotler et al., "Effects of growth hormone on abnormal visceral adipose tissue accumulation and dyslipidemia in HIV-infected patients." JAIDS Journal of Acquired Immune Deficiency Syndromes 35.3: 239-252 (2004).
Langer, "New Methods of Drug Delivery," Science, 249:1527-1533 (1990).
Le et al., "Improved Vancomycin Dosing in Children Using Area Under the Curve Exposure." Pediatr Infect Dis J vol. 32, pp. e155-e163 (2013).
Li et al. "Bioassay of hGH .I. Weight gain of hypophysectomized rats". Abstract, Yaowu Fenxi Zazhi 15(2), 3-7 (1995).
Lippin et al. "Human erythropoietin gene therapy for patients with chronic renal failure" Blood 106(7):2280-2286 (2005).
Lo et al. "The effects of recombinant human growth hormone on body composition andglucose metabolism in HIV-infected patients with fat accumulation" J Clin Endocrinol Metab. Aug. 2001;86(8):3480-7. PubMed PMID: 11502767.
Lopez-Berestein, Gabriel, and Isaiah J. Fidler. "Treatment of systemic fungal infections with liposomal amphotericin B." Liposomes in the therapy of infectious diseases and cancer. (1989): 310-327.
Maston et al., "Chorionic gonadotropin beta subunit [*Homo sapiens*]" NCBI Accession No. AAL69705.1 (Apr. 3, 2002).
Matsumoto et al. The measurement of low levels of factor VIII or factor IX in hemophilia A and hemophilia B plasma by clot waveform analysis and thrombin generation assay. Journal of Thrombosis and Haemostasis vol. 4:377-384 (2006).
Matsuo et al. "Thrombolysis by human tissue plasminogen activator and urokinase in rabbits with experimental pulmonary embolus" Nature. Jun. 18, 1981;291(5816):590-1.
Maun et al., "Disulfide locked variants of factor VIIa with a restricted β-strand conformation have enhanced enzymatic activity." Protein Science 14.5: 1171-1180 (2005).
Meulien et al., "Increased biological activity of a recombinant factor IX variant carrying alanine at position+ 1." Protein Engineering 3.7: 629-633 (1990).
Milton et al. The Delineation of a Decapeptide Gonadotropin-releasing Sequence in the Carboxyl-terminal Extension of the Human Gonadotropin releasing Hormone Precursor. The Journal of Biological Chemistry, vol. 261/36:16990-16997 (Dec. 1986).
Muleo et al. Small doses of recombinant factor Vila in acquired deficiencies of vitamin K dependent factors. Blood Coagulation & Fibrinolysis Abstract, 10(8), 521-522 (1999).
Mutter et al. "A New Base-Labile Anchoring Group for Polymer-Supported Peptide Synthesis." Helvetica chimica acta 67.7 (1984): 2009-2016.
Mutter et al. "Evolution versus design: template-directed self-assembly of peptides to artificial proteins (TASP)." CHIMIA International Journal for Chemistry 54.10 (2000): 552-557.
NCBI GenBank Accession No. AAL69702 (Apr. 3, 2002).
Ngo et al. "Computational Complexity, Protein Structure Protein Prediction and the Levinthal Paradox" in Birkhauser the Protein Folding Problem and Tertiary Structure Prediction, pp. 433-440 and 492-495 (1994).
Oosterhof et al., Regulation of whole body energy homeostasis with growth hormone replacement therapy and endurance exercise, Physiol Genomics, Jun. 28, 2011;43(12):739-48.
Persson et al. "Recombinant coagulation factor VIIa—from molecular to clinical aspects of a versatile haemostatic agent", Thrombosis Research (2010) 125:483-489.
Persson et al., "Rational design of coagulation factor VIIa variants with substantially increased intrinsic activity." Proceedings of the National Academy of Sciences 98.24: 13583-13588 (2001).
Philips A. "The challenge of gene therapy and DNA delivery" J Pharm. Pharmacology 53:1169-1174 (2001).
Pinkert, Carl A., et al. "An albumin enhancer located 10 kb upstream functions along with its promoter to direct efficient, liver-specific expression in transgenic mice." Genes & Development 1.3 (1987): 268-276.
Reiter et al. "A multicenter study of the efficacy and safety of sustained release GH in the treatment of naive pediatric patients with GH deficiency" J Clin Endocrinol Metab. 86(10):4700-6 (Oct. 2001).
Ronzi et al. Optimisation of a freeze-drying process of high purity Factor VIII and Factor IX concentrates. Chemical Engineering and Processing. vol. 42:751-757 (2003).
Rudman et al. "Effects of human growth hormone in men over 60 years old" N Engl J Med. Jul. 5, 1990;323(1):1-6.
Russell et al. "Local injections of human or rat growth hormone or of purified human somatomedin-C stimulate unilateral tibial epiphyseal growth in hypophysectomized rats" Endocrinology. Jun. 1985;116(6):2563-7.
Sambrook, Joseph et al. "Molecular cloning: a laboratory manual." Cold Spring Harbor Laboratory Press, Cold Spring Harbor, New York 2 (2001).
Saudek, Christopher D., et al. "A preliminary trial of the programmable implantable medication system for insulin delivery." New England Journal of Medicine 321.9 (1989): 574-579.
Schein, Catherine H. "The shape of the messenger: Using protein structure information to design novel cytokine-based therapeutics" Abstract; Current Pharmaceutical Design 8(24):2113-2129 (2002).
Scheuttrumpf et al., "Factor IX variants improve gene therapy efficacy for hemophilia B." Blood 105.6: 2316-2323 (2005).
Schulte "Half-life extension through albumin fusion technologies", Thrombosis Research (2009) 124 Suppl. 2;S6-S8.

(56) References Cited

OTHER PUBLICATIONS

Sefton, Michael V. "Implantable pumps." Critical Reviews in Biomedical Engineering 14.3 (1986): 201-240.
Sheffield et al. "Effects of genetic fusion of factor IX to albumin on in vivo clearance in mice and rabbits", Blackwell Publishing Ltd, British Journal of Haematology (2004) 126:565-573.
Silverman et al. "A long-acting human growth hormone (Nutropin Depot): Efficacy and safety following two years of treatment in children with growth hormone deficiency" J Pediatr Endocrinol Metab.15 Suppl 2:715-22. (May 2002).
Smeland et al. "Treatment of Burkitt's/Burkitt-like lymphoma in adolescents and adults: a 20-year experience from the Norwegian Radium Hospital with the use of three successive regimens." Ann Oncol. Jul. 2004;15(7):1072-8.
Speiser et al. "Optimization of spray-dried and -congealed lipid micropellets and characterization of their surface morphology" Pharm. Res. 8:47-54 (1991).
Studier, F. William, et al. "Use of T7 RNA polymerase to direct expression of cloned genes." Methods in enzymology 185 (1990): 60-89.
Su et al. "Curcumin Inhibits Human Lung Cell Carcinoma Cancer Tumour Growth in a Murine Xenograft Model" (Phytother. Res. 24:189-191, 2010).
Takamatsu, Nobuhiko, et al. "Expression of bacterial chloramphenicol acetyltransferase gene in tobacco plants mediated by TMV-RNA." The EMBO Journal 6.2 (1987): 307-311.
Treat, J, Greenspan, AR, and Rahman, A. Liposome Encapsulated Doxorubicin—Preliminary Results of Phase I and Phase II Trials. in: G Lopez-Berestein, IJ Fidler (Eds.) Liposomes in the Therapy of Infectious Diseases and Cancer. Alan R. Liss, New York; 1989: 353-365.
Uenalp et al. "Factor VII deficiency associated with valproate treatment" Pediatrics International 50(3):403-405 Abstract (2008).
Weiss et al. "Noncompliance in Neurologic Patients" Current Treatment Options in Neurology 7:419-425 (2005).
Weissbach & Weissbach, 1988, Methods for Plant Molecular Biology, Academic Press, NY, Section VIII, pp. 421-463.
Wells, J.A, "Additivity of Mutational Effects in Proteins" Biochemistry 29:8509-8517 (1990).
White et al. "Mammalian Recombinant Coagulation Proteins: Structure and Function", Transfus. Sci. (1998) 19(2):177-189.
Winoto, Astar, and David Baltimore. "A novel, inducible and T cell-specific enhancer located at the 3'end of the T cell receptor alpha locus." The EMBO Journal 8.3 (1989): 729-733.
Wynne, Katie, et al. "Subcutaneous oxyntomodulin reduces body weight in overweight and obese subjects a double-blind, randomized, controlled trial." Diabetes 54.8 (2005): 2390-2395.
Yefenof & McConnell "Interferon amplifies complement activation by Burkitt's lymphoma cells" Nature. Feb. 21-27, 1985;313(6004):68.
Yin et al. "Recombinant human growth hormone replacement therapy in HIV-associated wasting and visceral adiposity". Exper. Rev. Anti-Infect. Ther. 3(5):727-736 (2005).
Zhong et al. "The N-terminal epidermal growth factor-like domain in factor IX and factor X represents an important recognition motif for binding to tissue factor" J. Biol. Chem. (2002) 277(5):3622-31.
Cohen et al. "Oxyntomodulin suppresses appetite and reduces food intake in humans", J Clin Endocrinol Metab. Oct. 2003;88(10):4696-701.
Srour et al. "Regulation of human factor IX expression using doxycycline-inducible gene expression system." Thromb Haemost 90.3 (2003): 398-405.
Anonymous "Prolor Biotech Announces Positive Results of its Obesity/Diabetes Drug Candidate in Preclinical Weight Loss Study", Apr. 17, 2012, pp. 1-2; Retrieved from the Internet: URL;http://web.archive.org/web/20120526154526/uttp://www.prolor-biotech.com/_Uploads/dbsAttachedFiles/NewsPROLORAnnouncesObesityDiabetesStudyResults.pdf.
Anonymous "Prolor Biotech Receives New U.S. Patent Allowance Covering Broad Applications of its CTP Platform for Long Acting Therapeutic Proteins", Jul. 11, 2011, pp. 1-2; Retrieved from the Internet: URL;http://web.archive.org/web/20110725053527/http://www.prolor-biotech.com/_Uploads/dbsAttachedFiles/NewsPROLORAnnouncesAllowanceOfNewCTPPlatform-PatentByUSPatentOffice.pdf.
Anonymous "Corporate Presentation—Lazard Capital Markets Healthcare Conference", Nov. 15, 2011, pp. 1-19; Retrieved from the Internet: URL:http://web.archive.org/web/20110628023057/http://www.prolor-biotech.com/_Uploads/dbsAttachedFiles/prolorInvestorsNov2011.pdf.
Anonymous "Corporate Presentation", Jun. 1, 2011, pp. 1-35; Retrieved from the Internet: URL;http://web.archive.org/web/20110628023057/http://www.prolor-biotech.com/_Uploads/dbsAttachedFiles/PROLORPresentationJune2011Investors.pdf.
Anonymous "PROLOR and Yeda enter definitive license agreement for Reversible PEGylation technology", Jan. 18, 2011, pp. 1-3; Retrieved from the Internet: URL;http://web.archive.org/web/20110123063420/http://www.news-medical.net/news/20110118/PROLOR-and-Yeda-enter-definitive-license-agreemen-for-Reversible-PEGYlation-technology.aspx.
Bouloux et al. "First human exposure to FSH-CTP in hypogonadotrophic hypogonadal males", Hum Reprod. Aug. 2001;16(8):1592-7.
Dalton et al. "Over-expression of secreted proteins from mammalian cell lines", Protein Sci. May 2014;23(5):517-25.
EP Search Report for Application No. 13778848.5, Published as No. 2838552, Dated Apr. 15, 2016.
Pocai et al. "Glucagon-Like Peptide 1/Glucagon Receptor Dual Agonism Reverses Obesity in Mice", Diabetes, vol. 58, Oct. 2009, pp. 2258-2266.
Shechter et al. "Reversible PEGylation of peptide YY3-36 prolongs its inhibition of food intake in mice", FEBS Lett. Apr. 25, 2005;579(11):2439-44.
Biller et al. "Effects of once-weekly sustained-release growth hormone: a double-blind, placebo-controlled study in adult growth hormone deficiency", J Clin Endocrinol Metab. Jun. 2011;96(6):1718-26.
Carles-Bonnet et al. "H—LYS—ArG—AsN—LYS—AsN—AsN—OH is the minimal active structure of oxyntomodulin." Peptides 17.3 (1996): 557-561.
Chihara et al. "Clinical aspect of growth hormone deficiency in adults", Nihon Naika Gakkai Zasshi. Sep. 10, 2000:89(9):2010-8; with English Abstract.
Jarrousse et al. "Oxyntomodulin (glucagon-37) and its C-terminal octapeptide inhibit gastric acid secretion", FEBS Lett. Aug. 19, 1985; 188(1): 81-4.
Nezu et al. "Treatment of idiopathic pituitary dwarfism with human growth hormone", Journal of Nara Medical Association 1989, vol. 40, No. 1, p. 16-22; with English Abstract.
Office Action for Japanese Application No. 2014-523441 dated May 24, 2016.
Tharakan et al. "Emerging therapies in the treatment of 'diabesity': beyond GLP-1" Trends Pharmacol Sci. Jan. 2011;32(1):8-15.

* cited by examiner

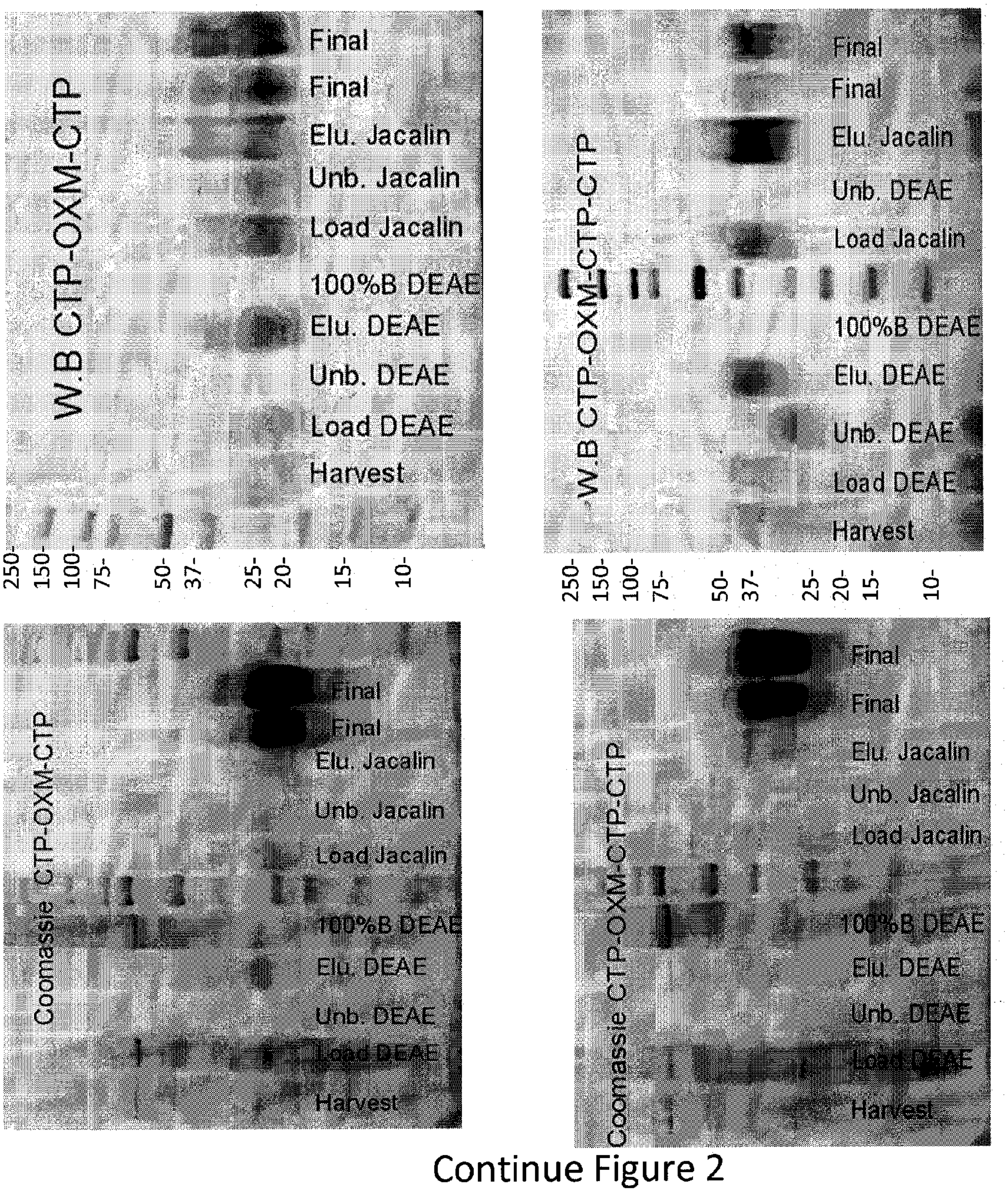
Continue Figure 2

LONG-ACTING OXYNTOMODULIN VARIANTS AND METHODS OF PRODUCING SAME

CROSS-REFERENCE TO RELATED APPLICATIONS

This application is a National Phase Application of PCT International Application No. PCT/IL2013/050332, International Filing Date Apr. 17, 2013, claiming priority of U.S. Provisional Patent Application No. 61/635,483, filed Apr. 19, 2012, which are hereby incorporated by reference.

FIELD OF INVENTION

This invention is directed to a chorionic gonadotrophin carboxy terminal peptide (CTP)-modified dual GLP-1/Glucagon receptor agonist, and methods of producing and using the same.

BACKGROUND OF THE INVENTION

Oxyntomodulin (OXM) is a 37aa peptide secreted by intestinal L cells into the bloodstream upon food ingestion and induces satiety in the brain. OXM is also a dual GPL-1/Glucagon receptor agonist. It is involved in food intake regulation and was shown to inhibit food intake and reduce body weight in both rodents and humans. However, OXM has a relatively very short half-life and repeated daily administrations of supraphysiological doses are required in order to achieve pharmacological effect in humans. Hence, there is a necessity for extending the serum half-life of OXM to make it latter more amenable for prophylactic and therapeutic purposes in animal and human subjects.

The present invention makes use of peptide-based technology for extending serum half-life of proteins and peptides, in particular, OXM. This technology is based on a natural peptide, the C-terminal peptide (CTP) of the beta chain of hCG.

SUMMARY OF THE INVENTION

In one embodiment, the present invention provides a CTP-modified polypeptide comprising a dual GLP-1/Glucagon receptor agonist and at least one chorionic gonadotrophin carboxy terminal peptide (CTP) attached to the amino terminus or carboxy terminus of said agonist.

In another embodiment, the present invention provides a method of producing a CTP-modified polypeptide comprising a dual GLP-1/Glucagon receptor agonist and at least one chorionic gonadotrophin carboxy terminal peptide (CTP) attached to the amino terminus or carboxy terminus of said agonist, the method comprising the step of attaching at least one chorionic gonadotrophin carboxy terminal peptide attached to the amino terminus or carboxy terminus of said agonist.

In one embodiment, the present invention provides a method of extending the biological half life of a dual GLP-1/Glucagon receptor agonist, comprising the step of attaching at least one chorionic gonadotrophin carboxy terminal peptides to an amino or a carboxy terminus of said agonist, thereby improving the biological half life of said agonist.

In another embodiment, the present invention provides a method of improving the area under the curve (AUC) of a dual GLP-1/Glucagon receptor agonist, comprising the step of attaching at least one chorionic gonadotrophin carboxy terminal peptides to a carboxy terminus of said agonist, thereby improving the area under the curve (AUC) of said agonist.

In one embodiment, the present invention provides a method of reducing the dosing frequency of a GLP-1/Glucagon receptor agonist, comprising the step of attaching at least one chorionic gonadotrophin carboxy terminal peptides to an amino or a carboxy terminus of said agonist, thereby reducing the dosing frequency of said agonist.

In another embodiment, the present invention provides a use of a CTP-modified polypeptide comprising a dual GLP-1/Glucagon receptor agonist and at least one chorionic gonadotrophin carboxy terminal peptide (CTP) attached to the amino terminus or caboxy terminus of said agonist for inducing glucose tolerance in a subject.

In one embodiment, the present invention provides a use of a CTP-modified polypeptide comprising a GLP-1/Glucagon receptor agonist and at least one chorionic gonadotrophin carboxy terminal peptide (CTP) attached to the amino terminus or carboxy terminus of said agonist for preventing undesired weight gain by a subject. In another embodiment, the risk of gaining weight gain is due to a psychological condition, or due to a genetic predisposposition to gain weight by the subject. In another embodiment, the psychological condition is depression, anxiety or post-traumatic stress disorder (PTSD).

In another embodiment, the present invention provides a use of a composition comprising CTP-modified polypeptide comprising a GLP-1/Glucagon receptor agonist and at least one chorionic gonadotrophin carboxy terminal peptide (CTP) attached to the amino terminus or carboxy terminus of said agonist for preventing, reducing or suppressing food intake in a subject.

In one embodiment, the present invention provides a use of a CTP-modified polypeptide comprising a GLP-1/Glucagon receptor agonist and at least one chorionic gonadotrophin carboxy terminal peptide attached to the amino terminus or carboxy terminus of said agonist for treating obesity in a subject.

In another embodiment, the present invention provides a use of a CTP-modified polypeptide comprising a GLP-1/Glucagon receptor agonist and at least one chorionic gonadotrophin carboxy terminal peptide attached to the amino terminus or carboxy terminus of said agonist for treating type II diabetes in a subject.

In one embodiment, the present invention provides a use of a CTP-modified polypeptide comprising a GLP-1/Glucagon receptor agonist and at least one chorionic gonadotrophin carboxy terminal peptide attached to the amino terminus or carboxy terminus of said agonist for treating a metabolic disorder in a subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Figure 1A:
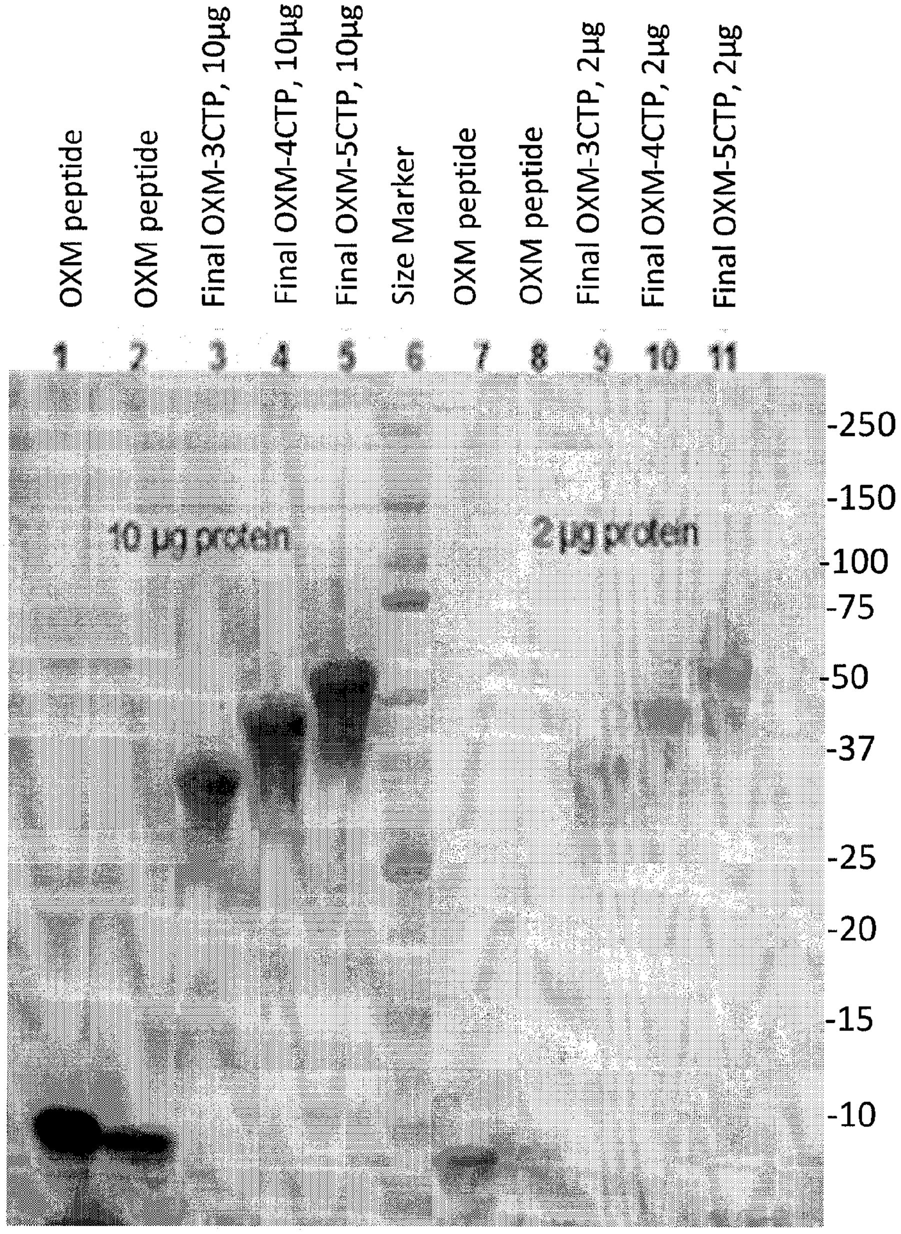
FIG. 1 shows PAGE and Western Blot (WB) analysis of purified OXM-CTP variants: OXM-CTP-CTP-CTP, OXM-CTP 4×, OXM-CTP 5×. A. Coomassie staining of OXM samples and OXM-CTP variants (10 and 2 μg protein/lane). B. WB analysis of OXM-CTP variants using anti OXM.

In one embodiment, provided herein is a CTP-modified polypeptide comprising a dual GLP-1/Glucagon receptor agonist and at least one chorionic gonadotrophin carboxy terminal peptide (CTP) attached to the amino terminus or carboxy terminus of said agonist.

In another embodiment, the agonist is a protein, a polypeptide, or a peptide. In another embodiment, the peptide is an oxyntomodulin.

In another embodiment, the CTP-modified polypeptide comprises a peptide that comprises fewer than 50 amino acids and at least one chorionic gonadotrophin carboxy terminal peptide, attached to an amino or a carboxy terminus of the peptide. In another embodiment, the peptide is oxyntomodulin (OXM).

Oxyntomodulin peptide is useful for the treatment of metabolic disorders such as diabetes and obesity. However, due to the short half-life of the peptide and its low stability in-vivo, repeated daily administrations of supraphysiological doses are required in order to achieve pharmacological effect in humans. As demonstrated hereinbelow (see Examples), all OXM-CTP variants of the invention demonstrated superior pharmacokinetic profile in rats as compared to native OXM, with a substantial increase in the exposure and elongated half-life. Surprisingly, the OXM-CTP-CTP variant demonstrated superior PK parameters as compared to the CTP-OXM-CTP-CTP variant which is fused to 3 copies of CTP, one in the N-terminus and two in tandem in the C-terminus.

Fusion of 2 and 3 CTPs to the C-terminus of OXM resulted in similar fold of increase compared to the native peptide half life (21.6 and 21 respectively), following SC administration (see Example 3 herein). Therefore, it was expected that fusion of four and five CTP to the C-terminus of OXM would not significantly elongate the half life above 20-fold. However, a surprisingly marked increase in OXM half life (i.e. 50-fold) was demonstrated for the OXM-4CTP variants and the OXM-5CTP variant with 30-fold increase in the exposure as reflected by the area under the curve (AUC) parameter (see Example 3 herein).

Hence, in one embodiment, provided herein is a CTP-modified polypeptide comprising an oxyntomodulin (OXM) peptide and at least one chorionic gonadotrophin carboxy terminal peptide (CTP) attached to the amino terminus or carboxy terminus of the oxyntomodulin peptide.

In one embodiment, a CTP-modified OXM as described herein comprises a full length OXM or an active fragment thereof connected via a peptide bond on its amino or carboxy terminus to at least one CTP unit with no CTPs on its amino terminus. In another embodiment, a CTP-modified OXM as described herein comprises a full length OXM or an active fragment thereof connected via a peptide bond on its carboxy terminus to at least one CTP unit with no CTPs on its amino terminus. In another embodiment, a CTP-modified OXM as described herein comprises a full length OXM or an active fragment thereof connected via a peptide bond on its amino terminus to at least one CTP unit with no CTPs on its carboxy terminus. In another embodiment, the present invention provides a nucleic acid molecule encoding an engineered OXM as described herein above, which in one embodiment, comprises at least one CTP attached to its carboxy terminus or its amino terminus.

In another embodiment, the CTP sequence comprises: DPRFQDSSSSKAPPPSLPSPSRLPGPSDTPIL (SEQ ID NO: 1). In another embodiment, the CTP sequence comprises: SSSSKAPPPSLPSPSRLPGPSDTPILPQ (SEQ ID NO: 2). In another embodiment, the CTP sequence comprises an amino acid sequence selected from the sequences set forth in SEQ ID NO: 1 and SEQ ID NO: 2.

In one embodiment, the carboxy terminal peptide (CTP) peptide of the present invention comprises the amino acid sequence from amino acid 112 to position 145 of human chorionic gonadotrophin. In another embodiment, the CTP sequence of the present invention comprises the amino acid sequence from amino acid 118 to position 145 of human chorionic gonadotropin, as set forth in SEQ ID NO: 2. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

Thus, in one embodiment, the CTP sequence of the present invention comprises the amino acid sequence from amino acid 112 to position 145 of human chorionic gonadotropin, as set forth in SEQ ID NO: 2. In another embodiment, the CTP sequence of the present invention comprises the amino acid sequence from amino acid 113 to position 145 of human chorionic gonadotropin, as set forth in SEQ ID NO: 2. In another embodiment, the CTP sequence of the present invention comprises the amino acid sequence from amino acid 114 to position 145 of human chorionic gonadotropin, as set forth in SEQ ID NO: 2. In another embodiment, the CTP sequence of the present invention comprises the amino acid sequence from amino acid 115 to position 145 of human chorionic gonadotropin, as set forth in SEQ ID NO: 2. In another embodiment, the CTP sequence of the present invention comprises the amino acid sequence from amino acid 116 to position 145 of human chorionic gonadotropin, as set forth in SEQ ID NO: 2. In another embodiment, the CTP sequence of the present invention comprises the amino acid sequence from amino acid 117 to position 145 of human chorionic gonadotropin, as set forth in SEQ ID NO: 2.

In another embodiment, the CTP sequence of the present invention comprises the amino acid sequence from amino acid 112 to position 145 of human chorionic gonadotropin, as set forth in SEQ ID NO: 1. In another embodiment, the CTP sequence of the present invention comprises the amino acid sequence from amino acid 113 to position 145 of human chorionic gonadotropin, as set forth in SEQ ID NO: 1. In another embodiment, the CTP sequence of the present invention comprises the amino acid sequence from amino acid 114 to position 145 of human chorionic gonadotropin, as set forth in SEQ ID NO: 1. In another embodiment, the CTP sequence of the present invention comprises the amino acid sequence from amino acid 115 to position 145 of human chorionic gonadotropin, as set forth in SEQ ID NO: 1. In another embodiment, the CTP sequence of the present invention comprises the amino acid sequence from amino acid 116 to position 145 of human chorionic gonadotropin, as set forth in SEQ ID NO: 1. In another embodiment, the CTP sequence of the present invention comprises the amino acid sequence from amino acid 117 to position 145 of human chorionic gonadotropin, as set forth in SEQ ID NO: 1. In another embodiment, the CTP sequence of the present invention comprises the amino acid sequence from amino acid 118 to position 145 of human chorionic gonadotropin, as set forth in SEQ ID NO: 1.

In one embodiment, the truncated CTP comprises SSSSKAPPPSLP (SEQ ID NO: 3). In another embodiment, the truncated CTP comprises the first 10 amino acids of SEQ ID NO: 3. In another embodiment, the truncated CTP comprises the first 11 amino acids of SEQ ID NO: 3.

In one embodiment, the truncated CTP comprises the first 14 amino acids of SEQ ID NO: 2. In one embodiment, the truncated CTP comprises the first 13 amino acids of SEQ ID NO: 2. In one embodiment, the truncated CTP comprises the first 12 amino acids of SEQ ID NO: 2. In one embodiment, the truncated CTP comprises the first 11 amino acids of SEQ ID NO: 2. In one embodiment, the truncated CTP comprises the first 10 amino acids of SEQ ID NO: 2. In one embodiment, the truncated CTP comprises the first 9 amino acids of SEQ ID NO: 2. In one embodiment, the truncated CTP comprises the first 8 amino acids of SEQ ID NO: 2 or SEQ ID NO: 3. In one embodiment, the truncated CTP comprises the first 7 amino acids of SEQ ID NO: 2 or SEQ ID NO: 3. In one embodiment, the truncated CTP comprises the first 6 amino acids of SEQ ID NO: 2 or SEQ ID NO: 3. In one embodiment, the truncated CTP comprises the first 5 amino acids of SEQ ID NO: 2 or SEQ ID NO: 3.

In another embodiment, the CTP peptide is a variant of chorionic gonadotrophin CTP which differs from the native CTP by 1-5 conservative amino acid substitutions as described in U.S. Pat. No. 5,712,122, which is incorporated herein by reference in its entirety. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions.

In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 85% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof. In another embodiment, the CTP peptide amino acid sequence of the present invention is at least 98% homologous to the native CTP amino acid sequence or a peptide thereof.

In another embodiment, the polynucleotide encoding the CTP peptide of the present invention is at least 70% homologous to the native human CTP DNA sequence or a peptide thereof. In another embodiment, the polynucleotide encoding the CTP peptide of the present invention is at least 80% homologous to the native human CTP DNA sequence or a peptide thereof. In another embodiment, the polynucleotide encoding the CTP peptide of the present invention is at least 85% homologous to the native human CTP DNA sequence or a peptide thereof. In another embodiment, the polynucleotide encoding the CTP peptide of the present invention is at least 90% homologous to the native CTP DNA sequence or a peptide thereof. In another embodiment, the polynucleotide encoding the CTP peptide of the present invention is at least 95% homologous to the native CTP DNA sequence or a peptide thereof. In another embodiment, the polynucleotide encoding the CTP peptide of the present invention is at least 98% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, two of the chorionic gonadotrophin CTP amino acid sequences are truncated. In another embodiment, three of the chorionic gonadotrophin CTP amino acid sequences are truncated. In another embodiment, four of the chorionic gonadotrophin CTP amino acid sequences are truncated. In another embodiment, five of the chorionic gonadotrophin CTP amino acid sequences are truncated. In another embodiment, two or more of the chorionic gonadotrophin CTP amino acid sequences are truncated. In another embodiment, all of the chorionic gonadotrophin CTP amino acid sequences are truncated.

In one embodiment, at least one CTP is attached to the agonist polypeptide via a linker. In another embodiment, at least one CTP is attached to the agonist polypeptide via a linker. In another embodiment, the linker is a peptide bond.

In one embodiment, at least one of the chorionic gonadotrophin CTP amino acid sequences is glycosylated. In another embodiment, both of the chorionic gonadotrophin CTP amino acid sequences are glycosylated. In another embodiment, two of the chorionic gonadotrophin CTP amino acid sequences are glycosylated. In another embodiment, three of the chorionic gonadotrophin CTP amino acid sequences are glycosylated. In another embodiment, four of the chorionic gonadotrophin CTP amino acid sequences are glycosylated. In another embodiment, five of the chorionic gonadotrophin CTP amino acid sequences are glycosylated. In another embodiment, two or more of the chorionic gonadotrophin CTP amino acid sequences are glycosylated. In another embodiment, all of the chorionic gonadotrophin CTP amino acid sequences are glycosylated.

In one embodiment, the CTP sequence of the present invention comprises at least one glycosylation site. In one embodiment, the CTP sequence of the present invention comprises two glycosylation sites. In one embodiment, the CTP sequence of the present invention comprises three glycosylation sites. In one embodiment, the CTP sequence of the present invention comprises four glycosylation sites. In one embodiment, one or more of the chorionic gonadotrophin CTP amino acid sequences is fully glycosylated. In another embodiment, one or more of the chorionic gonadotrophin CTP amino acid sequences is partially glycosylated. In one embodiment, partially glycosylated indicates that one of the CTP glycosylation sites is glycosylated. In another embodiment, two of the CTP glycosylation sites are glycosylated. In another embodiment, three of the CTP glycosylation sites are glycosylated.

In some embodiments, the CTP sequence modification is advantageous in permitting the usage of lower dosages. In some embodiments, the CTP sequences modification is advantageous in permitting fewer dosages. In some embodiments, the CTP sequences modification is advantageous in permitting a safe, long-acting effect.

In some embodiments, "polypeptide", "engineered oxyntomodulin", or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides comprising a oxyntomodulin even more stable while in a human or animal subject or more capable of penetrating into cells.

In some embodiments, modifications include, but are limited to C terminus modification, polypeptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH═CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and in one embodiment at several (2-3 bonds) at the same time.

In one embodiment, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids.

In one embodiment, the polypeptides of the present invention are utilized in therapeutics which requires the polypeptides comprising an oxyntomodulin to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In another embodiment, the engineered oxyntomodulin peptides of the present invention are biochemically synthesized such as by using standard solid phase techniques. In some embodiments, these biochemical methods include exclusive solid phase synthesis, partial solid phase synthesis, fragment condensation, or classical solution synthesis.

In one embodiment, recombinant protein techniques are used to generate the engineered oxyntomodulin peptides of the present invention. In some embodiments, recombinant protein techniques are used for the generation of relatively long polypeptides (e.g., longer than 18-25 amino acids). In some embodiments, recombinant protein techniques are used for the generation of large amounts of the engineered oxyntomodulin peptides of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463, which are incorporated herein by reference in their entirety.

In another embodiment, the CTP-modified polypeptide comprises a peptide that comprises fewer than 50 amino acids and at least one chorionic gonadotrophin carboxy terminal peptide, attached to an amino or a carboxy terminus of the peptide. In one embodiment, the CTP-modified polypeptide provided herein comprises a peptide that comprises fewer than 40 amino acids and at least one chorionic gonadotrophin carboxy terminal peptide, attached to an amino or a carboxy terminus of the peptide. In another embodiment, the CTP-modified polypeptide provided herein comprises a peptide that comprises fewer than 30, 20, or 10 amino acids. In one embodiment, the peptide comprising fewer than 50 amino acids is a GLP-1/Glucagon receptor agonist. In another embodiment, the peptide comprising fewer than 50 amino acids is OXM.

In another embodiment, OXM comprises the following amino acid (AA) sequence: HSQGTFTSDYSKYLDSRRAQDFVQWLMNTKRNRNNIA (SEQ ID NO: 30). In another embodiment, OXM consists of the amino acid sequence of SEQ ID NO: 30. In another embodiment, OXM comprises or consists of the amino acid sequence depicted in CAS No. 62340-29-8.

In another embodiment, OXM is human OXM or any mammal OXM. In another embodiment, OXM is also referred to as glucagon-37 or bioactive enteroglucagon. In another embodiment, OXM is a dual GLP-1/Glucagon receptor agonist. In another embodiment, the term OXM includes a biologically active fragment of OXM. In another embodiment, biologically active OXM extends from amino acid 30 to amino acid 37 of SEQ ID NO: 30. In another embodiment, biologically active OXM extends from amino acid 19 to amino acid 37 of SEQ ID NO: 30. In another embodiment, OXM of the invention corresponds to an octapeptide from which the two C-terminal amino acids are deleted. In another embodiment, OXM of the invention corresponds to any fragment of SEQ ID NO: 30 which retains OXM activity as described herein.

In one embodiment, two chorionic gonadotrophin carboxy terminal peptides are attached to oxyntomodulin, one CTP on the carboxy terminus and one CTP on the amino terminus of the oxyntomodulin peptide. In another embodiment, two chorionic gonadotrophin carboxy terminal peptides are attached to oxyntomodulin on the carboxy terminus of the oxyntomodulin peptide. In another embodiment, two chorionic gonadotrophin carboxy terminal peptides are attached to oxyntomodulin, both on the amino terminus of the oxyntomodulin peptide. In another embodiment, three chorionic gonadotrophin carboxy terminal peptides are attached to oxyntomodulin, one CTP on the amino terminus and two CTPs on the carboxy terminus of the oxyntomodulin peptide. In another embodiment, three chorionic gonadotrophin carboxy terminal peptides are attached to the carboxy terminus of the oxyntomodulin peptide. In another embodiment, four chorionic gonadotrophin carboxy terminal peptides are attached to the carboxy terminus of the oxyntomodulin peptide. In another embodiment, five chorionic gonadotrophin carboxy terminal peptides are attached to the carboxy terminus of the oxyntomodulin peptide. In another embodiment, 1-10 CTP are attached to the amino or carboxy terminus of oxyntomodulin. In another embodiment, 1-10 CTPs are attached to the amino terminus of oxyntomodulin. In another embodiment, 1-10 CTPs are attached to the carboxy terminus of oxyntomodulin.

In another embodiment, provided herein is a method of producing a CTP-modified polypeptide comprising an oxyntomodulin (OXM) peptide and at least one chorionic gonadotrophin carboxy terminal peptide (CTP) attached to the amino terminus or carboxy terminus of the oxyntomodulin peptide, the method comprising the step of attaching at least one chorionic gonadotrophin carboxy terminal peptide attached to the amino terminus or carboxy terminus of the oxyntomodulin peptide.

In one embodiment, provided herein is a method of extending the biological half life of a peptide comprising fewer than 50 amino acids, comprising the step of attaching at least one chorionic gonadotrophin carboxy terminal peptides to an amino or a carboxy terminus of the agonist, thereby improving the biological half life of the agonist.

In one embodiment, provided herein is a method of extending the biological half life of a dual GLP-1/Glucagon receptor agonist, comprising the step of attaching at least one chorionic gonadotrophin carboxy terminal peptides to an amino or a carboxy terminus of the agonist, thereby improving the biological half life of the agonist.

In another embodiment, provided herein is a method of extending the biological half life of oxyntomodulin, comprising the step of attaching at least one chorionic gonadotrophin carboxy terminal peptides to an amino or a carboxy terminus of the oxyntomodulin, thereby improving the biological half life of oxyntomodulin.

In one embodiment, provided herein is a method of improving the area under the curve (AUC) of a peptide comprising fewer than 50 amino acids, comprising the step of attaching at least one chorionic gonadotrophin carboxy terminal peptides to a carboxy terminus of the agonist, thereby improving the area under the curve (AUC) of the agonist.

In one embodiment, provided herein is a method of improving the area under the curve (AUC) of a dual GLP-1/Glucagon receptor agonist, comprising the step of attaching at least one chorionic gonadotrophin carboxy terminal peptides to a carboxy terminus of the agonist, thereby improving the area under the curve (AUC) of the agonist.

In another embodiment, provided herein is a method of improving the area under the curve (AUC) of oxyntomodulin, comprising the step of attaching at least one chorionic gonadotrophin carboxy terminal peptides to a carboxy terminus of the oxyntomodulin, thereby improving the area under the curve (AUC) of oxyntomodulin.

In one embodiment, the term oxyntomodulin further includes a homologue of a known oxyntomodulin. In one embodiment, the homologue is a functional homologue. In another embodiment, the term "functional" refers to the ability a homologue, peptide or protein provided herein has to suppress appetite. The term also refers to the ability a homologue, peptide or protein provided herein has to extend another protein's or peptide's biological half-life. In another embodiment, the biological half-life (T½) of a protein, peptide or homologue provided herein refers to the time it takes for half of the amount of the protein, peptide or homologue to be degraded or to not be present in a biological medium in a subject. In another embodiment, the biological medium is serum, cerebospinal fluid, tissue, mucosa, and the like.

In one embodiment, homology according to the present invention also encompasses deletion, insertion, or substitution variants, including an amino acid substitution, thereof and biologically active polypeptide fragments thereof. In one embodiment, the variant provided herein comprises conservative substitutions, or deletions, insertions, or substitutions that do not significantly alter the three dimensional structure of the oxyntomodulin. In another embodiment, the deletion, insertion, or substitution does not alter the function of interest of the oxyntomodulin, which in one embodiment, is binding to a particular binding partner.

In one embodiment, oxyntodulin binds to a receptor and mediates appetite suppression. In another embodiment, the receptor is a dual GLP-1/Glucagon receptor. In another embodiment, the receptor is a GLP-1 receptor. In another embodiment, the receptor is a glucagon receptor. In yet another embodiment, the receptor is any receptor known in the art to bind to oxyntomodulin.

In another embodiment, the invention includes a homologue of an oxyntomodulin. In one embodiment, the invention provides an OXM homologue, which in one embodiment, refers to a peptide homologue of the peptide of SEQ ID NO: 30.

In another embodiment, the invention includes a homologue of an oxyntomodulin having an appetite suppressing activity. In another embodiment, the invention includes a homologue of an oxyntomodulin having functional binding. In another embodiment, the invention includes homologues of an oxyntomodulin as described herein having an appetite suppression and activity. In another embodiment, the invention includes homologues of an oxyntomodulin as described herein having functional binding. In another embodiment, the invention also encompasses homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to an oxyntomodulin as determined using BlastP software of the National Center of Biotechnology Information (NCBI) using default parameters.

In one embodiment, provided herein is a pharmaceutical composition comprising the CTP-modified polypeptide provided herein.

It is to be understood that the compositions and methods of the present invention comprising the elements or steps as described herein may, in another embodiment, consist of those elements or steps, or in another embodiment, consist essentially of those elements or steps. In some embodiments, the term "comprise" refers to the inclusion of the indicated active agent, such as the CTP-modified GLP-1/Glucagon receptor agonist, as well as inclusion of other active agents, and pharmaceutically or physiologically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It is to be understood that the compositions and methods of the present invention comprising the elements or steps as described herein may, in another embodiment, consist of those elements or steps, or in another embodiment, consist essentially of those elements or steps. In some embodiments, the term "comprise" refers to the inclusion of the indicated active agent, such as the CTP-modified oxyntomodulin, as well as inclusion of other active agents, and pharmaceutically or physiologically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides a polypeptide comprising a GLP-1/Glucagon receptor agonist and two gonadotrophin carboxy terminal peptides (CTPs) attached to the carboxy terminus of the GLP-1/Glucagon receptor agonist. In another embodiment, provided herein is a polypeptide comprising a GLP-1/Glucagon receptor agonist and two to three CTPs attached to the carboxy terminus of the GLP-1/Glucagon receptor agonist. In another embodiment, provided herein is a polypeptide comprising a GLP-1/Glucagon receptor agonist and two to four CTPs attached to the carboxy terminus of the GLP-1/Glucagon receptor agonist. In another embodiment, provided herein is a polypeptide comprising a GLP-1/Glucagon receptor agonist and two to five CTPs attached to the carboxy terminus of the GLP-1/Glucagon receptor agonist. In another embodiment, provided herein is a polypeptide comprising a GLP-1/Glucagon receptor agonist and two to six CTPs attached to the carboxy terminus of the GLP-1/Glucagon receptor agonist. In another embodiment, provided herein is a polypeptide comprising a GLP-1/Glucagon receptor agonist and two to seven CTPs attached to the carboxy terminus of the GLP-1/Glucagon receptor agonist. In another embodiment, provided herein is a polypeptide comprising a GLP-1/Glucagon receptor agonist and two to eight CTPs attached to the carboxy terminus of the GLP-1/Glucagon receptor agonist. In another embodiment, provided herein is a polypeptide comprising a GLP-1/Glucagon receptor agonist and two to nine CTPs attached to the carboxy terminus of the GLP-1/Glucagon receptor agonist. In another embodiment, provided herein is a polypeptide comprising a GLP-1/Glucagon receptor agonist and two to ten CTPs attached to the carboxy terminus of the GLP-1/Glucagon receptor agonist.

In one embodiment, the present invention provides a polypeptide comprising an oxyntomodulin and two gonadotrophin carboxy terminal peptides (CTPs) attached to the carboxy terminus of the oxyntomodulin. In another embodiment, provided herein is a polypeptide comprising an oxyntomodulin and two to three CTPs attached to the carboxy terminus of the oxyntomodulin. In another embodiment, provided herein is a polypeptide comprising an oxyntomodulin and two to four CTPs attached to the carboxy terminus of the oxyntomodulin. In another embodiment, provided herein is a polypeptide comprising an oxyntomodulin and two to five CTPs attached to the carboxy terminus of the oxyntomodulin. In another embodiment, provided herein is a polypeptide comprising an oxyntomodulin and two to six CTPs attached to the carboxy terminus of the oxyntomodulin. In another embodiment, provided herein is a polypeptide comprising an oxyntomodulin and two to seven CTPs attached to the carboxy terminus of the oxyntomodulin. In another embodiment, provided herein is a polypeptide comprising an oxyntomodulin and two to eight CTPs attached to the carboxy terminus of the oxyntomodulin. In another embodiment, provided herein is a polypeptide comprising an oxyntomodulin and two to nine CTPs attached to the carboxy terminus of the oxyntomodulin. In another embodiment, provided herein is a polypeptide comprising an oxyntomodulin and two to ten CTPs attached to the carboxy terminus of the oxyntomodulin.

In one embodiment, the present invention provides a polypeptide comprising a GLP-1/Glucagon receptor agonist and three gonadotrophin carboxy terminal peptides (CTPs) attached to the carboxy terminus of the GLP-1/Glucagon receptor agonist. In another embodiment, provided herein is a polypeptide comprising a GLP-1/Glucagon receptor agonist and three to four CTPs attached to the carboxy terminus of the GLP-1/Glucagon receptor agonist. In another embodiment, provided herein is a polypeptide comprising a GLP-1/Glucagon receptor agonist and three to five CTPs attached to the carboxy terminus of the GLP-1/Glucagon receptor agonist. In another embodiment, provided herein is a polypeptide comprising a GLP-1/Glucagon receptor agonist and three to six CTPs attached to the carboxy terminus of the GLP-1/Glucagon receptor agonist. In another embodiment, provided herein is a polypeptide comprising a GLP-1/Glucagon receptor agonist and three to seven CTPs attached to the carboxy terminus of the GLP-1/Glucagon receptor agonist. In another embodiment, provided herein is a polypeptide comprising a GLP-1/Glucagon receptor agonist and three to eight CTPs attached to the carboxy terminus of the GLP-1/Glucagon receptor agonist. In another embodiment, provided herein is a polypeptide comprising a GLP-1/Glucagon receptor agonist and three to nine CTPs attached to the carboxy terminus of the GLP-1/Glucagon receptor agonist. In another embodiment, provided herein is a polypeptide comprising a GLP-1/Glucagon receptor agonist and three to ten CTPs attached to the carboxy terminus of the GLP-1/Glucagon receptor agonist.

In one embodiment, the present invention provides a polypeptide comprising an oxyntomodulin and three gonadotrophin carboxy terminal peptides (CTPs) attached to the carboxy terminus of the oxyntomodulin. In another embodiment, provided herein is a polypeptide comprising an oxyntomodulin and three to four CTPs attached to the carboxy terminus of the oxyntomodulin. In another embodiment, provided herein is a polypeptide comprising an oxyntomodulin and three to five CTPs attached to the carboxy terminus of the oxyntomodulin. In another embodiment, provided herein is a polypeptide comprising an oxyntomodulin and three to six CTPs attached to the carboxy terminus of the oxyntomodulin.

In another embodiment, provided herein is a polypeptide comprising an oxyntomodulin and three to seven CTPs attached to the carboxy terminus of the oxyntomodulin. In another embodiment, provided herein is a polypeptide comprising an oxyntomodulin and three to eight CTPs attached to the carboxy terminus of the oxyntomodulin. In another embodiment, provided herein is a polypeptide comprising an oxyntomodulin and three to nine CTPs attached to the carboxy terminus of the oxyntomodulin. In another embodiment, provided herein is a polypeptide comprising an oxyntomodulin and three to ten CTPs attached to the carboxy terminus of the oxyntomodulin.

In one embodiment, the present invention provides a polypeptide comprising a GLP-1/Glucagon receptor agonist and four gonadotrophin carboxy terminal peptides (CTPs) attached to the carboxy terminus of the GLP-1/Glucagon receptor agonist. In another embodiment, provided herein is a polypeptide comprising a GLP-1/Glucagon receptor agonist and four to five CTPs attached to the carboxy terminus of the GLP-1/Glucagon receptor agonist. In another embodiment, provided herein is a polypeptide comprising a GLP-1/Glucagon receptor agonist and four to six CTPs attached to the carboxy terminus of the GLP-1/Glucagon receptor agonist. In another embodiment, provided herein is a polypeptide comprising a GLP-1/Glucagon receptor agonist and four to seven CTPs attached to the carboxy terminus of the GLP-1/Glucagon receptor agonist. In another embodiment, provided herein is a polypeptide comprising a GLP-1/Glucagon receptor agonist and four to eight CTPs attached to the carboxy terminus of the GLP-1/Glucagon receptor agonist. In another embodiment, provided herein is a polypeptide comprising a GLP-1/Glucagon receptor agonist and four to nine CTPs attached to the carboxy terminus of the GLP-1/Glucagon receptor agonist. In another embodiment, provided herein is a polypeptide comprising a GLP-1/Glucagon receptor agonist and four to ten CTPs attached to the carboxy terminus of the GLP-1/Glucagon receptor agonist.

In one embodiment, the present invention provides a polypeptide comprising an oxyntomodulin and four gonadotrophin carboxy terminal peptides (CTPs) attached to the carboxy terminus of the oxyntomodulin. In another embodiment, provided herein is a polypeptide comprising an oxyntomodulin and four to five CTPs attached to the carboxy terminus of the oxyntomodulin. In another embodiment, provided herein is a polypeptide comprising an oxyntomodulin and four to six CTPs attached to the carboxy terminus of the oxyntomodulin. In another embodiment, provided herein is a polypeptide comprising an oxyntomodulin and four to seven CTPs attached to the carboxy terminus of the oxyntomodulin. In another embodiment, provided herein is a polypeptide comprising an oxyntomodulin and four to eight CTPs attached to the carboxy terminus of the oxyntomodulin. In another embodiment, provided herein is a polypeptide comprising an oxyntomodulin and four to nine CTPs attached to the carboxy terminus of the oxyntomodulin. In another embodiment, provided herein is a polypeptide comprising an oxyntomodulin and four to ten CTPs attached to the carboxy terminus of the oxyntomodulin.

In one embodiment, the present invention provides a polypeptide comprising a GLP-1/Glucagon receptor agonist and five gonadotrophin carboxy terminal peptides (CTPs) attached to the carboxy terminus of the GLP-1/Glucagon receptor agonist. In another embodiment, provided herein is a polypeptide comprising a GLP-1/Glucagon receptor agonist and five to six CTPs attached to the carboxy terminus of the GLP-1/Glucagon receptor agonist. In another embodiment, provided herein is a polypeptide comprising a GLP-1/Glucagon receptor agonist and five to seven CTPs attached to the carboxy terminus of the GLP-1/Glucagon receptor agonist. In another embodiment, provided herein is a polypeptide comprising a GLP-1/Glucagon receptor agonist and five to eight CTPs attached to the carboxy terminus of the GLP-1/Glucagon receptor agonist. In another embodiment, provided herein is a polypeptide comprising a GLP-1/Glucagon receptor agonist and five to nine CTPs attached to the carboxy terminus of the GLP-1/Glucagon receptor agonist. In another embodiment, provided herein is a polypeptide comprising a GLP-1/Glucagon receptor agonist and five to ten CTPs attached to the carboxy terminus of the GLP-1/Glucagon receptor agonist.

In one embodiment, the present invention provides a polypeptide comprising an oxyntomodulin and five gonadotrophin carboxy terminal peptides (CTPs) attached to the carboxy terminus of the oxyntomodulin. In another embodiment, provided herein is a polypeptide comprising an oxyntomodulin and five to six CTPs attached to the carboxy terminus of the oxyntomodulin. In another embodiment, provided herein is a polypeptide comprising an oxyntomodulin and five to seven CTPs attached to the carboxy terminus of the oxyntomodulin. In another embodiment, provided herein is a polypeptide comprising an oxyntomodulin and five to eight CTPs attached to the carboxy terminus of the oxyntomodulin. In another embodiment, provided herein is a polypeptide comprising an oxyntomodulin and five to nine CTPs attached to the carboxy terminus of the oxyntomodulin. In another embodiment, provided herein is a polypeptide comprising an oxyntomodulin and five to ten CTPs attached to the carboxy terminus of the oxyntomodulin.

In one embodiment, the present invention provides a polypeptide consisting of a GLP-1/Glucagon receptor agonist and two gonadotrophin carboxy terminal peptides (CTPs) attached to the carboxy terminus of the GLP-1/Glucagon receptor agonist. In another embodiment, provided herein is a polypeptide consisting of a GLP-1/Glucagon receptor agonist and two to three CTPs attached to the carboxy terminus of the GLP-1/Glucagon receptor agonist. In another embodiment, provided herein is a polypeptide consisting of a GLP-1/Glucagon receptor agonist and two to four CTPs attached to the carboxy terminus of the GLP-1/Glucagon receptor agonist. In another embodiment, provided herein is a polypeptide consisting of a GLP-1/Glucagon receptor agonist and two to five CTPs attached to the carboxy terminus of the GLP-1/Glucagon receptor agonist. In another embodiment, provided herein is a polypeptide consisting of a GLP-1/Glucagon receptor agonist and two to six CTPs attached to the carboxy terminus of the GLP-1/Glucagon receptor agonist. In another embodiment, provided herein is a polypeptide consisting of a GLP-1/Glucagon receptor agonist and two to seven CTPs attached to the carboxy terminus of the GLP-1/Glucagon receptor agonist. In another embodiment, provided herein is a polypeptide consisting of a GLP-1/Glucagon receptor agonist and two to eight CTPs attached to the carboxy terminus of the GLP-1/Glucagon receptor agonist. In another embodiment, provided herein is a polypeptide consisting of a GLP-1/Glucagon receptor agonist and two to nine CTPs attached to the carboxy terminus of the GLP-1/Glucagon receptor agonist. In another embodiment, provided herein is a polypeptide consisting of a GLP-1/Glucagon receptor agonist and two to ten CTPs attached to the carboxy terminus of the GLP-1/Glucagon receptor agonist.

In one embodiment, the present invention provides a polypeptide consisting of an oxyntomodulin and two gonadotrophin carboxy terminal peptides (CTPs) attached to the carboxy terminus of the oxyntomodulin. In another embodiment, provided herein is a polypeptide consisting of an oxyntomodulin and two to three CTPs attached to the carboxy terminus of the oxyntomodulin. In another embodiment, provided herein is a polypeptide consisting of an oxyntomodulin and two to four CTPs attached to the carboxy terminus of the oxyntomodulin. In another embodiment, provided herein is a polypeptide consisting of an oxyntomodulin and two to five CTPs attached to the carboxy terminus of the oxyntomodulin. In another embodiment, provided herein is a polypeptide consisting of an oxyntomodulin and two to six CTPs attached to the carboxy terminus of the oxyntomodulin. In another embodiment, provided herein is a polypeptide consisting of an oxyntomodulin and two to seven CTPs attached to the carboxy terminus of the oxyntomodulin. In another embodiment, provided herein is a polypeptide consisting of an oxyntomodulin and two to eight CTPs attached to the carboxy terminus of the oxyntomodulin. In another embodiment, provided herein is a polypeptide consisting of an oxyntomodulin and two to nine CTPs attached to the carboxy terminus of the oxyntomodulin. In another embodiment, provided herein is a polypeptide consisting of an oxyntomodulin and two to ten CTPs attached to the carboxy terminus of the oxyntomodulin.

In one embodiment, the present invention provides a polypeptide consisting of a GLP-1/Glucagon receptor agonist and three gonadotrophin carboxy terminal peptides (CTPs) attached to the carboxy terminus of the GLP-1/Glucagon receptor agonist. In another embodiment, provided herein is a polypeptide consisting of a GLP-1/Glucagon receptor agonist and three to four CTPs attached to the carboxy terminus of the GLP-1/Glucagon receptor agonist. In another embodiment, provided herein is a polypeptide consisting of a GLP-1/Glucagon receptor agonist and three to five CTPs attached to the carboxy terminus of the GLP-1/Glucagon receptor agonist. In another embodiment, provided herein is a polypeptide consisting of a GLP-1/Glucagon receptor agonist and three to six CTPs attached to the carboxy terminus of the GLP-1/Glucagon receptor agonist. In another embodiment, provided herein is a polypeptide consisting of a GLP-1/Glucagon receptor agonist and three to seven CTPs attached to the carboxy terminus of the GLP-1/Glucagon receptor agonist. In another embodiment, provided herein is a polypeptide consisting of a GLP-1/Glucagon receptor agonist and three to eight CTPs attached to the carboxy terminus of the GLP-1/Glucagon receptor agonist. In another embodiment, provided herein is a polypeptide consisting of a GLP-1/Glucagon receptor agonist and three to nine CTPs attached to the carboxy terminus of the GLP-1/Glucagon receptor agonist. In another embodiment, provided herein is a polypeptide consisting of a GLP-1/Glucagon receptor agonist and three to ten CTPs attached to the carboxy terminus of the GLP-1/Glucagon receptor agonist.

In one embodiment, the present invention provides a polypeptide consisting of an oxyntomodulin and three gonadotrophin carboxy terminal peptides (CTPs) attached to the carboxy terminus of the oxyntomodulin. In another embodiment, provided herein is a polypeptide consisting of an oxyntomodulin and three to four CTPs attached to the carboxy terminus of the oxyntomodulin. In another embodiment, provided herein is a polypeptide consisting of an oxyntomodulin and three to five CTPs attached to the carboxy terminus of the oxyntomodulin. In another embodiment, provided herein is a polypeptide consisting of an oxyntomodulin and three to six CTPs attached to the carboxy terminus of the oxyntomodulin. In another embodiment, provided herein is a polypeptide consisting of an oxyntomodulin and three to seven CTPs attached to the carboxy terminus of the oxyntomodulin. In another embodiment, provided herein is a polypeptide consisting of an oxyntomodulin and three to eight CTPs attached to the carboxy terminus of the oxyntomodulin. In another embodiment, provided herein is a polypeptide consisting of an oxyntomodulin and three to nine CTPs attached to the carboxy terminus of the oxyntomodulin. In another embodiment, provided herein is a polypeptide consisting of an oxyntomodulin and three to ten CTPs attached to the carboxy terminus of the oxyntomodulin.

In one embodiment, the present invention provides a polypeptide consisting of a GLP-1/Glucagon receptor agonist and four gonadotrophin carboxy terminal peptides (CTPs) attached to the carboxy terminus of the GLP-1/Glucagon receptor agonist. In another embodiment, provided herein is a polypeptide consisting of a GLP-1/Glucagon receptor agonist and four to five CTPs attached to the carboxy terminus of the GLP-1/Glucagon receptor agonist. In another embodiment, provided herein is a polypeptide consisting of a GLP-1/Glucagon receptor agonist and four to six CTPs attached to the carboxy terminus of the GLP-1/Glucagon receptor agonist. In another embodiment, provided herein is a polypeptide consisting of a GLP-1/Glucagon receptor agonist and four to seven CTPs attached to the carboxy terminus of the GLP-1/Glucagon receptor agonist. In another embodiment, provided herein is a polypeptide consisting of a GLP-1/Glucagon receptor agonist and four to eight CTPs attached to the carboxy terminus of the GLP-1/Glucagon receptor agonist. In another embodiment, provided herein is a polypeptide consisting of a GLP-1/Glucagon receptor agonist and four to nine CTPs attached to the carboxy terminus of the GLP-1/Glucagon receptor agonist. In another embodiment, provided herein is a polypeptide consisting of a GLP-1/Glucagon receptor agonist and four to ten CTPs attached to the carboxy terminus of the GLP-1/Glucagon receptor agonist.

In one embodiment, the present invention provides a polypeptide consisting of an oxyntomodulin and four gonadotrophin carboxy terminal peptides (CTPs) attached to the carboxy terminus of the oxyntomodulin. In another embodiment, provided herein is a polypeptide consisting of an oxyntomodulin and four to five CTPs attached to the carboxy terminus of the oxyntomodulin. In another embodiment, provided herein is a polypeptide consisting of an oxyntomodulin and four to six CTPs attached to the carboxy terminus of the oxyntomodulin. In another embodiment, provided herein is a polypeptide consisting of an oxyntomodulin and four to seven CTPs attached to the carboxy terminus of the oxyntomodulin. In another embodiment, provided herein is a polypeptide consisting of an oxyntomodulin and four to eight CTPs attached to the carboxy terminus of the oxyntomodulin. In another embodiment, provided herein is a polypeptide consisting of an oxyntomodulin and four to nine CTPs attached to the carboxy terminus of the oxyntomodulin. In another embodiment, provided herein is a polypeptide consisting of an oxyntomodulin and four to ten CTPs attached to the carboxy terminus of the oxyntomodulin.

In one embodiment, the present invention provides a polypeptide consisting of a GLP-1/Glucagon receptor agonist and five gonadotrophin carboxy terminal peptides (CTPs) attached to the carboxy terminus of the GLP-1/Glucagon receptor agonist. In another embodiment, provided herein is a polypeptide consisting of a GLP-1/Glucagon receptor agonist and five to six CTPs attached to the carboxy terminus of the GLP-1/Glucagon receptor agonist. In another embodiment, provided herein is a polypeptide consisting of a GLP-1/Glucagon receptor agonist and five to seven CTPs attached to the carboxy terminus of the GLP-1/Glucagon receptor agonist. In another embodiment, provided herein is a polypeptide consisting of a GLP-1/Glucagon receptor agonist and five to eight CTPs attached to the carboxy terminus of the GLP-1/Glucagon receptor agonist. In another embodiment, provided herein is a polypeptide consisting of a GLP-1/Glucagon receptor agonist and five to nine CTPs attached to the carboxy terminus of the GLP-1/Glucagon receptor agonist. In another embodiment, provided herein is a polypeptide consisting of a GLP-1/Glucagon receptor agonist and five to ten CTPs attached to the carboxy terminus of the GLP-1/Glucagon receptor agonist.

In one embodiment, the present invention provides a polypeptide consisting of an oxyntomodulin and five gonadotrophin carboxy terminal peptides (CTPs) attached to the carboxy terminus of the oxyntomodulin. In another embodiment, provided herein is a polypeptide consisting of an oxyntomodulin and five to six CTPs attached to the carboxy terminus of the oxyntomodulin. In another embodiment, provided herein is a polypeptide consisting of an oxyntomodulin and five to seven CTPs attached to the carboxy terminus of the oxyntomodulin. In another embodiment, provided herein is a polypeptide consisting of an oxyntomodulin and five to eight CTPs attached to the carboxy terminus of the oxyntomodulin. In another embodiment, provided herein is a polypeptide consisting of an oxyntomodulin and five to nine CTPs attached to the carboxy terminus of the oxyntomodulin. In another embodiment, provided herein is a polypeptide consisting of an oxyntomodulin and five to ten CTPs attached to the carboxy terminus of the oxyntomodulin.

In one embodiment, the present invention provides a polypeptide consisting essentially of a GLP-1/Glucagon receptor agonist and two gonadotrophin carboxy terminal peptides (CTPs) attached to the carboxy terminus of the GLP-1/Glucagon receptor agonist. In another embodiment, provided herein is a polypeptide consisting essentially of a GLP-1/Glucagon receptor agonist and two to three CTPs attached to the carboxy terminus of the GLP-1/Glucagon receptor agonist. In another embodiment, provided herein is a polypeptide consisting essentially of a GLP-1/Glucagon receptor agonist and two to four CTPs attached to the carboxy terminus of the GLP-1/Glucagon receptor agonist. In another embodiment, provided herein is a polypeptide consisting essentially of a GLP-1/Glucagon receptor agonist and two to five CTPs attached to the carboxy terminus of the GLP-1/Glucagon receptor agonist. In another embodiment, provided herein is a polypeptide consisting essentially of a GLP-1/Glucagon receptor agonist and two to six CTPs attached to the carboxy terminus of the GLP-1/Glucagon receptor agonist. In another embodiment, provided herein is a polypeptide consisting essentially of a GLP-1/Glucagon receptor agonist and two to seven CTPs attached to the carboxy terminus of the GLP-1/Glucagon receptor agonist. In another embodiment, provided herein is a polypeptide consisting essentially of a GLP-1/Glucagon receptor agonist and two to eight CTPs attached to the carboxy terminus of the GLP-1/Glucagon receptor agonist. In another embodiment, provided herein is a polypeptide consisting essentially of a GLP-1/Glucagon receptor agonist and two to nine CTPs attached to the carboxy terminus of the GLP-1/Glucagon receptor agonist. In another embodiment, provided herein is a polypeptide consisting essentially of a GLP-1/Glucagon receptor agonist and two to ten CTPs attached to the carboxy terminus of the GLP-1/Glucagon receptor agonist.

In one embodiment, the present invention provides a polypeptide consisting essentially of an oxyntomodulin and two gonadotrophin carboxy terminal peptides (CTPs) attached to the carboxy terminus of the oxyntomodulin. In another embodiment, provided herein is a polypeptide consisting essentially of an oxyntomodulin and two to three CTPs attached to the carboxy terminus of the oxyntomodulin. In another embodiment, provided herein is a polypeptide consisting essentially of an oxyntomodulin and two to four CTPs attached to the carboxy terminus of the oxyntomodulin. In another embodiment, provided herein is a polypeptide consisting essentially of an oxyntomodulin and two to five CTPs attached to the carboxy terminus of the oxyntomodulin. In another embodiment, provided herein is a polypeptide consisting essentially of an oxyntomodulin and two to six CTPs attached to the carboxy terminus of the oxyntomodulin. In another embodiment, provided herein is a polypeptide consisting essentially of an oxyntomodulin and two to seven CTPs attached to the carboxy terminus of the oxyntomodulin. In another embodiment, provided herein is a polypeptide consisting essentially of an oxyntomodulin and two to eight CTPs attached to the carboxy terminus of the oxyntomodulin. In another embodiment, provided herein is a polypeptide consisting essentially of an oxyntomodulin and two to nine CTPs attached to the carboxy terminus of the oxyntomodulin. In another embodiment, provided herein is a polypeptide consisting essentially of an oxyntomodulin and two to ten CTPs attached to the carboxy terminus of the oxyntomodulin.

In one embodiment, the present invention provides a polypeptide consisting essentially of a GLP-1/Glucagon receptor agonist and three gonadotrophin carboxy terminal peptides (CTPs) attached to the carboxy terminus of the GLP-1/Glucagon receptor agonist. In another embodiment, provided herein is a polypeptide consisting essentially of a GLP-1/Glucagon receptor agonist and three to four CTPs attached to the carboxy terminus of the GLP-1/Glucagon receptor agonist. In another embodiment, provided herein is a polypeptide consisting essentially of a GLP-1/Glucagon receptor agonist and three to five CTPs attached to the carboxy terminus of the GLP-1/Glucagon receptor agonist. In another embodiment, provided herein is a polypeptide consisting essentially of a GLP-1/Glucagon receptor agonist and three to six CTPs attached to the carboxy terminus of the GLP-1/Glucagon receptor agonist. In another embodiment, provided herein is a polypeptide consisting essentially of a GLP-1/Glucagon receptor agonist and three to seven CTPs attached to the carboxy terminus of the GLP-1/Glucagon receptor agonist. In another embodiment, provided herein is a polypeptide consisting essentially of a GLP-1/Glucagon receptor agonist and three to eight CTPs attached to the carboxy terminus of the GLP-1/Glucagon receptor agonist. In another embodiment, provided herein is a polypeptide consisting essentially of a GLP-1/Glucagon receptor agonist and three to nine CTPs attached to the carboxy terminus of the GLP-1/Glucagon receptor agonist. In another embodiment, provided herein is a polypeptide consisting essentially of a GLP-1/Glucagon receptor agonist and three to ten CTPs attached to the carboxy terminus of the GLP-1/Glucagon receptor agonist.

In one embodiment, the present invention provides a polypeptide consisting essentially of an oxyntomodulin and three gonadotrophin carboxy terminal peptides (CTPs) attached to the carboxy terminus of the oxyntomodulin. In another embodiment, provided herein is a polypeptide consisting essentially of an oxyntomodulin and three to four CTPs attached to the carboxy terminus of the oxyntomodulin. In another embodiment, provided herein is a polypeptide consisting essentially of an oxyntomodulin and three to five CTPs attached to the carboxy terminus of the oxyntomodulin. In another embodiment, provided herein is a polypeptide consisting essentially of an oxyntomodulin and three to six CTPs attached to the carboxy terminus of the oxyntomodulin. In another embodiment, provided herein is a polypeptide consisting essentially of an oxyntomodulin and three to seven CTPs attached to the carboxy terminus of the oxyntomodulin. In another embodiment, provided herein is a polypeptide consisting essentially of an oxyntomodulin and three to eight CTPs attached to the carboxy terminus of the oxyntomodulin. In another embodiment, provided herein is a polypeptide consisting essentially of an oxyntomodulin and three to nine CTPs attached to the carboxy terminus of the oxyntomodulin. In another embodiment, provided herein is a polypeptide consisting essentially of an oxyntomodulin and three to ten CTPs attached to the carboxy terminus of the oxyntomodulin.

In one embodiment, the present invention provides a polypeptide consisting essentially of a GLP-1/Glucagon receptor agonist and four gonadotrophin carboxy terminal peptides (CTPs) attached to the carboxy terminus of the GLP-1/Glucagon receptor agonist. In another embodiment, provided herein is a polypeptide consisting essentially of a GLP-1/Glucagon receptor agonist and four to five CTPs attached to the carboxy terminus of the GLP-1/Glucagon receptor agonist. In another embodiment, provided herein is a polypeptide consisting essentially of a GLP-1/Glucagon receptor agonist and four to six CTPs attached to the carboxy terminus of the GLP-1/Glucagon receptor agonist. In another embodiment, provided herein is a polypeptide consisting essentially of a GLP-1/Glucagon receptor agonist and four to seven CTPs attached to the carboxy terminus of the GLP-1/Glucagon receptor agonist. In another embodiment, provided herein is a polypeptide consisting essentially of a GLP-1/Glucagon receptor agonist and four to eight CTPs attached to the carboxy terminus of the GLP-1/Glucagon receptor agonist. In another embodiment, provided herein is a polypeptide consisting essentially of a GLP-1/Glucagon receptor agonist and four to nine CTPs attached to the carboxy terminus of the GLP-1/Glucagon receptor agonist. In another embodiment, provided herein is a polypeptide consisting essentially of a GLP-1/Glucagon receptor agonist and four to ten CTPs attached to the carboxy terminus of the GLP-1/Glucagon receptor agonist.

In one embodiment, the present invention provides a polypeptide consisting essentially of an oxyntomodulin and four gonadotrophin carboxy terminal peptides (CTPs) attached to the carboxy terminus of the oxyntomodulin. In another embodiment, provided herein is a polypeptide consisting essentially of an oxyntomodulin and four to five CTPs attached to the carboxy terminus of the oxyntomodulin. In another embodiment, provided herein is a polypeptide consisting essentially of an oxyntomodulin and four to six CTPs attached to the carboxy terminus of the oxyntomodulin. In another embodiment, provided herein is a polypeptide consisting essentially of an oxyntomodulin and four to seven CTPs attached to the carboxy terminus of the oxyntomodulin. In another embodiment, provided herein is a polypeptide consisting essentially of an oxyntomodulin and four to eight CTPs attached to the carboxy terminus of the oxyntomodulin. In another embodiment, provided herein is a polypeptide consisting essentially of an oxyntomodulin and four to nine CTPs attached to the carboxy terminus of the oxyntomodulin. In another embodiment, provided herein is a polypeptide consisting essentially of an oxyntomodulin and four to ten CTPs attached to the carboxy terminus of the oxyntomodulin.

In one embodiment, the present invention provides a polypeptide consisting essentially of a GLP-1/Glucagon receptor agonist and five gonadotrophin carboxy terminal peptides (CTPs) attached to the carboxy terminus of the GLP-1/Glucagon receptor agonist. In another embodiment, provided herein is a polypeptide consisting essentially of a GLP-1/Glucagon receptor agonist and five to six CTPs attached to the carboxy terminus of the GLP-1/Glucagon receptor agonist. In another embodiment, provided herein is a polypeptide consisting essentially of a GLP-1/Glucagon receptor agonist and five to seven CTPs attached to the carboxy terminus of the GLP-1/Glucagon receptor agonist. In another embodiment, provided herein is a polypeptide consisting essentially of a GLP-1/Glucagon receptor agonist and five to eight CTPs attached to the carboxy terminus of the GLP-1/Glucagon receptor agonist. In another embodiment, provided herein is a polypeptide consisting essentially of a GLP-1/Glucagon receptor agonist and five to nine CTPs attached to the carboxy terminus of the GLP-1/Glucagon receptor agonist. In another embodiment, provided herein is a polypeptide consisting essentially of a GLP-1/Glucagon receptor agonist and five to ten CTPs attached to the carboxy terminus of the GLP-1/Glucagon receptor agonist.

In one embodiment, the present invention provides a polypeptide consisting essentially of an oxyntomodulin and five gonadotrophin carboxy terminal peptides (CTPs) attached to the carboxy terminus of the oxyntomodulin. In another embodiment, provided herein is a polypeptide consisting essentially of an oxyntomodulin and five to six CTPs attached to the carboxy terminus of the oxyntomodulin. In another embodiment, provided herein is a polypeptide consisting essentially of an oxyntomodulin and five to seven CTPs attached to the carboxy terminus of the oxyntomodulin. In another embodiment, provided herein is a polypeptide consisting essentially of an oxyntomodulin and five to eight CTPs attached to the carboxy terminus of the oxyntomodulin. In another embodiment, provided herein is a polypeptide consisting essentially of an oxyntomodulin and five to nine CTPs attached to the carboxy terminus of the oxyntomodulin. In another embodiment, provided herein is a polypeptide consisting essentially of an oxyntomodulin and five to ten CTPs attached to the carboxy terminus of the oxyntomodulin.

In another embodiment, provided herein is a polypeptide comprising, consisting essentially of, or consisting of a GLP-1/Glucagon receptor agonist having no CTPs on its amino terminus. In another embodiment, provided herein is a polypeptide comprising, consisting essentially of, or consisting of a GLP-1/Glucagon receptor agonist lacking a CTP on its amino terminus. In another embodiment, provided herein is a polypeptide comprising, consisting essentially of, or consisting of a GLP-1/Glucagon receptor agonist having at least one CTP on its carboxy terminus and no CTPs on its amino terminus. In another embodiment, provided herein is a polypeptide comprising, consisting essentially of, or consisting of a GLP-1/Glucagon receptor agonist having the number of CTPs on its carboxy terminus as described herein and no CTPs on its amino terminus.

In another embodiment, provided herein is a polypeptide comprising, consisting essentially of, or consisting of an oxyntomodulin having no CTPs on its amino terminus. In another embodiment, provided herein is a polypeptide comprising, consisting essentially of, or consisting of an oxyntomodulin lacking a CTP on its amino terminus. In another embodiment, provided herein is a polypeptide comprising, consisting essentially of, or consisting of an oxyntomodulin having at least one CTP on its carboxy terminus and no CTPs on its amino terminus. In another embodiment, provided herein is a polypeptide comprising, consisting essentially of, or consisting of an oxyntomodulin having the number of CTPs on its carboxy terminus as described herein and no CTPs on its amino terminus.

In one embodiment, the amino acid sequence of the CTP-modified polypeptide comprises SEQ ID NO: 9, 15, 21, 23, 25, 27, or 29, further provided herein. In another embodiment, the amino acid sequence of the CTP-modified polypeptide is selected from the group consisting of: SEQ ID NO: 9, 15, 21, 23, 25, 27, or 29, further provided herein.

In another embodiment, the present invention provides a polynucleotide encoding a polypeptide as described hereinabove. In another embodiment, the polynucleotide comprises SEQ ID NO: 8, 14, 20, 22, 24, 26 or 28, further provided herein. In another embodiment, the polynucleotide is selected from the group consisting of SEQ ID NO: 98, 14, 20, 22, 24, 26 or 28, further provided herein.

In one embodiment, provided herein is an expression vector comprising the polynucleotide provided herein. In another embodiment, provided herein is a cell comprising the expression vector. In another embodiment, provided herein is a composition comprising the expression vector.

In another embodiment, the invention provides a cell comprising the expression vector as described herein. In another embodiment, the present invention provides a cell comprising an expression vector comprising a polynucleotide encoding a CTP-modified polypeptide comprising or consisting of a GLP-1/Glucagon receptor agonist and at least one gonadotropin carboxy terminal peptides (CTPs) attached to the amino or carboxy terminus of the agonist. In another embodiment, the present invention provides a cell comprising an expression vector comprising a polynucleotide encoding a CTP-modified polypeptide consisting of a GLP-1/Glucagon receptor agonist and at least one gonadotropin carboxy terminal peptides (CTPs) attached to the amino or carboxy terminus of the agonist.

In another embodiment, the invention provides a composition comprising the expression vector as described herein. In another embodiment, the present invention provides a composition comprising an expression vector comprising a polynucleotide encoding a CTP-modified polypeptide comprising or consisting of a GLP-1/Glucagon receptor agonist and at least one gonadotropin carboxy terminal peptides (CTPs) attached to the amino or carboxy terminus of the agonist. In another embodiment, the present invention provides a cell comprising an expression vector comprising a polynucleotide encoding a CTP-modified polypeptide consisting of the agonist and at least one gonadotropin carboxy terminal peptides (CTPs) attached to the amino or carboxy terminus of the agonist. In another embodiment, the agonist is a polypeptide, or a peptide. In another embodiment, the peptide is oxyntomodulin.

In another embodiment, the invention provides a composition comprising the cell as described herein. In another embodiment, the cell is a eukaryotic cell. In another embodiment, the cell is a prokaryotic cell.

In one embodiment, the present invention provides a GLP-1/Glucagon receptor agonist. In another embodiment, the present invention provides a recombinant oxyntomodulin as described hereinabove. In one embodiment, the present invention provides an engineered oxyntomodulin as described hereinabove. In one embodiment, the engineered oxyntomodulin as described hereinabove is referred to as a CTP-modified oxyntomodulin.

In one embodiment, the CTPs that are attached to the carboxy terminus of the oxyntomodulin are attached in tandem to the carboxy terminus. In one embodiment, the CTPs that are attached to the amino terminus of the oxyntomodulin are attached in tandem to the amino terminus.

In one embodiment, an engineered GLP-1/Glucagon receptor agonist as described herein has equivalent or improved biological activity compared to the non-CTP-modified GLP-1/Glucagon receptor agonist. In another embodiment, an engineered GLP-1/Glucagon receptor agonist as provided herein has equivalent or improved pharmacological measurements compared to the non-CTP-modified GLP-1/Glucagon receptor agonist. In another embodiment, an engineered GLP-1/Glucagon receptor agonist as provided herein has equivalent or improved pharmacokinetics compared to the non-CTP-modified GLP-1/Glucagon receptor agonist. In another embodiment, an engineered GLP-1/Glucagon receptor agonist as provided herein has equivalent or improved pharmacodynamics compared to the non-CTP-modified GLP-1/Glucagon receptor agonist.

In another embodiment, the terms "CTP peptide," "carboxy terminal peptide" and "CTP sequence" are used interchangeably herein. In another embodiment, the carboxy terminal peptide is a full-length CTP. Each possibility represents a separate embodiment of the invention.

In another embodiment, a signal peptide is attached to the amino terminus of the CTP, as described in U.S. Pat. No. 7,553,940, which is incorporated by reference herein in its entirety.

In other embodiments, the term engineered oxyntomodulin refers to the amino acid sequence of a matured oxyntomodulin. In other embodiments, the term engineered oxyntomodulin refers to the amino acid sequence of the oxyntomodulin including its signal sequence or signal peptide.

In another embodiment, "signal sequence" and "signal peptide" are used interchangeably herein. In another embodiment, "sequence" when in reference to a polynucleotide molecule can refer to a coding portion. Each possibility represents a separate embodiment of the present invention.

In another embodiment, an engineered GLP-1/Glucagon receptor agonist comprising at least one CTP as described herein has enhanced in vivo biological activity compared the same GLP-1/Glucagon receptor agonist without at least one CTP. In one embodiment, the enhanced biological activity stems from the longer half-life of the engineered GLP-1/Glucagon receptor agonist while maintaining at least some biological activity. In another embodiment, the enhanced biological activity stems from enhanced biological activity resulting from the CTP modification. In another embodiment, the enhanced biological activity stems from both a longer half life and from enhanced functionality of the CTP-modified GLP-1/Glucagon receptor agonist.

In one embodiment, the at least one CTP sequence at the carboxy terminal end of the GLP-1/Glucagon receptor agonist provides enhanced protection against degradation of a GLP-1/Glucagon receptor agonist. In another embodiment, the at least one CTP sequence at the carboxy terminal end of the GLP-1/Glucagon receptor agonist provides enhanced protection against clearance. In another embodiment, the at least one CTP sequence at the carboxy terminal end of the GLP-1/Glucagon receptor agonist provides prolonged clearance time. In another embodiment, the at least one CTP sequence at the carboxy terminal end of the GLP-1/Glucagon receptor agonist enhances its Cmax. In another embodiment, the at least one CTP sequence at the carboxy terminal end of the GLP-1/Glucagon receptor agonist enhances its Tmax. In another embodiment, the at least one CTP sequence at the carboxy terminal end of the GLP-1/Glucagon receptor agonist prolongs its T½.

In another embodiment, a conjugated GLP-1/Glucagon receptor agonist of this invention is used in the same manner as an unmodified conjugated GLP-1/Glucagon receptor agonist. In another embodiment, a conjugated oxyntomodulin of this invention is used in the same manner as an unmodified conjugated oxyntomodulin. In another embodiment, a conjugated oxyntomodulin of this invention has an increased circulating half-life and plasma residence time, decreased clearance, and increased clinical activity in vivo. In another embodiment, due to the improved properties of the conjugated oxyntomodulin as described herein, this conjugate is administered less frequently than the unmodified form of the same oxyntomodulin.

In another embodiment, decreased frequency of administration results in improved treatment strategy, which in one embodiment, leads to improved patient compliance leading to improved treatment outcomes, as well as improved patient quality of life. In another embodiment, compared to conventional conjugates of oxyntomodulins, it has been found that conjugates having the molecular weight and linker structure of the conjugates as described herein have an improved potency, improved stability, elevated AUC levels, and enhanced circulating half-life.

In another embodiment, the present invention further provides a pharmaceutical composition comprising a CTP-modified polypeptide consisting of a GLP-1/Glucagon receptor agonist and three gonadotropin carboxy terminal peptides (CTPs) attached to the carboxy terminus of the oxyntomodulin.

In another embodiment, the present invention further provides a pharmaceutical composition comprising a CTP-modified polypeptide consisting of an oxyntomodulin and three gonadotropin carboxy terminal peptides (CTPs) attached to the carboxy terminus of the oxyntomodulin.

In another embodiment, provided herein is a composition comprising a conjugated GLP-1/Glucagon receptor agonist as provided herein. In another embodiment, provided herein is a pharmaceutical composition comprising the conjugated GLP-1/Glucagon receptor agonist as provided herein. In another embodiment, provided herein is a pharmaceutical composition comprising a therapeutically effective amount of the conjugated GLP-1/Glucagon receptor agonist as provided herein. In one embodiment, a therapeutically effective amount of a conjugated GLP-1/Glucagon receptor agonist is determined according to factors such as the specific condition being treated, the condition of the patient being treated, as well as the other ingredients in the composition.

In another embodiment, provided herein is a composition comprising a conjugated oxyntomodulin as provided herein. In another embodiment, provided herein is a pharmaceutical composition comprising the conjugated oxyntomodulin as provided herein. In another embodiment, provided herein is a pharmaceutical composition comprising a therapeutically effective amount of the conjugated oxyntomodulin as provided herein. In one embodiment, a therapeutically effective amount of a conjugated oxyntomodulin is determined according to factors such as the specific condition being treated, the condition of the patient being treated, as well as the other ingredients in the composition.

In one embodiment, a CTP-modified GLP-1/Glucagon receptor agonist of the present invention has therapeutic uses. In another embodiment, a CTP-modified GLP-1/Glucagon receptor agonist of the present invention has prophylactic uses.

In another embodiment, a CTP-modified oxyntomodulin of the present invention has therapeutic uses. In another embodiment, a CTP-modified oxyntomodulin of the present invention has prophylactic uses.

In one embodiment, provided herein is a method of reducing the dosing frequency of GLP-1/Glucagon receptor agonist in a subject, comprising the step of attaching at least one chorionic gonadotrophin carboxy terminal peptides to an amino or a carboxy terminus of the GLP-1/Glucagon receptor agonist, thereby reducing the dosing frequency of GLP-1/Glucagon receptor agonist. In another embodiment, the CTP sequence modification is advantageous in permitting the usage of lower dosages. In some embodiments, the CTP sequences modification is advantageous in permitting fewer dosages. In some embodiments, the CTP sequences modification is advantageous in permitting a safe, long-acting effect.

In another embodiment, provided herein is a method of reducing the dosing frequency of oxyntomodulin in a subject, comprising the step of attaching at least one chorionic gonadotrophin carboxy terminal peptides to an amino or a carboxy terminus of the oxyntomodulin, thereby reducing the dosing frequency of oxyntomodulin. In another embodiment, the CTP sequence modification is advantageous in permitting the usage of lower dosages. In some embodiments, the CTP sequences modification is advantageous in permitting fewer dosages. In some embodiments, the CTP sequences modification is advantageous in permitting a safe, long-acting effect.

In one embodiment, provided herein is a method of reducing cholesterol in a subject, comprising the step of attaching at least one chorionic gonadotrophin carboxy terminal peptides to an amino or a carboxy terminus of the oxyntomodulin, thereby reducing cholesterol in a subject.

In another embodiment, provided herein is a method of reducing glycerol in a subject, comprising the step of attaching at least one chorionic gonadotrophin carboxy terminal peptides to an amino or a carboxy terminus of the oxyntomodulin, thereby reducing glycerol in a subject.

In one embodiment, the present invention provides a long-acting OXM. In one embodiment, a long-acting OXM of the invention maintains the biological activity of unmodified OXM. In another embodiment, the long-acting OXM of the invention comprises OXM biological activity. In another embodiment, the biological activity of a long-acting OXM of the invention comprises reducing digestive secretions. In another embodiment, the biological activity of a long-acting OXM of the invention comprises reducing and delaying gastric emptying. In another embodiment, the biological activity of a long-acting OXM of the invention comprises the inhibition of the fed motility pattern in the small intestine. In another embodiment, the biological activity of a long-acting OXM of the invention comprises the inhibition of acid secretion stimulated by pentagastrin. In another embodiment, the biological activity of a long-acting OXM of the invention comprises an increase of gastric somatostatin release. In another embodiment, the biological activity of a long-acting OXM of the invention comprises potentiating the effects of peptide YY. In another embodiment, the biological activity of a long-acting OXM of the invention comprises the inhibition of ghrelin release. In another embodiment, the biological activity of a long-acting OXM of the invention comprises the stimulation of aminopyrine accumulation and cAMP production. In another embodiment, the biological activity of a long-acting OXM of the invention comprises binding the GLP-1 receptor. In another embodiment, the biological activity of a long-acting OXM of the invention comprises stimulating H+ production by activating adenylate cyclase. In another embodiment, the biological activity of a long-acting OXM of the invention comprises inhibiting histamine-stimulated gastric acid secretion. In another embodiment, the biological activity of a long-acting OXM of the invention comprises inhibiting food intake. In another embodiment, the biological activity of a long-acting OXM of the invention comprises stimulating insulin release. In another embodiment, the biological activity of a long-acting OXM of the invention comprises inhibiting exocrine pancreatic secretion.

In another embodiment, the biological activity of a long-acting OXM of the invention comprises inhibiting pancreatic secretion through a vagal neural indirect mechanism. In another embodiment, the biological activity of a long-acting OXM of the invention comprises reducing hydromineral transport through the small intestine. In another embodiment, the biological activity of a long-acting OXM of the invention comprises stimulating glucose uptake. In another embodiment, the biological activity of a long-acting OXM of the invention comprises controlling/stimulating somatostatin secretion. In another embodiment, the biological activity of a long-acting OXM of the invention comprises reduction in both food intake and body weight gain. In another embodiment, the biological activity of a long-acting OXM of the invention comprises reduction in adiposity. In another embodiment, the biological activity of a long-acting OXM of the invention comprises appetite suppression. In another embodiment, the biological activity of a long-acting OXM of the invention comprises induction of anorexia. In another embodiment, the biological activity of a long-acting OXM of the invention comprises reducing body weight in overweight and obese subjects. In another embodiment, the biological activity of a long-acting OXM of the invention comprises inducing changes in the levels of the adipose hormones leptin and adiponectin. In another embodiment, the biological activity of a long-acting OXM of the invention comprises increasing energy expenditure in addition to decreasing energy intake in overweight and obese subjects.

Thus, in one embodiment, the present invention provides a method of effecting any of the above-mentioned biological activities of OXM by administering a CTP-modified OXM of the present invention. In another embodiment, the present invention further provides a method for reducing food intake, reducing body weight, or both in a subject, comprising the step of administering to the subject a CTP-modified oxyntomodulin peptide. In another embodiment, the subject has diabetes. In another embodiment, the subject is overweight. In another embodiment, the subject is obese.

In one embodiment, the terms "reducing, reduction, lowering, etc." when used in relation to the methods provided herein refer to 100% reduction from a previously measured or determined level or from a normal level. In another embodiment, the reduction is by 89-99% from a previously determined level. In another embodiment, the reduction is by 79-88% from a previously determined level. In another embodiment, the reduction is by 69-78% from a previously determined level. In another embodiment, the reduction is by 59-68% from a previously determined level. In another embodiment, the reduction is by 49-58% from a previously determined level. In another embodiment, the reduction is by 39-48% from a previously determined level. In another embodiment, the reduction is by 29-38% from a previously determined level. In another embodiment, the reduction is by 19-28% from a previously determined level. In another embodiment, the reduction is by 9-18% from a previously determined level. In another embodiment, the reduction is by 5-8% from a previously determined level. In another embodiment, the reduction is by 1-4% from a previously determined level.

The in-vivo biological activity of OXM-CTP variants was assessed in two animal models, IPGTT in mice, which evaluate the ability of OXM to induce glucose tolerance following glucose administration, and food intake inhibition in lean rats, which assess the ability of OXM to inhibit animal's food consumption. It was demonstrated that OXM-CTP variants: CTP-OXM-CTP-CTP, OXM-CTP-CTP, OXM-CTP-CTP-CTP, OXM-CTP-CTP-CTP-CTP and OXM-CTP-CTP-CTP-CTP-CTP induced glucose tolerance as reflected by reduction of 20-30% of blood glucose AUC compared to vehicle group (see Example 4, herein). These results indicate that the biological activity of OXM-CTP variants was not inhibited in-vivo due to potential steric interference of CTP fusion to the binding of OXM to its receptor. The marked reduction in glucose induced by these variants correlated with their improved PK profiles. Therefore, in one embodiment, provided herein is a method of inducing glucose tolerance in a subject, the method comprising the step of administering to the subject an effective dose of a composition comprising a CTP-modified polypeptide comprising an oxyntomodulin (OXM) peptide and at least one chorionic gonadotrophin carboxy terminal peptide (CTP) attached to the amino terminus or caboxy terminus of the oxyntomodulin peptide, thereby inducing glucose tolerance in a subject.

In another embodiment, provided herein is a method of inducing glucose tolerance in a subject, the method comprising the step of administering to the subject an effective dose of a composition comprising a CTP-modified polypeptide comprising a GLP-1/Glucagon receptor agonist and at least one chorionic gonadotrophin carboxy terminal peptide (CTP) attached to the amino terminus or caboxy terminus of the GLP-1/Glucagon receptor agonist peptide, thereby inducing glucose tolerance in a subject.

In another embodiment, provided herein is a use of a CTP-modified polypeptide comprising a dual GLP-1/Glucagon receptor agonist and at least one chorionic gonadotrophin carboxy terminal peptide (CTP) attached to the amino terminus or caboxy terminus of said agonist for inducing glucose tolerance in a subject. In one embodiment, said dual GLP-1/Glucagon receptor agonist is oxyntomodulin.

In another embodiment, provided herein is a use of a CTP-modified polypeptide comprising a dual GLP-1/Glucagon receptor agonist and at least one chorionic gonadotrophin carboxy terminal peptide (CTP) attached to the amino terminus or caboxy terminus of said agonist in the preparation of a medicament for inducing glucose tolerance in a subject. In one embodiment, said dual GLP-1/Glucagon receptor agonist is oxyntomodulin.

In one embodiment, provided herein is a method of increasing insulin sensitivity in a subject, the method comprising the step of administering to the subject an effective dose of a composition comprising a CTP-modified polypeptide comprising a GLP-1/Glucagon receptor agonist and at least one chorionic gonadotrophin carboxy terminal peptide (CTP) attached to the amino terminus or caboxy terminus of the GLP-1/Glucagon receptor agonist peptide, thereby increasing insulin sensitivity in a subject.

In one embodiment, provided herein is a method of reducing insulin resistance in a subject, the method comprising the step of administering to the subject an effective dose of a composition comprising a CTP-modified polypeptide comprising a GLP-1/Glucagon receptor agonist and at least one chorionic gonadotrophin carboxy terminal peptide (CTP) attached to the amino terminus or caboxy terminus of the GLP-1/Glucagon receptor agonist peptide, thereby reducing insulin resistance in a subject.

In one embodiment, provided herein is a method of increasing insulin sensitivity and reducing insulin resistance in a subject, the method comprising the step of administering to the subject an effective dose of a composition comprising a CTP-modified polypeptide comprising a GLP-1/Glucagon receptor agonist and at least one chorionic gonadotrophin carboxy terminal peptide (CTP) attached to the amino terminus or caboxy terminus of the GLP-1/Glucagon receptor agonist peptide, thereby increasing insulin sensitivity and reducing insulin resistance in a subject.

The ability of OXM-CTP variants OXM-3CTP, OXM-4CTP and OXM-5CTP to inhibit food intake was assessed. Native OXM inhibited food intake only in the first hour following administration, however, all variants manifested substantial prolonged improved inhibition in food intake compared to OXM. The cumulative food inhibition of OXM-5CTP was surprisingly sustained for at least 141 hrs emphasizing the elongated half life of this variant (see Example 5, herein).

Hence, in one embodiment, provided herein is a method of inducing food intake inhibition in a subject, the method comprising the step of administering to the subject an effective dose of a composition comprising a CTP-modified polypeptide comprising an oxyntomodulin (OXM) peptide and at least one chorionic gonadotrophin carboxy terminal peptide (CTP) attached to the amino terminus or carboxy terminus of the oxyntomodulin peptide, thereby inducing food intake inhibition in the subject.

In another embodiment, provided herein is a method of inducing food intake inhibition in a subject, the method comprising the step of administering to the subject an effective dose of a composition comprising a CTP-modified polypeptide comprising a GLP-1/Glucagon receptor agonist and at least one chorionic gonadotrophin carboxy terminal peptide (CTP) attached to the amino terminus or carboxy terminus of the GLP-1/Glucagon receptor agonist peptide, thereby inducing food intake inhibition in the subject.

In another embodiment, provided herein is a method of preventing, reducing or suppressing food intake in a subject, the method comprising the step of administering to the subject an effective dose of a composition comprising CTP-modified polypeptide comprising a GLP-1/Glucagon receptor agonist and at least one chorionic gonadotrophin carboxy terminal peptide (CTP) attached to the amino terminus or carboxy terminus of the GLP-1/Glucagon receptor agonist peptide, thereby preventing reducing or suppressing food intake by a subject. In another embodiment, preventing, reducing or suppressing food intake by a subject reduces the chances of the subject developing undesired weight gain. In another embodiment, preventing reducing or suppressing food intake in a subject reduces the chances of the subject developing obesity.

In another embodiment, provided herein is a use of a CTP-modified polypeptide comprising a GLP-1/Glucagon receptor agonist and at least one chorionic gonadotrophin carboxy terminal peptide (CTP) attached to the amino terminus or carboxy terminus of said agonist for preventing undesired weight gain by a subject. In one embodiment, said GLP-1/Glucagon receptor agonist is oxyntomodulin.

In another embodiment, provided herein is a use of a CTP-modified polypeptide comprising a GLP-1/Glucagon receptor agonist and at least one chorionic gonadotrophin carboxy terminal peptide (CTP) attached to the amino terminus or carboxy terminus of said agonist in the preparation of a medicament for preventing undesired weight gain by a subject. In one embodiment, said GLP-1/Glucagon receptor agonist is oxyntomodulin.

In another embodiment, provided herein is a method of preventing, reducing or suppressing food intake in a subject, the method comprising the step of administering to the subject an effective dose of a composition comprising CTP-modified polypeptide comprising an oxyntomodulin (OXM) peptide and at least one chorionic gonadotrophin carboxy terminal peptide (CTP) attached to the amino terminus or carboxy terminus of the oxyntomodulin peptide, thereby preventing reducing or suppressing food intake by a subject. In another embodiment, preventing, reducing or suppressing food intake by a subject reduces the chances of the subject developing undesired weight gain. In another embodiment, preventing reducing or suppressing food intake in a subject reduces the chances of the subject developing obesity.

In another embodiment, provided herein is a method of preventing undesired weight gain by a subject, the method comprising the step of administering to the subject an effective dose of a composition comprising CTP-modified polypeptide comprising a GLP-1/Glucagon receptor agonist and at least one chorionic gonadotrophin carboxy terminal peptide (CTP) attached to the amino terminus or carboxy terminus of the GLP-1/Glucagon receptor agonist peptide, thereby preventing weight gain in a subject. In another embodiment, the weight gain leads to or results in obesity of the subject. In another embodiment, the risk of gaining weight gain is due to a psychological condition, or due to a genetic predisposposition to gain weight by the subject. In another embodiment, the psychological condition is depression, anxiety or post-traumatic stress disorder (PTSD).

In another embodiment, provided herein is a use of a CTP-modified polypeptide comprising a GLP-1/Glucagon receptor agonist and at least one chorionic gonadotrophin carboxy terminal peptide (CTP) attached to the amino terminus or carboxy terminus of said agonist for preventing undesired weight gain by a subject. In one embodiment, said GLP-1/Glucagon receptor agonist is oxyntomodulin.

In another embodiment, provided herein is a use of a CTP-modified polypeptide comprising a GLP-1/Glucagon receptor agonist and at least one chorionic gonadotrophin carboxy terminal peptide (CTP) attached to the amino terminus or carboxy terminus of said agonist in the preparation of a medicament for preventing undesired weight gain by a subject. In one embodiment, said GLP-1/Glucagon receptor agonist is oxyntomodulin.

In another embodiment, provided herein is a method of preventing undesired weight gain by a subject, the method comprising the step of administering to the subject an effective dose of a composition comprising CTP-modified polypeptide comprising an oxyntomodulin (OXM) peptide and at least one chorionic gonadotrophin carboxy terminal peptide (CTP) attached to the amino terminus or carboxy terminus of the oxyntomodulin peptide, thereby preventing weight gain in a subject. In another embodiment, the weight gain leads to or results in obesity of the subject. In another embodiment, the risk of gaining weight gain is due to a psychological condition, or due to a genetic predisposposition to gain weight by the subject. In another embodiment, the psychological condition is depression, anxiety or post-traumatic stress disorder (PTSD).

In another embodiment, provided herein is a method of treating obesity in a subject, the method comprising administering to the subject an effective dose of a composition comprising a CTP-modified polypeptide comprising a GLP-1/Glucagon receptor agonist peptide and at least one chorionic gonadotrophin carboxy terminal peptide attached to the amino terminus or carboxy terminus of the GLP-1/Glucagon receptor agonist peptide, thereby treating obesity in the subject. In another embodiment, the subject is genetically predisposed to being obese. In another embodiment, the method of treating obesity results in a reduction of body weight in a subject. In another embodiment, the reduction in body weight is due to body fat reduction.

In another embodiment, provided herein is a use of a CTP-modified polypeptide comprising a GLP-1/Glucagon receptor agonist and at least one chorionic gonadotrophin carboxy terminal peptide attached to the amino terminus or carboxy terminus of said agonist for treating obesity in a subject. In one embodiment, said GLP-1/Glucagon receptor agonist is oxyntomodulin.

In another embodiment, provided herein is a use of a CTP-modified polypeptide comprising a GLP-1/Glucagon receptor agonist and at least one chorionic gonadotrophin carboxy terminal peptide attached to the amino terminus or carboxy terminus of said agonist in the preparation of a medicament for treating obesity in a subject. In one embodiment, said GLP-1/Glucagon receptor agonist is oxyntomodulin.

In another embodiment, provided herein is a method of treating obesity in a subject, the method comprising administering to the subject an effective dose of a composition comprising a CTP-modified polypeptide comprising an oxyntomodulin peptide and at least one chorionic gonadotrophin carboxy terminal peptide attached to the amino terminus or carboxy terminus of the oxyntomodulin peptide, thereby treating obesity in the subject. In another embodiment, the subject is genetically predisposed to being obese.

In one embodiment, provided herein is a method of treating type II diabetes in a subject, the method comprising administering to the subject an effective dose of a composition comprising a CTP-modified polypeptide comprising a GLP-1/Glucagon receptor agonist peptide and at least one chorionic gonadotrophin carboxy terminal peptide attached to the amino terminus or carboxy terminus of the GLP-1/Glucagon receptor agonist peptide, thereby treating type II diabetes in the subject.

In another embodiment, provided herein is a use of a CTP-modified polypeptide comprising a GLP-1/Glucagon receptor agonist and at least one chorionic gonadotrophin carboxy terminal peptide attached to the amino terminus or carboxy terminus of said agonist for treating type II diabetes in a subject. In one embodiment, said GLP-1/Glucagon receptor agonist is oxyntomodulin.

In another embodiment, provided herein is a use of a CTP-modified polypeptide comprising a GLP-1/Glucagon receptor agonist and at least one chorionic gonadotrophin carboxy terminal peptide attached to the amino terminus or carboxy terminus of said agonist in the preparation of a medicament for treating type II diabetes in a subject. In one embodiment, said GLP-1/Glucagon receptor agonist is oxyntomodulin.

In one embodiment, provided herein is a method of treating type II diabetes in a subject, the method comprising administering to the subject an effective dose of a composition comprising a CTP-modified polypeptide comprising an oxyntomodulin peptide and at least one chorionic gonadotrophin carboxy terminal peptide attached to the amino terminus or carboxy terminus of the oxyntomodulin peptide, thereby treating type II diabetes in the subject.

In another embodiment, provided herein is a method of treating a metabolic disorder in a subject, the method comprising administering to the subject an effective dose of a composition comprising a CTP-modified polypeptide comprising a GLP-1/Glucagon receptor agonist and at least one chorionic gonadotrophin carboxy terminal peptide attached to the amino terminus or carboxy terminus of the GLP-1/Glucagon receptor agonist peptide, thereby treating a metabolic disorder in the subject.

In another embodiment, provided herein is a use of a CTP-modified polypeptide comprising a GLP-1/Glucagon receptor agonist and at least one chorionic gonadotrophin carboxy terminal peptide attached to the amino terminus or carboxy terminus of said agonist for treating a metabolic disorder in a subject. In one embodiment, said GLP-1/Glucagon receptor agonist is oxyntomodulin.

In another embodiment, provided herein is a use of a CTP-modified polypeptide comprising a GLP-1/Glucagon receptor agonist and at least one chorionic gonadotrophin carboxy terminal peptide attached to the amino terminus or carboxy terminus of said agonist in the preparation of a medicament for treating a metabolic disorder in a subject. In one embodiment, said GLP-1/Glucagon receptor agonist is oxyntomodulin.

In another embodiment, provided herein is a method of treating a metabolic disorder in a subject, the method comprising administering to the subject an effective dose of a composition comprising a CTP-modified polypeptide comprising an oxyntomodulin peptide and at least one chorionic gonadotrophin carboxy terminal peptide attached to the amino terminus or carboxy terminus of the oxyntomodulin peptide, thereby treating a metabolic disorder in the subject.

In another embodiment, the metabolic disorder is diabetic ketoacidosis, or diabetes mellitus or any glucose-related metabolic disorder known in the art. In another embodiment, the metabolic disorder results from a lack of insulin and an overabundance of glucose in a subject.

In another embodiment, the engineered GLP-1/Glucagon receptor agonist variants of the present invention are synthesized using a polynucleotide molecule encoding a polypeptide of the present invention. In another embodiment, the polynucleotide molecule encoding the engineered GLP-1/Glucagon receptor agonist of the present invention is ligated into an expression vector, comprising a transcriptional control of a cis-regulatory sequence (e.g., promoter sequence). In another embodiment, the cis-regulatory sequence is suitable for directing constitutive expression of an engineered GLP-1/Glucagon receptor agonist of the present invention. In another embodiment, the cis-regulatory sequence is suitable for directing tissue-specific expression of the engineered GLP-1/Glucagon receptor agonist peptides of the present invention. In another embodiment, the cis-regulatory sequence is suitable for directing inducible expression of the engineered GLP-1/Glucagon receptor agonist variants of the present invention.

In one embodiment, tissue-specific promoters suitable for use with the present invention include sequences which are functional in one or more specific cell populations. Examples include, but are not limited to, promoters such as albumin that is liver-specific [Pinkert et al., (1987) Genes Dev. 1:268-277], lymphoid-specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). Inducible promoters suitable for use with the present invention include, for example, the tetracycline-inducible promoter (Srour, M. A., et al., 2003. Thromb. Haemost. 90: 398-405).

In one embodiment, the phrase "a polynucleotide molecule" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, a "complementary polynucleotide sequence" refers to a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, a "genomic polynucleotide sequence" refers to a sequence derived (isolated) from a chromosome and thus it represents a contiguous portion of a chromosome.

In one embodiment, a "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing therebetween. In one embodiment, the intronic sequences can be of any source, including of other genes, and typically includes conserved splicing signal sequences. In one embodiment, intronic sequences include cis-acting expression regulatory elements.

In one embodiment, following expression and secretion, the signal peptides are cleaved from the precursor engineered oxyntomodulin peptides resulting in the mature engineered oxyntomodulin peptides.

In one embodiments, polynucleotides of the present invention are prepared using PCR techniques, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention which encode the engineered GLP-1/Glucagon receptor agonist provided herein are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In another embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the CTP-modified GLP-1/Glucagon receptor agonist provided herein. In another embodiment, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In one embodiment, non-bacterial expression systems are used (e.g. mammalian expression systems such as CHO cells) to express the GLP-1/Glucagon receptor agonist provided herein. In another embodiment, the GLP-1/Glucagon receptor agonist is oxyntomodulin. In another embodiment, the oxyntomodulin is modified by the addition of at least one CTP, as further provided herein. In another embodiment, the expression vector used to express polynucleotides of the present invention in mammalian cells is pCI-dhfrr vector. Construction of the pCI-dhfrr vector is described, according to one embodiment, in Example's Materials and Methods, below.

In one embodiment, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion proteins are engineered with a specific cleavage site to aid in recovery of the polypeptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447, which is incorporated by reference herein in its entirety. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In one embodiment, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRepS, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In one embodiment, expression vectors containing regulatory elements from eukaryotic viruses such as retroviruses are used in the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In one embodiment, recombinant viral vectors are useful for in vivo expression of the oxyntomodulin peptides of the present invention since they offer advantages such as lateral infection and targeting specificity. In one embodiment, lateral infection is inherent in the life cycle of, for example, a retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992, incorporated herein by reference, for positive-negative selection methods.

In one embodiment, introduction of nucleic acid by viral infection offers several advantages over other methods such as lipofection and electroporation, since higher transfection efficiency can be obtained due to the infectious nature of viruses.

It will be appreciated that the engineered GLP-1/Glucagon receptor agonist or oxyntomodulin peptides of the present invention can also be expressed from a nucleic acid construct administered to the individual employing any suitable mode of administration (e.g., subcutaneous administration, oral administration, intra-nasal administration, intra-venal administration, or in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In one embodiment, transformed cells are cultured under effective conditions, which allow for the expression of high amounts of recombinant engineered oxyntomodulin peptides. In another embodiment, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. In another embodiment, culturing is carried out at a temperature, pH and oxygen content appropriate for a recombinant cell. In another embodiment, the determination of culturing conditions are within the expertise of one of ordinary skill in the art.

In one embodiment, depending on the vector and host system used for production, the resultant engineered CTP-modified GLP-1/Glucagon receptor agonist or, in another embodiment, the resultant CTP-modified oxyntomodulin peptides of the present invention are expressed within a recombinant cell for glycosylation of the CTP to take place, are secreted into the fermentation medium, or are retained on the outer surface of a mammalian cell.

In one embodiment, following a predetermined time in culture, recovery of the recombinant engineered GLP-1/Glucagon receptor agonist or oxyntomodulin is effected.

In one embodiment, the phrase "recovering the recombinant engineered oxyntomodulin" refers to collecting the whole fermentation medium containing the polypeptide and need not imply additional steps of separation or purification.

In one embodiment, engineered oxyntomodulin or variants thereof provided herein are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the engineered GLP-1/Glucagon receptor agonist or oxyntomodulin of the present invention and fused cleavable moiety. Further, a fusion protein can be designed so that the polypeptide can be readily isolated by affinity chromatography; e.g., by immobilization on a column specific for the cleavable moiety. A cleavage site is engineered between the engineered oxyntomodulin and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265: 15854-15859 (1990)].

In one embodiment, the engineered oxyntomodulin provided herein is retrieved in "substantially pure" form.

In one embodiment, the phrase "substantially pure" refers to a purity that allows for the effective use of the protein in the applications described herein.

The engineered GLP-1/Glucagon receptor agonist or oxyntomodulin provided herein can also be synthesized using in vitro expression systems. In another embodiment, in vitro synthesis methods are well known in the art and the components of the system are commercially available.

In one embodiment, the recombinant engineered oxyntomodulin peptides are synthesized and purified; their therapeutic efficacy can be assayed either in vivo or in vitro. The binding activities of the recombinant engineered oxyntomodulin peptides of the present invention can be ascertained using various assays as known to one of skill in the art.

In another embodiment, the GLP-1/Glucagon receptor agonist or engineered oxyntomodulin of the present invention can be provided to the individual per se. In one embodiment, the engineered GLP-1/Glucagon receptor agonist or oxyntomodulin of the present invention can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In another embodiment, the phrases "physiologically acceptable carrier" and "pharmaceutically acceptable carrier" which are interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979)).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

Various embodiments of dosage ranges are contemplated by this invention. The dosage of the CTP-modified GLP-1/Glucagon receptor agonist of the present invention, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In one embodiment, the dosage of the CTP-modified GLP-1/Glucagon receptor agonist is 1-5 mg/day. In one embodiment, the dosage of the CTP-modified oxyntomodulin is 1-3 mg/day. In another embodiment, the dosage of the CTP-modified oxyntomodulin is 2 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the CTP-modified GLP-1/Glucagon receptor agonist dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

In another embodiment, a polypeptide comprising a GLP-1/Glucagon receptor agonist and at least one CTP unit is formulated in an intranasal dosage form. In another embodiment, a polypeptide comprising a GLP-1/Glucagon receptor agonist and at least one CTP unit is formulated in an injectable dosage form. In another embodiment, a polypeptide comprising a GLP-1/Glucagon receptor agonist and at least one CTP unit is administered to a subject in a dose ranging from 0.0001 mg to 0.6 mg. In another embodiment, a polypeptide comprising a GLP-1/Glucagon receptor agonist and at least one CTP unit is administered to a subject in a dose ranging from 0.001 mg to 0.005 mg. In another embodiment, a polypeptide comprising a GLP-1/Glucagon receptor agonist and at least one CTP unit is administered to a subject in a dose ranging from 0.005 mg to 0.01 mg. In another embodiment, a polypeptide comprising a GLP-1/Glucagon receptor agonist and at least one CTP unit is administered to a subject in a dose ranging from 0.01 mg to 0.3 mg. In another embodiment, a polypeptide comprising a GLP-1/Glucagon receptor agonist and at least one CTP unit is administered to a subject in a dose in a dose ranging from 0.2 mg to 0.6 mg. In another embodiment, the GLP-1/Glucagon receptor agonist is free of CTPs on its amino terminus.

In another embodiment, a polypeptide comprising a GLP-1/Glucagon receptor agonist and at least one CTP unit is formulated in an intranasal dosage form. In another embodiment, a polypeptide comprising a GLP-1/Glucagon receptor agonist and at least one CTP unit is formulated in an injectable dosage form. In another embodiment, a polypeptide comprising a GLP-1/Glucagon receptor agonist and at least one CTP unit is administered to a subject in a dose ranging from 0.0001 mg to 0.6 mg. In another embodiment, a polypeptide comprising a GLP-1/Glucagon receptor agonist and at least one CTP unit is administered to a subject in a dose ranging from 0.001 mg to 0.005 mg. In another embodiment, a polypeptide comprising a GLP-1/Glucagon receptor agonist and at least one CTP unit is administered to a subject in a dose ranging from 0.005 mg to 0.01 mg. In another embodiment, a polypeptide comprising a GLP-1/Glucagon receptor agonist and at least one CTP unit is administered to a subject in a dose ranging from 0.01 mg to 0.3 mg. In another embodiment, a polypeptide comprising a GLP-1/Glucagon receptor agonist and at least one CTP unit is administered to a subject in a dose in a dose ranging from 0.2 mg to 0.6 mg. In another embodiment, the GLP-1/Glucagon receptor agonist is free of CTPs on its amino terminus.

In another embodiment, a polypeptide comprising a GLP-1/Glucagon receptor agonist and at least one CTP unit is administered to a subject in a dose ranging from 1-100 micrograms. In another embodiment, a polypeptide comprising a GLP-1/Glucagon receptor agonist and at least one CTP unit is administered to a subject in a dose ranging from 10-80 micrograms. In another embodiment, a polypeptide comprising a GLP-1/Glucagon receptor agonist and at least one CTP unit is administered to a subject in a dose ranging from 20-60 micrograms. In another embodiment, a polypeptide comprising a GLP-1/Glucagon receptor agonist and at least one CTP unit is administered to a subject in a dose ranging from 10-50 micrograms. In another embodiment, a polypeptide comprising a GLP-1/Glucagon receptor agonist and at least one CTP unit is administered to a subject in a dose ranging from 40-80 micrograms. In another embodiment, a polypeptide comprising a GLP-1/Glucagon receptor agonist and at least one CTP unit is administered to a subject in a dose ranging from 10-30 micrograms. In another embodiment, a polypeptide comprising a GLP-1/Glucagon receptor agonist and at least one CTP unit is administered to a subject in a dose ranging from 30-60 micrograms.

In another embodiment, a polypeptide comprising a GLP-1/Glucagon receptor agonist and at least one CTP unit is administered to a subject in a dose ranging from 1-100 micrograms. In another embodiment, a polypeptide comprising a GLP-1/Glucagon receptor agonist and at least one CTP unit is administered to a subject in a dose ranging from 10-80 micrograms. In another embodiment, a polypeptide comprising a GLP-1/Glucagon receptor agonist and at least one CTP unit is administered to a subject in a dose ranging from 20-60 micrograms. In another embodiment, a polypeptide comprising a GLP-1/Glucagon receptor agonist and at least one CTP unit is administered to a subject in a dose ranging from 10-50 micrograms. In another embodiment, a polypeptide comprising a GLP-1/Glucagon receptor agonist and at least one CTP unit is administered to a subject in a dose ranging from 40-80 micrograms. In another embodiment, a polypeptide comprising a GLP-1/Glucagon receptor agonist and at least one CTP unit is administered to a subject in a dose ranging from 10-30 micrograms. In another embodiment, a polypeptide comprising a GLP-1/Glucagon receptor agonist and at least one CTP unit is administered to a subject in a dose ranging from 30-60 micrograms.

In another embodiment, a polypeptide comprising a GLP-1/Glucagon receptor agonist and at least one CTP unit is administered to a subject in a dose ranging from 0.2 mg to 2 mg. In another embodiment, a polypeptide comprising a GLP-1/Glucagon receptor agonist and at least one CTP unit is administered to a subject in a dose ranging from 2 mg to 6 mg. In another embodiment, a polypeptide comprising a GLP-1/Glucagon receptor agonist and at least one CTP unit is administered to a subject in a dose ranging from 4 mg to 10 mg. In another embodiment, a polypeptide comprising a GLP-1/Glucagon receptor agonist and at least one CTP unit is administered to a subject in a dose ranging from 5 mg and 15 mg.

In another embodiment, a polypeptide comprising a GLP-1/Glucagon receptor agonist and at least one CTP unit is administered to a subject in a dose ranging from 0.2 mg to 2 mg. In another embodiment, a polypeptide comprising a GLP-1/Glucagon receptor agonist and at least one CTP unit is administered to a subject in a dose ranging from 2 mg to 6 mg. In another embodiment, a polypeptide comprising a GLP-1/Glucagon receptor agonist and at least one CTP unit is administered to a subject in a dose ranging from 4 mg to 10 mg. In another embodiment, a polypeptide comprising a GLP-1/Glucagon receptor agonist and at least one CTP unit is administered to a subject in a dose ranging from 5 mg and 15 mg.

In another embodiment, the dosage of CTP-modified GLP-1/Glucagon receptor agonist is such that it contains 65% of the amount of the agonist than that administered using the non-CTP-modified GLP-1/Glucagon receptor agonist. In another embodiment, the dosage of CTP-modified GLP-1/Glucagon receptor agonist is such that it contains 55% of the amount of the agonist than that administered using the non-CTP-modified GLP-1/Glucagon receptor agonist. In another embodiment, the dosage of CTP-modified GLP-1/Glucagon receptor agonist is such that it contains 45% of the amount of the agonist than that administered using the non-CTP-modified GLP-1/Glucagon receptor agonist. In another embodiment, the dosage of CTP-modified GLP-1/Glucagon receptor agonist is such that it contains 10% of the amount of the agonist than that administered using the non-CTP-modified GLP-1/Glucagon receptor agonist. In another embodiment, the dosage of CTP-modified GLP-1/Glucagon receptor agonist is such that it contains 25% of the amount of the agonist than that administered using the non-CTP-modified GLP-1/Glucagon receptor agonist. In another embodiment, the dosage of CTP-modified GLP-1/Glucagon receptor agonist is such that it contains 35% of the amount of the agonist than that administered using the non-CTP-modified GLP-1/Glucagon receptor agonist. In another embodiment, the dosage of CTP-modified GLP-1/Glucagon receptor agonist is such that it contains 75% of the amount of the agonist than that administered using the non-CTP-modified GLP-1/Glucagon receptor agonist. In another embodiment, the dosage of CTP-modified GLP-1/Glucagon receptor agonist is such that it contains 100% of the amount of the agonist than that administered using the non-CTP-modified agonist. However, even if the dosage contains the same amount of agonist as non-CTP-modified GLP-1/Glucagon receptor agonist, it is still advantageous to subjects in that it will be administered less frequently because of its increased half-life compared to normal agonist.

In another embodiment, a therapeutically effective amount of a conjugated GLP-1/Glucagon receptor agonist is between 50-500 IU per kg body weight administered once a day. In another embodiment, a therapeutically effective amount of a conjugated GLP-1/Glucagon receptor agonist is 150-250 IU per kg body weight, administered once a day. In another embodiment, a pharmaceutical composition comprising a conjugated GLP-1/Glucagon receptor agonist is formulated at a strength effective for administration by various means to a human patient.

In one embodiment, the CTP-modified polypeptide comprising GLP-1/Glucagon receptor agonist is administered in an amount effective to bring circulating GLP-1/Glucagon receptor agonist activity to 20-30 IU/dL in a subject. In another embodiment, the CTP-modified polypeptide comprising GLP-1/Glucagon receptor agonist is administered in an amount effective to bring circulating GLP-1/Glucagon receptor agonist activity to 25-50 IU/dL in a subject. In another embodiment, the CTP-modified polypeptide comprising GLP-1/Glucagon receptor agonist is administered in an amount effective to bring circulating GLP-1/Glucagon receptor agonist activity to 50-100 IU/dL in a subject. In another embodiment, the CTP-modified polypeptide comprising GLP-1/Glucagon receptor agonist is administered in an amount effective to bring circulating GLP-1/Glucagon receptor agonist activity to 100-200 IU/dL in a subject. In another embodiment, the CTP-modified polypeptide comprising GLP-1/Glucagon receptor agonist is administered in an amount effective to bring circulating GLP-1/Glucagon receptor agonist activity to 10-50 IU/dL in a subject. In another embodiment, the CTP-modified polypeptide comprising GLP-1/Glucagon receptor agonist is administered in an amount effective to bring circulating GLP-1/Glucagon receptor agonist activity to 20-100 IU/dL in a subject.

In one embodiment, the CTP-modified GLP-1/Glucagon receptor agonist is administered to a subject on a weekly basis. In another embodiment, the CTP-modified GLP-1/Glucagon receptor agonist is administered to a subject twice a week. In another embodiment, the CTP-modified GLP-1/Glucagon receptor agonist is administered to a subject on a fortnightly (once every two weeks) basis. In another embodiment, the CTP-modified GLP-1/Glucagon receptor agonist is administered to a subject twice a month. In another embodiment, the CTP-modified GLP-1/Glucagon receptor agonist is administered to a subject once a month. In another embodiment, the CTP-modified GLP-1/Glucagon receptor agonist is administered to a subject on a daily basis. In another embodiment, the CTP-modified GLP-1/Glucagon receptor agonist is administered to a subject every two days.

In another embodiment, a polypeptide comprising a GLP-1/Glucagon receptor agonist and at least one CTP unit is administered to a subject once every three days. In another embodiment, a polypeptide comprising a GLP-1/Glucagon receptor agonist and at least one CTP unit is administered to a subject once every four days. In another embodiment, a polypeptide comprising a GLP-1/Glucagon receptor agonist and at least one CTP unit is administered to a subject once every five days. In another embodiment, a polypeptide comprising a GLP-1/Glucagon receptor agonist and at least one CTP unit is administered to a subject once every six days. In another embodiment, a polypeptide comprising a GLP-1/Glucagon receptor agonist and at least one CTP unit is administered to a subject once every 7-14 days. In another embodiment, a polypeptide comprising a GLP-1/Glucagon receptor agonist and at least one CTP unit is administered to a subject once every 10-20 days. In another embodiment, a polypeptide comprising a GLP-1/Glucagon receptor agonist and at least one CTP unit is administered to a subject once every 5-15 days. In another embodiment, a polypeptide comprising a GLP-1/Glucagon receptor agonist and at least one CTP unit is administered to a subject once every 15-30 days.

In another embodiment, the methods of the invention include increasing the compliance in the use of GLP-1/Glucagon receptor agonist therapy, comprising providing to a subject in need thereof, a polypeptide comprising a GLP-1/Glucagon receptor agonist and at least one chorionic gonadotrophin carboxy terminal peptide (CTP) attached to the carboxy terminus of the GLP-1/Glucagon receptor agonist, thereby increasing compliance in the use of GLP-1/Glucagon receptor agonist therapy.

In another embodiment, the methods of the invention include increasing the compliance of patients afflicted with chronic illnesses that are in need of a GLP-1/Glucagon receptor agonist therapy. In another embodiment, the methods of the invention enable reduction in the dosing frequency of a GLP-1/Glucagon receptor agonist by modifying the GLP-1/Glucagon receptor agonist with CTPs as described hereinabove.

In another embodiment, the term compliance comprises adherence. In another embodiment, the methods of the invention include increasing the compliance of patients in need of a GLP-1/Glucagon receptor agonist therapy by reducing the frequency of administration of the GLP-1/Glucagon receptor agonist. In another embodiment, reduction in the frequency of administration of the GLP-1/Glucagon receptor agonist is achieved due to the CTP modifications which render the CTP-modified GLP-1/Glucagon receptor agonist more stable. In another embodiment, reduction in the frequency of administration of the GLP-1/Glucagon receptor agonist is achieved as a result of increasing T½ of the GLP-1/Glucagon receptor agonist. In another embodiment, reduction in the frequency of administration of the GLP-1/Glucagon receptor agonist is achieved as a result of increasing the clearance time or reducing the clearance rate of the GLP-1/Glucagon receptor agonist.

In another embodiment, the present invention provides a method of reducing the clearance rate of GLP-1/Glucagon receptor agonist, comprising the step of at least one chorionic gonadotrophin carboxy terminal peptides (CTPs) to the amino or carboxy terminus of GLP-1/Glucagon receptor agonist, thereby reducing the clearance rate of GLP-1/Glucagon receptor agonist.

In another embodiment, reduction in the frequency of administration of the GLP-1/Glucagon receptor agonist is achieved as a result of increasing the AUC measure of the GLP-1/Glucagon receptor agonist.

Oral administration, in one embodiment, comprises a unit dosage form comprising tablets, capsules, lozenges, chewable tablets, suspensions, emulsions and the like. Such unit dosage forms comprise a safe and effective amount of the desired GLP-1/Glucagon receptor agonist of the invention, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In another embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In another embodiment, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 10%.

In one embodiment, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In another embodiment, the compositions comprise from about 0.001% to about 10.0% w/v of a subject compound, more preferably from about 00.1% to about 2.0, which is used for systemic delivery of the compounds by the intranasal route.

In another embodiment, a polypeptide comprising a GLP-1/Glucagon receptor agonist and at least one CTP unit is injected into the muscle (intramuscular injection). In another embodiment, a polypeptide comprising a GLP-1/Glucagon receptor agonist and at least one CTP unit is injected below the skin (subcutaneous injection). In another embodiment, a polypeptide comprising a GLP-1/Glucagon receptor agonist and at least one CTP unit is injected into the muscle. In another embodiment, a polypeptide comprising a GLP-1/Glucagon receptor agonist and at least one CTP unit is injected into the skin. In another embodiment, a GLP-1/Glucagon receptor agonist as described herein is administered via systemic administration. In another embodiment, a GLP-1/Glucagon receptor agonist as described herein is administered by intravenous injection. In another embodiment, administration can be parenteral, pulmonary, oral, topical, intradermal, intramuscular, intraperitoneal, intravenous, subcutaneous, intranasal, transnasal, intraocular, ophthalmic, epidural, buccal, rectal, transmucosal, intestinal or parenteral delivery, including intramedullary injections as well as intrathecal or direct intraventricular administration.

In another embodiment, the preparation is administered in a local rather than systemic manner, for example, via injection of the preparation directly into a specific region of a patient's body.

In one embodiment, the route of administration may be enteral. In another embodiment, the route may be conjunctival, transdermal, intradermal, intra-arterial, vaginal, rectal, intratumoral, parcanceral, transmucosal, intramuscular, intravascular, intraventricular, intracranial, intra-nasal, sublingual, or a combination thereof.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, and in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in a conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables of the invention are formulated in aqueous solutions. In one embodiment, injectables of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other active ingredients. The compositions can be used as sprays, mists, drops, and the like.

In one embodiment, pharmaceutical compositions for parenteral administration include aqueous solutions of the active preparation in water-soluble form. Additionally, suspensions of the active ingredients can be prepared as appropriate oil or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; J. E. Diederichs and al., Pharm./nd. 56 (1994) 267-275).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In another embodiment, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, pharmaceutical compositions suitable for use in context of the present invention include compositions wherein the active ingredients are contained in an amount effective to achieve the intended purpose. In another embodiment, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

Preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will be dependent on the subject being treated, the severity of the affliction, the manner of administration, the judgment of the prescribing physician, etc.

In one embodiment, compositions including the preparation of the present invention formulated in a compatible pharmaceutical carrier are also prepared, placed in an appropriate container, and labeled for treatment of an indicated condition.

In another embodiment, a GLP-1/Glucagon receptor agonist or a variant (CTP-modified) form thereof, as described herein, is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized GLP-1/Glucagon receptor agonist as described in sterile water for injection. In another embodiment, a pharmaceutical composition comprises a lyophilized GLP-1/Glucagon receptor agonist as described in sterile PBS for injection. In another embodiment, a pharmaceutical composition comprises a lyophilized GLP-1/Glucagon receptor agonist as described in sterile 0.9% NaCl for injection.

In another embodiment, the pharmaceutical composition comprises a CTP-modified GLP-1/Glucagon receptor agonist as described herein and complex carriers such as human serum albumin, polyols, sugars, and anionic surface active stabilizing agents. In another embodiment, the pharmaceutical composition comprises a CTP-modified GLP-1/Glucagon receptor agonist as described herein and lactobionic acid and an acetate/glycine buffer. In another embodiment, the pharmaceutical composition comprises a CTP-modified GLP-1/Glucagon receptor agonist as described herein and amino acids, such as arginine or glutamate that increase the solubility of interferon compositions in water. In another embodiment, the pharmaceutical composition comprises a lyophilized CTP-modified GLP-1/Glucagon receptor agonist as described herein and glycine or human serum albumin (HSA), a buffer (e.g. acetate) and an isotonic agent (e.g NaCl). In another embodiment, the pharmaceutical composition comprises a lyophilized CTP-modified GLP-1/Glucagon receptor agonist as described herein and phosphate buffer, glycine and HSA.

In another embodiment, the pharmaceutical composition comprising a CTP-modified GLP-1/Glucagon receptor agonist as described herein is stabilized when placed in buffered solutions having a pH between about 4 and 7.2. In another embodiment, the pharmaceutical composition comprising a CTP-modified GLP-1/Glucagon receptor agonist is in a buffered solution having a pH between about 4 and 8.5. In another embodiment, the pharmaceutical composition comprising a CTP-modified GLP-1/Glucagon receptor agonist is in a buffered solution having a pH between about 6 and 7. In another embodiment, the pharmaceutical composition comprising a CTP-modified GLP-1/Glucagon receptor agonist is in a buffered solution having a pH of about 6.5. In another embodiment, the pharmaceutical composition comprising a CTP-modified GLP-1/Glucagon receptor agonist as described herein is stabilized with an amino acid as a stabilizing agent and in some cases a salt (if the amino acid does not contain a charged side chain).

In another embodiment, the pharmaceutical composition comprising a CTP-modified GLP-1/Glucagon receptor agonist as described herein is a liquid composition comprising a stabilizing agent at between about 0.3% and 5% by weight which is an amino acid.

In another embodiment, the pharmaceutical composition comprising a CTP-modified GLP-1/Glucagon receptor agonist as described herein provides dosing accuracy and product safety. In another embodiment, the pharmaceutical composition comprising a CTP-modified GLP-1/Glucagon receptor agonist as described herein provides a biologically active, stable liquid formulation for use in injectable applications. In another embodiment, the pharmaceutical composition comprises a non-lyophilized CTP-modified GLP-1/Glucagon receptor agonist as described herein.

In another embodiment, the pharmaceutical composition comprising a CTP-modified GLP-1/Glucagon receptor agonist provided herein provides a liquid formulation permitting storage for a long period of time in a liquid state facilitating storage and shipping prior to administration.

In another embodiment, the pharmaceutical composition comprising a CTP-modified GLP-1/Glucagon receptor agonist provided herein comprises solid lipids as matrix material. In another embodiment, the injectable pharmaceutical composition comprising a CTP-modified GLP-1/Glucagon receptor agonist as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a CTP-modified GLP-1/Glucagon receptor agonist as described herein comprises polymeric microparticles. In another embodiment, the pharmaceutical composition comprising a CTP-modified GLP-1/Glucagon receptor agonist as described herein comprises nanoparticles. In another embodiment, the pharmaceutical composition comprising a CTP-modified GLP-1/Glucagon receptor agonist as described herein comprises liposomes. In another embodiment, the pharmaceutical composition comprising a CTP-modified GLP-1/Glucagon receptor agonist as described herein comprises lipid emulsion. In another embodiment, the pharmaceutical composition comprising a CTP-modified GLP-1/Glucagon receptor agonist as described herein comprises microspheres. In another embodiment, the pharmaceutical composition comprising a CTP-modified GLP-1/Glucagon receptor agonist as described herein comprises lipid nanoparticles. In another embodiment, the pharmaceutical composition comprising a CTP-modified GLP-1/Glucagon receptor agonist as described herein comprises lipid nanoparticles comprising amphiphilic lipids. In another embodiment, the pharmaceutical composition comprising a CTP-modified GLP-1/Glucagon receptor agonist as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the GLP-1/Glucagon receptor agonist of the present invention can be provided to the individual with additional active agents to achieve an improved therapeutic effect as compared to treatment with each agent by itself. In another embodiment, measures (e.g., dosing and selection of the complementary agent) are taken to avoid adverse side effects which are associated with combination therapies.

In one embodiment, the term "about", means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

It is to be understood that in one embodiment, methods of treatment and prevention of the CTP-modified polypeptide as described herein may be substituted by uses of the CTP-modified polypeptide as described herein for accomplishing the methods for treatment and prevention as described herein and/or uses of the CTP-modified polypeptide as described herein in the preparation of a medicament for accomplishing the methods for treatment and prevention as described herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Plasmid Construction

Seven OXM plasmids were constructed in eukaryotic expression vector (pCI-dhfrr) based on the OXM amino acid sequence (accession #NP_002045) and the CTP amino acid sequence (accession #NP_149032).

A schematic presentation of these plasmids is shown in Table 1. A detailed description of plasmids construction follows.

TABLE 1

Schematic description of plasmids

| | Plasmid variant description | Nucleic Acid Sequence |
|---|---|---|
| 1 | OXM-CTP-CTP | SEQ ID NO: 20 |
| 2 | CTP-OXM-CTP | SEQ ID NO: 8 |
| 3 | CTP-CTP-OXM | SEQ ID NO: 22 |
| 4 | CTP-OXM-CTP-CTP | SEQ ID NO: 14 |
| 5 | OXM-CTP-CTP-CTP | SEQ ID NO: 24 |
| 6 | OXM-CTP-CTP-CTP-CTP | SEQ ID NO: 26 |
| 7 | OXM-CTP-CTP-CTP-CTP-CTP | SEQ ID NO: 28 |

A nucleic acid sequence of the OXM variant CTP-OXM-CTP (0.5 C CTP-OXM-CTP, GenArt, GA #0804377) was synthesized after a codon usage optimization for DG44 expression system. An XbaI-NotI fragment containing 0.5 C CTP-OXM-CTP sequence was isolated. The fragment was inserted into the eukaryotic expression vector pCI-dhfr to yield the 601-0-p142-1 clone.

Construction of CTP-OXM-CTP

The following primers were used in order to synthesize 601-6-p149-1 (CTP-OXM-CTP)

```
Primer 25
                                   (SEQ ID NO: 4)
5' CTCTAGAGGACATGGCCAC 3'.

Primer 85R
                                   (SEQ ID NO: 5)
5' CTGGCTGTGCTGGGGCAGAATGGGTGT 3'.
```

-continued

```
Primer 86
                                   (SEQ ID NO: 6)
5' CCCCAGCACAGCCAGGG 3'.

Primer 74R
                                   (SEQ ID NO: 7)
5' GCGGCCGCATCCAGACCT 3'.
```

Three PCR reactions were performed. The first reaction was conducted with primer 25 and primer 85R and plasmid DNA of 402-3-p81-4 (CTP-hGH-CTP-CTP) as a template; as a result of the PCR amplification, a ~181 bp product was formed. The second reaction was conducted with primer 86 and primer 74R and plasmid DNA of 601-0-p142-1 (0.5 C CTP-OXM-CTP) as a template; as a result of the PCR amplification, a ~224 bp product was formed. The last reaction was conducted with primers 25 and 74R and a mixture of the products of the previous two reactions as a template; as a result of the PCR amplification, a ~391 bp product was formed and ligated into TA cloning vector (Invitrogen, catalog K2000-01). An XbaI-NotI fragment containing CTP-OXM-CTP sequence was isolated. The fragment was inserted into our eukaryotic expression vector pCI-dhfr to yield 601-6-p149-1 clone.

The nucleic acid sequence encoding CTP-OXM-CTP is as follows:

```
                                   (SEQ ID NO: 8)
tctagaggacatggccaccggcagcaggaccagcctgctgctggccttc

ggcctgctgtgcctgccatggctgcaggagggcagcgccagctcttctt

ctaaggctccacccccatctctgcccagccccagcagactgccgggccc

cagcgacacacccattctgccccagcacagccagggcaccttcaccagc

gactacagcaagtacctggacagcagaagggcccaggacttcgtccagt

ggctgatgaacaccaagaggaacaggaacaacatcgcttcctctagctc

caaggcccctccaccctctctgcctagcccctctcggctgcctggccca

tccgacacaccaatcctgccacagtgatgaaggtctggatgcggccgc.
```

The amino acid sequence encoding CTP-OXM-CTP is as follows:

```
                                   (SEQ ID NO: 9)
MATGSRTSLLLAFGLLCLPWLQEGSASSSSKAPPPSLPSPSRLPGPSDT

PILPQHSQGTFTSDYSKYLDSRRAQDFVQWLMNTKRNRNNIASSSSKAP

PPSLPSPSRLPGPSDTPILPQ.
```

Construction of CTP-OXM-CTP-CTP

The following primers were used in order to synthesize 601-3-p158-2 (CTP-OXM-CTP-CTP):

Primer 25 5' CTCTAGAGGACATGGCCAC 3' (contains the restriction site of XbaI) (SEQ ID NO: 10).

Primer $87^R$ 5' GCTGGAGCTAGCGATGTTGTTCCTGTTCC 3' (contains the 3' end of OXM and the 5' end of CTP) (SEQ ID NO: 11).

Primer 88 5' ACATCGCTAGCTCCAGCAGCAAGGCC 3' (contains the 3' end of OXM and the 5' end of CTP) (SEQ ID NO: 12).

Primer $74^R$ 5' GCGGCCGCATCCAGACCT 3' (contains the restriction site of NotI) (SEQ ID NO: 13).

Three PCR reactions were performed. The first reaction was conducted with primer 25 and primer 87R and plasmid DNA of 601-6-p149-1 (CTP-OXM-CTP-CTP) as a template; as a result of the PCR amplification, a ~290 bp product was formed. The second reaction was conducted with primer 88 and primer 74R and plasmid DNA of 402-3-p81-4 (CTP-hGH-CTP-CTP) as a template; as a result of the PCR amplification, a ~200 bp product was formed. The last reaction was conducted with primers 25 and 74R and a mixture of the products of the previous two reactions as a template; as a result of the PCR amplification, a ~450 bp product was formed and ligated into TA cloning vector (Invitrogen, catalog K2000-01). XbaI-NotI fragment containing CTP-OXM-CTP-CTP sequence was isolated. The fragment was inserted in to our eukaryotic expression vector pCI-dhfr to yield 601-3-p158-2 clone.

The nucleic acid sequence encoding CTP-OXM-CTP-CTP is as follows:

```
                                        (SEQ ID NO: 14)
tctagaggacatggccaccggcagcaggaccagcctgctgctggccttc

ggcctgctgtgcctgccatggctgcaggagggcagcgccagctcttctt

ctaaggctccacccccatctctgcccagccccagcagactgccgggccc

cagcgacacacccattctgccccagcacagccagggcaccttcaccagc

gactacagcaagtacctggacagcagaagggcccaggacttcgtccagt

ggctgatgaacaccaagaggaacaggaacaacatcgctagctccagcag

caaggcccctcccccgagcctgccctccccaagcaggctgcctgggccc

tccgacacaccaatcctgccacagagcagctcctctaaggcccctcctc

catccctgccatcccccctcccggctgcctggcccctctgacacccctat

cctgcctcagtgatgaaggtctggatgcggccgc.
```

The amino acid sequence encoding CTP-OXM-CTP-CTP is as follows:

```
                                        (SEQ ID NO: 15)
MATGSRTSLLLAFGLLCLPWLQEGSASSSSKAPPPSLPSPSRLPGPSDT

PILPQHSQGTFTSDYSKYLDSRRAQDFVQWLMNTKRNRNNIASSSSKAP

PPSLPSPSRLPGPSDTPILPQSSSSKAPPPSLPSPSRLPGPSDTPILPQ.
```

Construction of OXM-CTP-CTP

The following primers were used in order to synthesize 601-2-p160-2 (OXM-CTP-CTP):

Primer 75 5' CTCCCAGTTCAATTACAGCT 3' (contains sequence of pCI-dhfr before XbaI restriction site) (SEQ ID NO: 16).

Primer $89^R$ 5' GCTGTGAGCGCTGCCCTCCTGCAG 3' (contains 5' end of OXM) (SEQ ID NO: 17).

Primer 90 5' GCGCTCACAGCCAGGGCACCTTC 3' (contains the 5' end of OXM) (SEQ ID NO: 18).

Primer $74^R$ 5' GCGGCCGCATCCAGACCT 3' (contains the restriction site of NotI) (SEQ ID NO: 19).

Three PCR reactions were performed. The first reaction was conducted with primer 75 and primer 89R and plasmid DNA of 601-0-p142-1 (0.5 C CTP-OXM-CTP) as a template; as a result of the PCR amplification, a ~175 bp product was formed. The second reaction was conducted with primer 90 and primer 74R and plasmid DNA of 601-3-p158-2 (CTP-OXM-CTP-CTP) as a template; as a result of the PCR amplification, a ~200 bp product was formed. The last reaction was conducted with primers 25 and 74R and a mixture of the products of the previous two reactions as a template; as a result of the PCR amplification, a ~391 bp product was formed and ligated into TA cloning vector (Invitrogen, catalog K2000-01). XbaI-NotI fragment containing OXM-CTP-CTP sequence was isolated. The fragment was inserted into our eukaryotic expression vector pCI-dhfr to yield the 601-2-p160-2 clone.

The nucleic acid sequence encoding OXM-CTP-CTP is as follows:

```
                                        (SEQ ID NO: 20)
tctagaggacatggccacagggagcaggaccagcctgctgctggctttc

ggcctgctgtgtctgccatggctgcaggagggcagcgctcacagccagg

gcaccttcaccagcgactacagcaagtacctggacagcagaagggccca

ggacttcgtccagtggctgatgaacaccaagaggaacaggaacaacatc

gctagctccagcagcaaggcccctcccccgagcctgccctccccaagca

ggctgcctgggccctccgacacaccaatcctgccacagagcagctcctc

taaggcccctcctccatccctgccatcccccctcccggctgcctggcccc

tctgacacccctatcctgcctcagtgatgaaggtctggatgcggccgc
```

The amino acid sequence encoding OXM-CTP-CTP is as follows:

```
                                        (SEQ ID NO: 21)
LEDMATGSRTSLLLAFGLLCLPWLQEGSAHSQGTFTSDYSKYLDSRRAQ

DFVQWLMNTKRNRNNIASSSSKAPPPSLPSPSRLPGPSDTPILPQSSSS

KAPPPSLPSPSRLPGPSDTPILPQ
```

Construction of CTP-CTP-OXM

A nucleic acid sequence of OXM variant (CTPx2-OXM, GenArt, GA #1067101) was synthesized after a codon usage optimization for DG44 expression system. The fragment was inserted in to Excellgene eukaryotic expression vector to yield p162 clone.

The nucleic acid sequence encoding CTPx2-OXM is as follows:

```
                                        (SEQ ID NO: 22)
ctatagggcgaattgaaggaaggccgtcaaggccgcatgagctctctag

aggacatggccaccggcagcaggaccagcctgctgctggccttcggcct

gctgtgcctgccatggctgcaggagggcagcgccagctccagcagcaag

gcccctcccccgagcctgccctccccaagcaggctgcctgggccctccg

acacaccaatcctgccacagagcagctcctctaaggcccctcctccatc

cctgccatcccccctcccggctgcctggcccctctgacacccctatcctg

cctcagcacagccagggcaccttcaccagcgactacagcaagtacctgg

acagcagaagggcccaggacttcgtccagtggctgatgaacaccaagag

gaacaggaacaacatcgcttgatgaaggtctggatgcggccgcggtacc

ctgggcctcatgggccttcctttcactgcccgctttccag.
```

The amino acid sequence encoding CTPx2-OXM is as follows:

```
                                        (SEQ ID NO: 23)
M A T G S R T S L L L A F G L L C L P W L Q E G S

A S S S S K A P P P S L P S P S R L P G P S D T P
```

-continued

I L P Q S S S S K A P P P S L P S P S R L P G P S

D T P I L P Q H S Q G T F T S D Y S K Y L D S R R

A Q D F V Q W L M N T K R N R N N I A * * R S G C

G R G T L G L M G L P F T A R F P.

Construction of OXM-CTPx3:

A nucleic acid sequence of OXM variant (OXM-CTPx3, GenArt, GA #1017864) was synthesized after a codon usage optimization for DG44 expression system. XbaI-NotI fragment containing OXM-CTPx3 sequence was isolated. The fragment was inserted in to our eukaryotic expression vector pCI-dhfr to yield pCI-dhfr-OXM-ctpx3-p216-4 clone.

The nucleic acid sequence encoding OXM-CTPx3 is as follows:

(SEQ ID NO: 24)

tctagactcgagcgatcgccatggccaccggctctaggacctccctgct gctggccttcggcctgctgtgcctgccctggctgcaggaaggcagcgct cactcccagggcaccttcacctccgactactccaagtacctggactctc ggagagcccaggacttcgtgcagtggctgatgaacaccaagcggaaccg gaacaatatcgcctcctcaagctccaaggcacctccaccttccctgcct agcccttccagactccctgggcccagtgacacccctatcctgcctcagt ccagctccagcaaggccccacccccctagcctgccttctccttctcggct gcctggccccagcgatactccaattctgccccagtcctccagcagtaag gctccccctccatctctgccatcccccagcagactgccaggcccttctg atacacccatcctcccacagtgatgaggatccgcggccgc.

The amino acid sequence encoding OXM-CTPx3 is as follows:

(SEQ ID NO: 25)

M A T G S R T S L L L A F G L L C L P W L Q E G S

A H S Q G T F T S D Y S K Y L D S R R A Q D F V Q

W L M N T K R N R N N I A S S S S K A P P P S L P

S P S R L P G P S D T P I L P Q S S S S K A P P P

S L P S P S R L P G P S D T P I L P Q S S S S K A

P P P S L P S P S R L P G P S D T P I L P Q * *.

Construction of OXM-CTPx4:

A nucleic acid sequence of OXM variant (OXM-CTPx4, GenArt, GA #1115769) was synthesized after a codon usage optimization for DG44 expression system. XbaI-NotI fragment containing OXM-CTPx4 sequence was isolated. The fragment was inserted in to the eukaryotic expression vector pCI-dhfr to yield pCI-dhfr-OXM-ctpx4-p254-3 clone.

The nucleic acid sequence encoding OXM-CTPx4 is as follows:

(SEQ ID NO: 26)

tctagactcgagcgatcgccatggctaccggctccagaacctctctgct gctggccttcggcctgctgtgtctgccttggctgcaagagggcagcgct cattcccagggcaccttcacctccgactactccaagtacctggactctc -continued gcagagcccaggacttcgtgcagtggctgatgaacaccaagcggaaccg gaacaatatcgcctcctccagctccaaggcccctcctccatctctgcca tcccccagtagactgcctgggccctctgacacccctatcctgcctcagt ccagctcctctaaggccccaccaccttccctgcctagcccttcaagact gccaggccctagcgatacaccaattctgccccagtcctccagcagcaag gctcccccacctagcctgccttctccatcaaggctgcctggcccatccg ataccccaattttgcctcagagcagctctagcaaggcacctccccccag tctgccctctccaagcagactccctggcccttcagacactcccattctg ccacagtgatgaggatccgcggccgc The amino acid sequence encoding OXM-CTPx4 is as follows:

(SEQ ID NO: 27)

M A T G S R T S L L L A F G L L C L P W L Q E G S

A H S Q G T F T S D Y S K Y L D S R R A Q D F V Q

W L M N T K R N R N N I A S S S S K A P P P S L P

S P S R L P G P S D T P I L P Q S S S S K A P P P

S L P S P S R L P G P S D T P I L P Q S S S S K A

P P P S L P S P S R L P G P S D T P I L P Q S S S

S K A P P P S L P S P S R L P G P S D T P I L P

Q * *.

Construction of OXM-CTPx5:

A nucleic acid sequence of OXM variant (OXM-CTPx5, GenArt, GA #1115770) was synthesized after a codon usage optimization for DG44 expression system. XbaI-NotI fragment containing OXM-CTPx5 sequence was isolated. The fragment was inserted in to the eukaryotic expression vector pCI-dhfr to yield pCI-dhfr-OXM-ctpx5-p255-1 clone.

The nucleic acid sequence encoding OXM-CTPx5 is as follows:

(SEQ ID NO: 28)

ctctagactcgagcgatcgccatggctaccggctccagaacctctctgc tgctggccttcggcctgctgtgtctgccttggctgcaagagggcagcgc tcattcccagggcaccttcacctccgactactccaagtacctggactct cgcagagcacaggacttcgtgcagtggctgatgaacaccaagcggaacc ggaacaatatcgcctcctccagctccaaggcccctcctccatctctgcc atcccccagtagactgcctgggccctctgacacccctatcctgcctcag tccagctcctctaaggctccaccaccttccctgcctagcccttcaagac tgccaggccctagcgatacaccaattctgccccagtcctccagcagcaa ggctcccccacctagcctgccttctccatcaaggctgcctggcccatcc gataccccaattttgcctcagagcagctctagcaaggcacctcccccca gtctgccctctccaagcagactccctggcccttcagacactccaatcct cccacagtcctctagctctaaagctccacctcccagcctgcccagccct agtagactccccggaccttctgataccccatcttgccccagtgatgag gatccgcggccgc.

The amino acid sequence encoding OXM-CTPx5 is as follows:

```
                                        (SEQ ID NO: 29)
M A T G S R T S L L L A F G L L C L P W L Q E G S

A H S Q G T F T S D Y S K Y L D S R R A Q D F V Q

W L M N T K R N R N N I A S S S S K A P P P S L P

S P S R L P G P S D T P I L P Q S S S S K A P P P

S L P S P S R L P G P S D T P I L P Q S S S S K A

P P P S L P S P S R L P G P S D T P I L P Q S S S

S K A P P P S L P S P S R L P G P S D T P I L P Q

S S S S K A P P P S L P S P S R L P G P S D T P I

L P Q * *.
```

Expression, Purification and Characterization of OXM-CTP Variants

All seven variants of OXM-CTPs were transiently expressed and produced in XLG's CHO-Express cell line (Excellgene Company, Switzerland). Concentration levels of OXM-CTPs harvests were determined using an OXM ELISA kit (Bachem Cat#S-1393.0001). The harvest was purified using a DEAE column, followed by a Jacalin column as a second purification step. The final fractions were dialyzed against 10 mM buffer citrate, 147 mM NaCl, pH 6. The concentration of purified variants was determined by absorbance at 280 nm using extinction coefficient of 1.9=1 mg/ml. 1.9 is the extinction coefficient that theoretically was calculated for the OXM peptide. Since CTP peptide does not absorb at 280 nm, the same extinction coefficient was applied for OXM-CTP variants. OXM native peptide was chemically synthesized (Almac Company, Ireland), and its peptide content was determined by amino acid analysis.

Pharmacokinetic (PK) Profile of OXM-CTP Variants

The pharmacokinetic profiles of the OXM peptide and OXM-CTP variants were assessed as follows. Male Sprague-Dawley (SD)-1 rats were administered subcutaneously (SC) or intravenously (IV) with a single dose of native OXM (n=6, 230 μg/kg), of variants CTP-OXM-CTP, CTP-OXM-CTP-CTP, OXM-CTP-CTP and CTP-CTP-OXM (n=6, 230 μg/kg) or variants #OXM-CTP-CTP-CTP, OXM-CTP-CTP-CTP-CTP, OXM-CTP-CTP-CTP-CTP-CTP (n=6, 153 μg/kg). Cohorts of 3 animals per group were bled at alternating time points. OXM serum concentration was analyzed using commercial ELISA kit (Bachem, Cat#S-1393.0001). The study design is summarized in Table 2. The study was divided into 3 sequential experiments, Experiment #1 (Groups 1-4), Experiment #2 (Groups 5-9) and Experiment #3 (Groups 10-13).

TABLE 2

Summary of the PK study design.
IPGTT study in C57BL/6 mice

| Group # | Test Article Variant # | No. of animals/ group/ timepoint | Dose Route | Gender | Dose Level of OXM (μg/rat) | Dose Level of OXM (μg/kg) | Time-Points (hours post-dose) |
|---|---|---|---|---|---|---|---|
| 1 | OXM | 6/3 | IV | Male | 34 | 230 | 0 (Pre-dose), 5 min, 15 min, 25 min, 35 min, 45 min, 60 min, 75 min, 1.5 h, 2 h |
| 2 | CTP-OXM-CTP | 6/3 | IV | Male | 34 | 230 | 0 (Pre-dose), 10 min, 30 min, 1 h, 2 h, 3 h, 4 h, 6 h, 8 h, 24 h, 36 h, 48 h |
| 3 | CTP-OXM-CTP-CTP | 6/3 | IV | Male | 34 | 230 | 0 (Pre-dose), 10 min, 30 min, 1 h, 2 h, 3 h, 4 h, 6 h, 8 h, 24 h, 36 h, 48 h |
| 4 | CTP-CTP-OXM | 6/3 | IV | Male | 34 | 230 | 0 (Pre-dose), 10 min, 30 min, 1 h, 2 h, 3 h, 4 h, 6 h, 8 h, 24 h, 36 h, 48 h |
| 5 | OXM | 6/3 | SC | Male | 34 | 230 | 0 (Pre-dose), 5 min, 15 min, 25 min, 35 min, 45 min, 60 min 75 min, 1.5 h, 2 h |
| 6 | CTP-OXM-CTP | 6/3 | SC | Male | 34 | 230 | 0 (Pre-dose), 10 min, 30 min, 1 h, 2 h, 4 h, 6 h, 8 h, 24 h, 36 h, 2 d, 3 d |
| 7 | CTP-OXM-CTP-CTP | 6/3 | SC | Male | 34 | 230 | 0 (Pre-dose), 10 min, 30 min, 1 h, 2 h, 4 h, 6 h, 8 h, 24 h, 36 h, 2 d, 3 d |
| 8 | CTP-CTP-OXM | 6/3 | SC | Male | 34 | 230 | 0 (Pre-dose), 10 min, 30 min, 1 h, 2 h, 4 h, 6 h, 8 h, 24 h, 36 h, 2 d, 3 d |
| 9 | OXM-CTP-CTP | 6/3 | SC | Male | 34 | 230 | 0 (Pre-dose), 10 min, 30 min, 1 h, 2 h, 4 h, 6 h, 8 h, 24 h, 36 h, 2 d, 3 d |
| 10 | OXM | 6/3 | SC | Male | 34 | 230 | 0 (Pre-dose), 5 min, 15 min, 25 min, 35 min, 45 min, 60 min 75 min, 1.5 h, 2 h |
| 11 | OXM-CTPX3 | 6/3 | SC | Male | 23 | 153 | 0 (Pre-dose), 10 min, 30 min, 1 h, 2 h, 4 h, 6 h, 8 h, 24 h, 36 h, 2 d, 3 d, 4 d |

TABLE 2-continued

| Summary of the PK study design. IPGTT study in C57BL/6 mice | | | | | | | |
|---|---|---|---|---|---|---|---|
| Group # | Test Article Variant # | No. of animals/ group/ timepoint | Dose Route | Gender | Dose Level of OXM (μg/rat) | Dose Level of OXM (μg/kg) | Time-Points (hours post-dose) |
| 12 | OXM-CTPX4 | 6/3 | SC | Male | 23 | 153 | 0 (Pre-dose), 10 min, 30 min, 1 h, 2 h, 4 h, 6 h, 8 h, 24 h, 36 h, 2 d, 3 d, 4 d |
| 13 | OXM-CTPX5 | 6/3 | SC | Male | 23 | 153 | 0 (Pre-dose), 10 min, 30 min, 1 h, 2 h, 4 h, 6 h, 8 h, 24 h, 36 h, 2 d, 3 d, 4 d |

Overnight-fasted mice were measured for glucose (pre-dose glucose). Immediately after, they were IP injected with one of the test articles. Fifteen or 120 min post injection, glucose levels were measured (zero time for glucose) followed by glucose administration via IP injection (1.5 g/kg). Additional glucose measurement at 10, 20, 30, 60, 90, 120 and 180 min were performed. Blood glucose level were measured by tail vein sampling using a handheld glucometer.

Food Intake Study in C57BL/6 Mice

At least one week before injection, mice were weighed and were transferred to a mini cage for acclimatization, (one mouse per cage). During the acclimatization period, they were handled daily and received two injections of vehicle to minimize stress during the study period. The day before the experiment, the mice were fasted. Seventeen hours after fasting, at the early light phase (900-1000 h), the mice were weighed again (prior to the IP injection) followed by a single IP injection of 1700 nmol/kg (10 μl/1 g mice) of OXM peptide or OXM-CTP variants OXM-CTPX3, OXM-CTPX4 and OXM-CTPX5. After injection, the mice were returned to their home cages (1 mouse per cage), and provided with a pre-weighed amount of chow. Food intake were measured 0, 1, 2, 4, 6, 8, 21, 32 and 44, 55, 68, 80, 93 and 141 h post injection by weighing the chow. At the end of experiment, rats were weighed again.

RESULTS

Example 1

Construction of CTP-Modified OXM

By genetic engineering, CTP peptide cDNA was fused to human OXM cDNA, generating seven different OXM-CTP variant as detailed in Table 1. The nucleotide sequences of the plasmids were verified, and the plasmids were transiently transfected into XLG's CHO-Express cell line (Excellgene Company, Switzerland). The OXM-CTP variants were secreted into the growth medium, harvests were collected and OXM-CTPs levels were determined.

Example 2

Expression, Purification and Characterization of OXM-CTP Variants

The production media (harvests) were measured for secretion level of OXM-CTP variants. The secretion levels are summarized in Table 3. The secretion levels obtained were high considering the standard transient transfection expression levels of recombinant peptides.

TABLE 3

| Summary of OXM-CTPs secretion level. | | | | | | | |
|---|---|---|---|---|---|---|---|
| Variant | CTP-OXM-CTP | CTP-OXM-CTP-CTP | OXM-CTP-CTP | CTP-CTP-OXM | OXM-CTPX4 | OXM-CTPX4 | OXM-CTPX5 |
| Harvest concentration (μg/ml) | 31.1 | 15.3 | 3.3 | 51.9 | 13.9 | 15.3 | 14.4 |

Figure 1B:
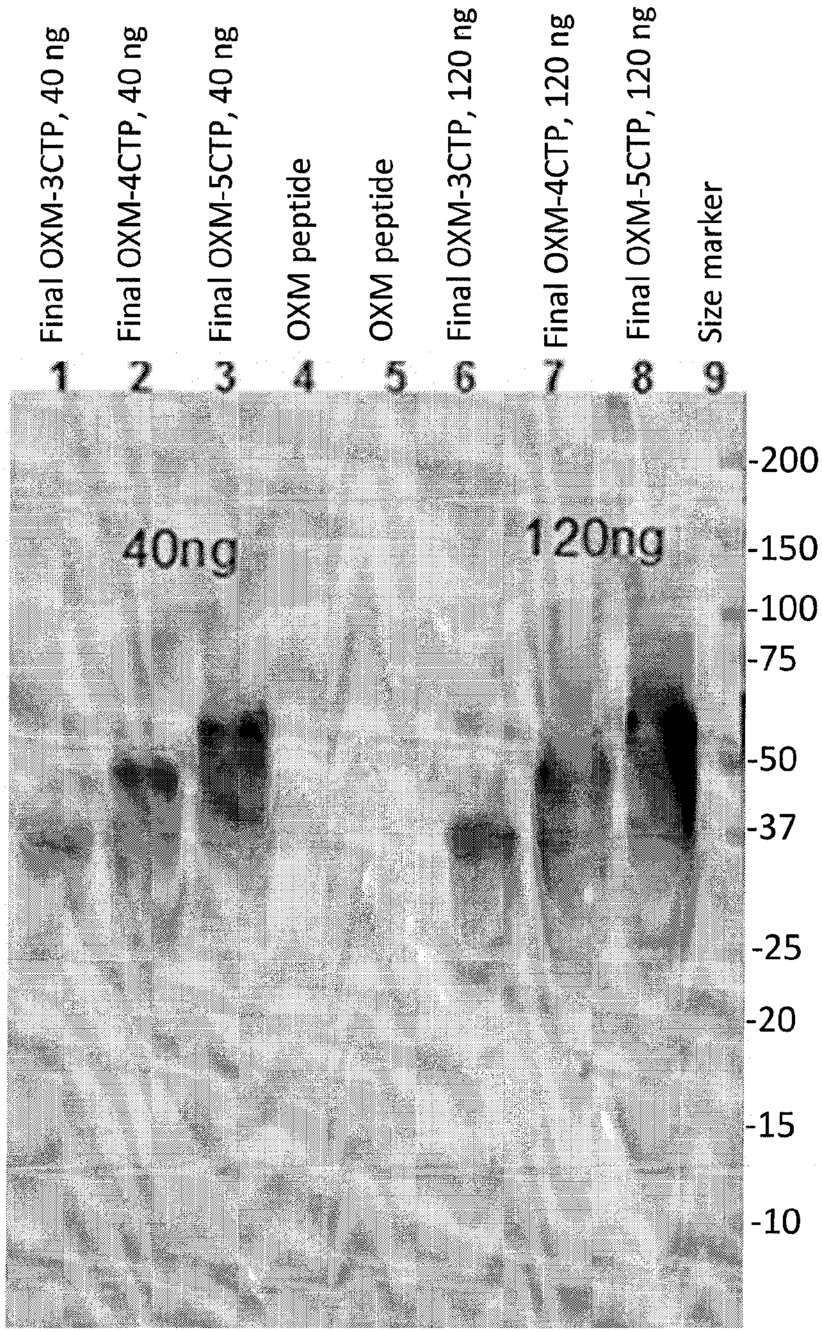
Figure 2:
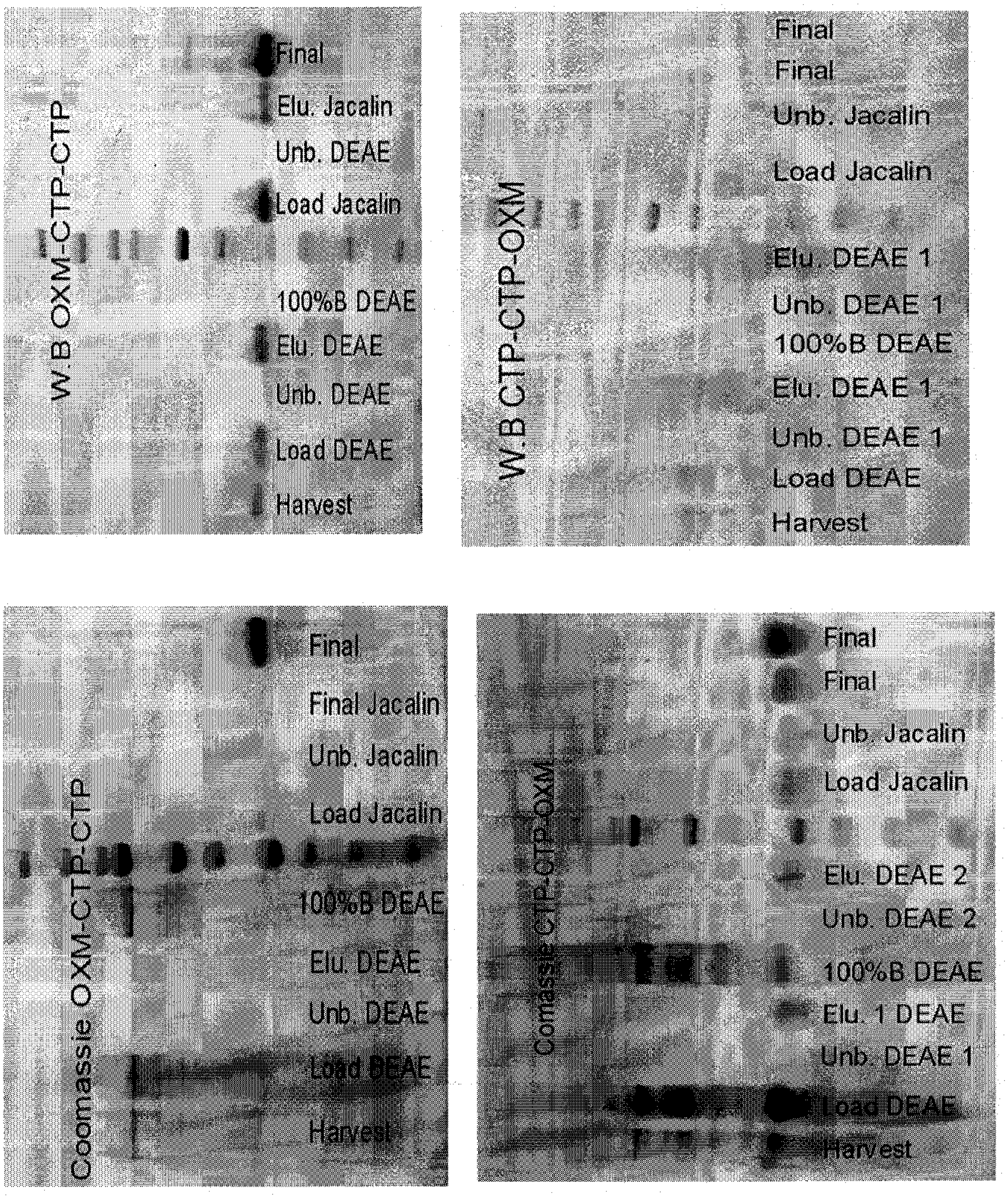
FIG. 2 shows PAGE analysis of samples from purification process of OXM-CTP variants: CTP-OXM-CTP, CTP-OXM-CTP-CTP, OXM-CTP-CTP and CTP-CTP-OXM.

The harvests were purified according to the method described in Materials and Methods. The final samples of variants OXM-CTPX3, OXM-CTPX4 and OXM-CTPX5 were analyzed by SDS-PAGE (Coomassie staining (FIG. 1A) and anti-OXM Western Blot Analysis (FIG. 1B)). For variants CTP-OXM-CTP, CTP-OXM-CTP-CTP, OXM-CTP-CTP and CTP-CTP-OXM, samples from the purification process were analyzed by both Coomassie staining and Western Blot analysis (FIG. 2). As expected, OXM-CTP variants showed differences in size correlating to the number of CTP cassettes fused to the peptide. The relatively high molecular weights are an indication that there may be high occupancy of the O-glycan chains on the potential serine sites on the CTP peptide. The OXM peptide did not react with the anti-OXM antibody, probably due to the technical difficulty in transferring a small sized peptide. The Coomassie staining shows that the OXM-CTP variants were highly purified and contained mainly the high form.

Example 3

Pharmacokinetic (PK) Profile of OXM-CTP Variants

The pharmacokinetic profile of OXM peptide compared to OXM-CTP variants was analyzed in male SD-1 rats.

Figure 3A:
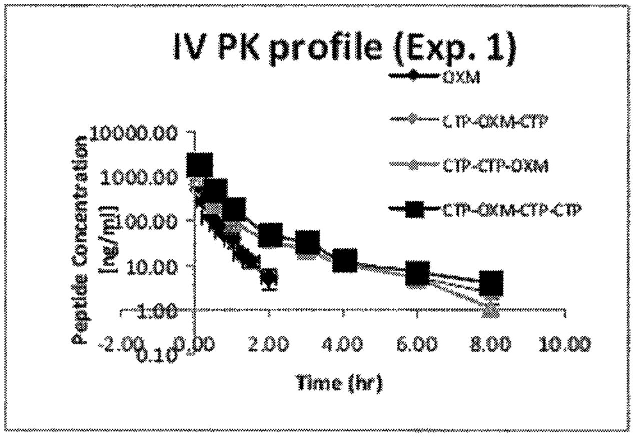
FIG. 3 shows PK profiles of three sequential experiments of OXM peptide and OXM-CTP variants in SD-1 rats.
Figure 3B:
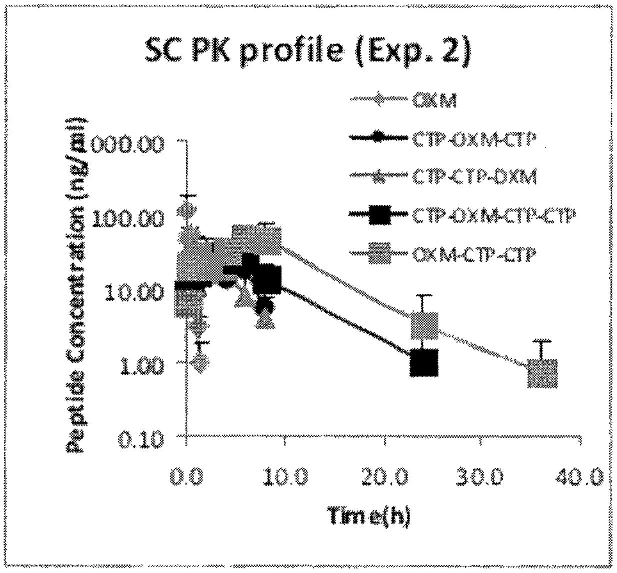
Figure 3C:
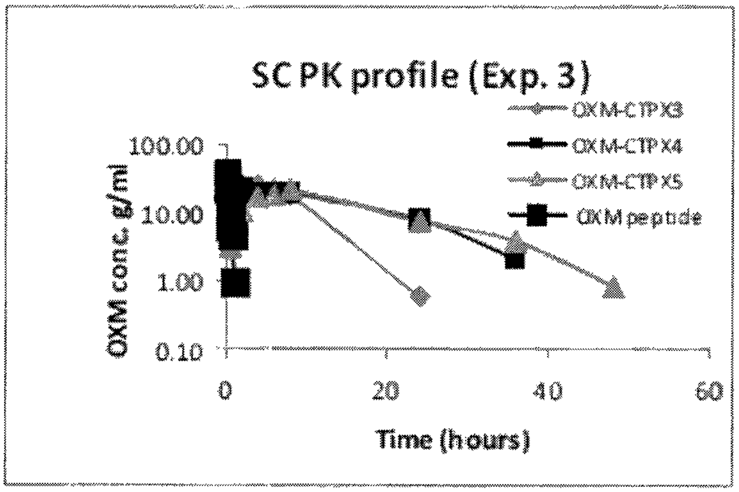

Animals were administered with a single IV (Experiment 1, FIG. 3A) or single SC (Experiments 2&3, FIGS. 3B-3C) injection of native OXM or OXM-CTP variants CTP-OXM-CTP, CTP-OXM-CTP-CTP, OXM-CTP-CTP, CTP-CTP-OXM (230 μg/kg peptide) or variants OXM-CTPX3, OXM-CTPX4 and OXM-CTPX5 (153 μg/kg peptide). Serum concentration of OXM or OXM-CTP variants at the indicated time points was analyzed using commercial ELISA. The PK profile is shown in FIG. 3, and the conventional noncompartmental PK parameters are summarized in Table 4. Addition of CTP peptides to OXM resulted in prolonging the half-life of native OXM, from 0.22 hr to 2.7-10 h for various OXM-CTP variants (Table 4, SC administration; Experiments 2 &3).

Two copies of CTP were added to OXM peptide in three different ways to produce variants CTP-OXM-CTP, OXM-CTP-CTP and CTP-CTP-OXM. The most significant extension of serum half-life was received when the CTPs were added in tandem to the C-terminus of OXM; variant OXM-CTP-CTP with T½ of 4.76 h. Fusion of three CTPs to the OXM C-terminus did not results in an elongated half-life as compared to fusion of two CTPs. Surprisingly, addition of four and five copies of CTPs to OXM c-terminus elongated the T½ up to 10 h (Table 4).

Exposure as reflected by the AUC parameter, was most increased by ~17-fold for variant OXM-CTP-CTP (Experiment 2) and ~30-fold for variants OXM-CTPX4 and OXM-CTPX5 (Experiment 3). These results indicate that there is a superior prolonging effect after the addition of four or five copies of CTP to the OXM peptide.

The bioavailability as calculated from Experiments 1 & 2 was increased for CTP-OXM-CTP-CTP, but no significant improvement was found for CTP-OXM-CTP and CTP-CTP-OXM (Table 4).

TABLE 5

Fold of increase of OXM-CTP variants's PK parameters in compared to OXM peptide as calculated from Experiments 1-3.

| | Variant | T½ Sample/OXM peptide | AUC∞ Sample/OXM peptide |
|---|---|---|---|
| Exp. 1 | CTP-OXM-CTP | NA | 2.8 |
| IV. | CTP-OXM-CTP-CTP | NA | 5.6 |
| | CTP-CTP-OXM | NA | 2.29 |
| Exp. 2 | CTP-OXM-CTP | 14.9 | 3.98 |
| SC. | CTP-OXM-CTP-CTP | 19.9 | 7.48 |
| | OXM-CTP-CTP | 21.6 | 16.3 |
| | CTP-CTP-OXM | 12.4 | 3.03 |
| Exp. 3 | OXM-CTP-CTP-CTP | 21 | 23.45 |
| SC. | OXM-CTP-CTP-CTP-CTP | 56.4 | 32.478 |
| | OXM-CTP-CTP-CTP-CTP-CTP | 53.5 | 33.23 |

Example 4

CTP-Modified OXM Induces Glucose Tolerance

An IPGTT study was carried out in C57BL/6 mice demonstrated that OXM enhanced glucose clearance via stimulation of insulin secretion. The IP glucose tolerance test (IPGTT) evaluates the glucose lowering effect of OXM. In order to evaluate the in vivo activity of OXM or OXM-CTP variants, the IPGTT model was applied. Overnight fasted C57BL/6 mice were injected IP with OXM peptide or OXM-CTP variants followed by IP injection of glucose (1.5 g/kg) and measurement of blood glucose levels from the tail vein by glucometer (FIG. 4). OXM-CTP variants were assessed in two sequential experiments; Experiment 1 for

TABLE 4

Conventional noncompartmental PK parameters of OXM peptide and OXM-CTP variants as were determined in three different experiments.

| | | T½ hr | T½β hr | Cmax ng/ml | Tmax hr | AUC(0-t) ng-hr/ml | AUC∞ ng-hr/ml | CL ml/hr/kg | Vd ml/kg | MRT hr | Bioavailability % |
|---|---|---|---|---|---|---|---|---|---|---|---|
| Exp. 1 | OXM | 0.29 | NA | NA | NA | 211.7 | 213.9 | 993.0 | 417.0 | 0.34 | |
| IV. | CTP-OXM-CTP | 0.25 | 1.57 | NA | NA | 592.7 | 598.0 | 355.3 | 806.9 | 0.81 | |
| | CTP-OXM-CTP-CTP | 0.28 | 1.61 | NA | NA | 968.2 | 977.4 | 217.4 | 506.4 | 0.80 | |
| | CTP-CTP-OXM | 0.27 | 1.20 | NA | NA | 488.6 | 490.4 | 433.3 | 748.1 | 0.86 | |
| Exp. 2 | OXM | 0.22 | | 118.40 | 0.08 | 42.52 | 42.84 | 4960.39 | 1564.40 | 0.37 | 20.09 |
| SC. | CTP-OXM-CTP | 3.28 | | 31.11 | 1.00 | 144.87 | 170.82 | 1243.97 | 5887.75 | 4.73 | 24.44 |
| | CTP-OXM-CTP-CTP | 4.39 | | 30.18 | 6.00 | 313.98 | 320.86 | 662.28 | 4139.25 | 6.62 | 32.43 |
| | OXM-CTP-CTP | 4.76 | | 50.90 | 6.00 | 697.00 | 702.10 | 302.70 | 2078.90 | 8.20 | NA |
| | CTP-CTP-OXM | 2.74 | | 27.77 | 1.00 | 114.15 | 129.85 | 1636.55 | 6459.76 | 4.10 | 23.36 |
| Exp. 3 | OXM | 0.18 | | 36.4 | 0.08 | 13.1 | 13.3 | 16999 | 4375 | | |
| SC. | OXM-CTPX3 | 3.78 | | 25.1 | 2.0 | 308.9 | 312 | 512.8 | 2797 | | |
| | OXM-CTPX4 | 10.15 | | 21.1 | 2.0 | 400.4 | 431.9 | 355.4 | 5379.6 | | |
| | OXM-CTPX5 | 9.63 | | 21.2 | 8 | 431 | 442 | 346.2 | 4812 | | |

Figure 4A:
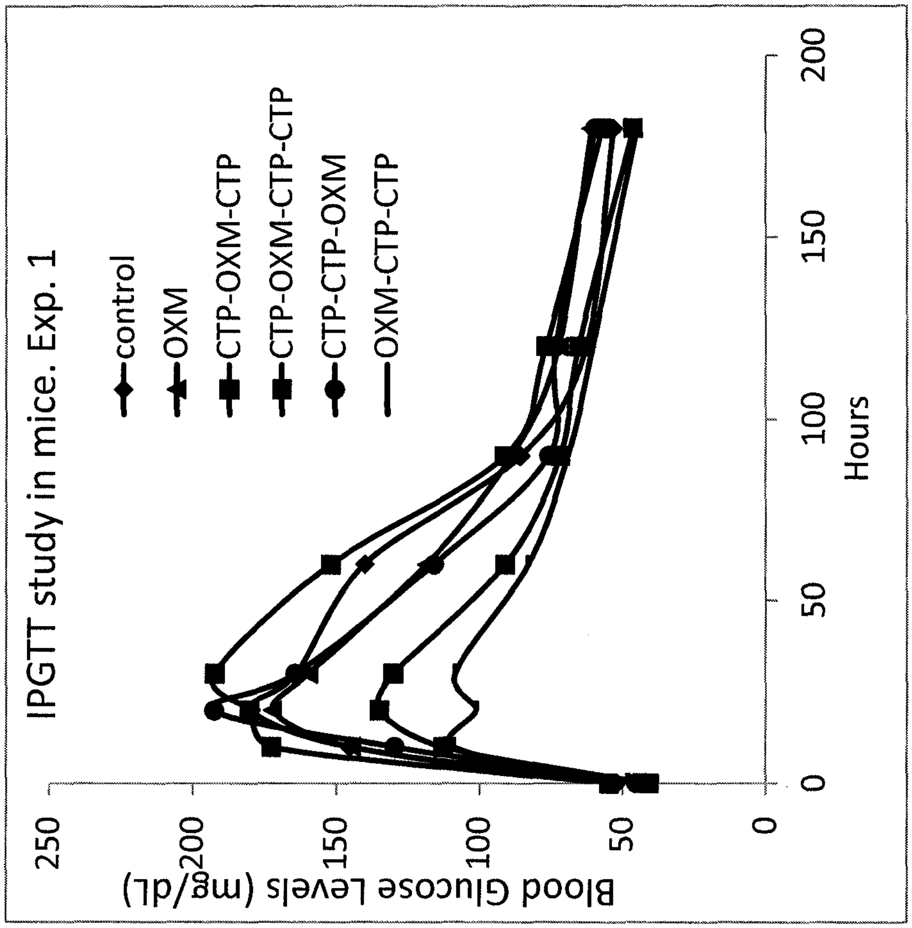
FIG. 4 shows the results of glucose tolerance test of OXM peptide and OXM-CTP variants as measured in C57BL/6 mice.
Figure 4B:
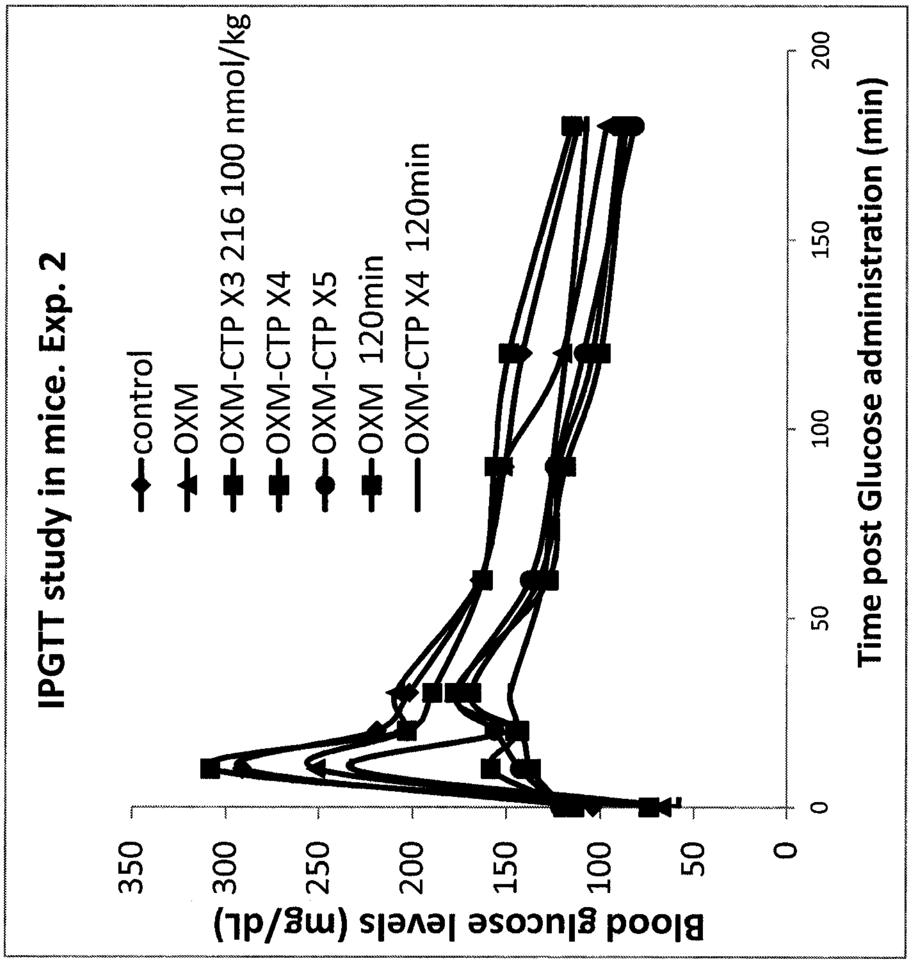
Figure 4D:
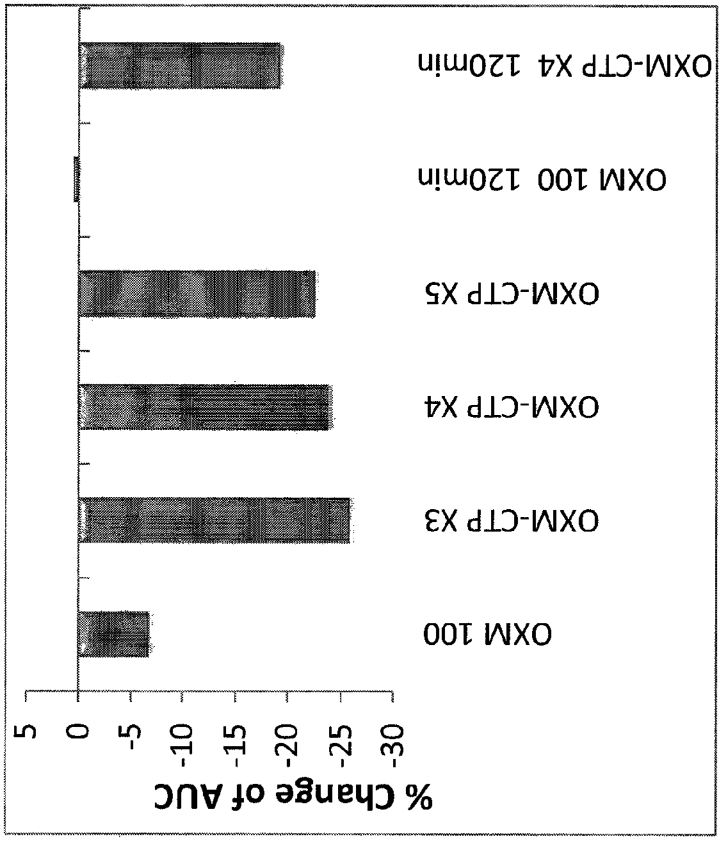
Figure 4C:
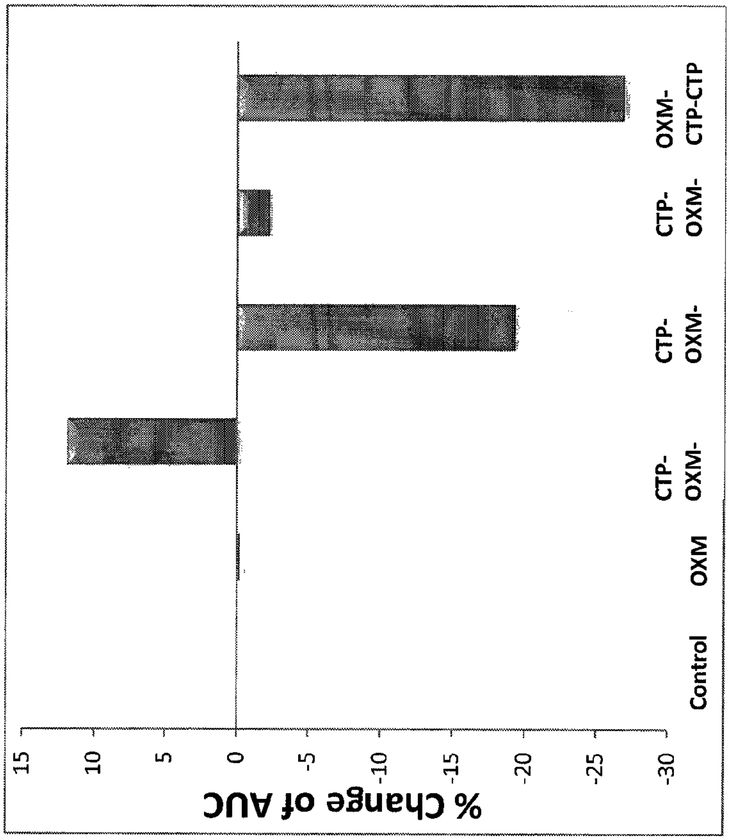
Figure 5A:
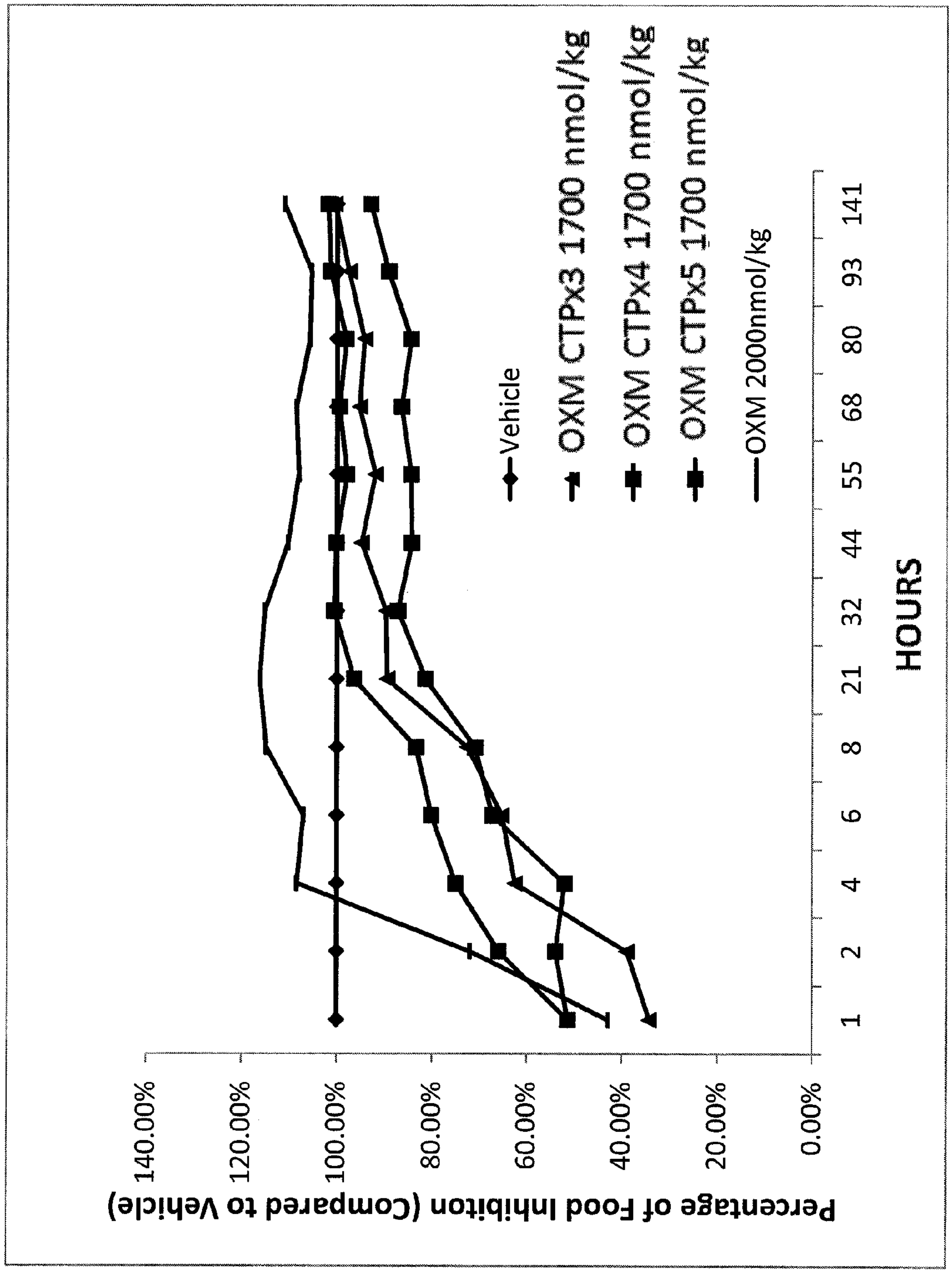
FIG. 5 shows the results of acute food intake of OXM peptide and OXM-CTP variants as measured in C57BL/6 mice. A. The percentage of accumulated food intake in mice receiving treatment compared to vehicle. B. Percentage of food intake for various time intervals over the study.
Figure 5B:
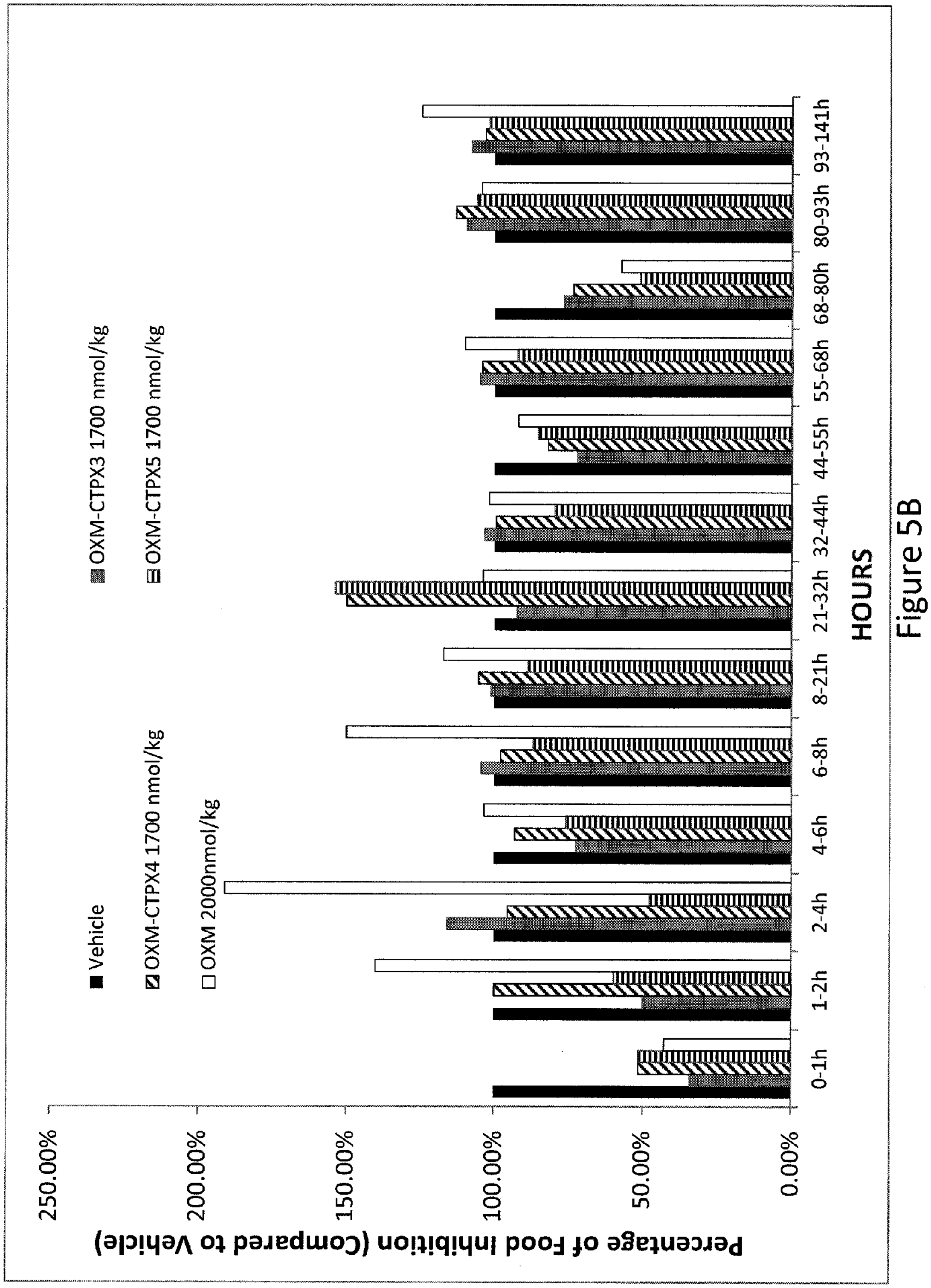

A comparison between the various groups showing the fold increase of T½ and AUC∞ demonstrated that OXM-CTPx4 and OX-CTPx5 were superior in these parameters compared to other variants (Table 5).

variants CTP-OXM-CTP, CTP-OXM-CTP-CTP, OXM-CTP-CTP, CTP-CTP-OXM (FIGS. 4A and 4C) and Experiment 2 for variants OXM-CTP-CTP-CTP, OXM-CTPX4 and OXM-CTPX5 (FIGS. 4B and 4D). OXM (100 nmol/ kg), or OXM-CTP variants (100 nmol/kg) were administered IP 15 min or 2 hrs (OXM peptide and variant OXM-CTPX4) prior to glucose IP injection, and the induction of glucose tolerance was compared to vehicle (buffer) group. A marked effect was measured for OXM-CTP variants CTP-OXM-CTP-CTP, OXM-CTP-CTP, OXM-CTPX3, OXM-CTPX4 and OXM-CTPX5 as reflected by reduction of 20-30% of blood glucose AUC compared to vehicle group as compared to 100 nmol/kg of OXM peptide which had low impact on the calculated AUC (FIG. 4, reduction of 1%, Experiment 1 and 6.7%, Experiment 2). Surprisingly, CTP-OXM-CTP resulted in increased glucose levels while CTP-CTP-OXM had a minor impact on glucose tolerance. OXM-CTPX4 induced glucose tolerance activity even when administered 120 min prior to glucose while OXM peptide activity was no longer apparent. This result is aligned with the improved pharmacokinetics profile of this variant.

Example 5

CTP-Modified OXM Reduce Food Intake

The pharmacological activity of OXM and OXM-CTP variants was further evaluated in C57BL/6 mice following single SC drug administration. In this study, the acute effect on food intake was measured. Male C57BL/6 mice (n=4 per group) were administered with a single SC administration of OXM peptide (2000 nmol/kg) or OXM-CTP (1700 nmol/kg) variants: OXM-CTPX3, OXM-CTPX4 or OXM-CTPX5. Food intake was measured daily for 6 days. OXM and all measured OXM-CTP variants resulted in a significant reduction in food intake, as was measured 1 h and 2 h post injection, 34-51% (compared to vehicle) food intake for OXM and OXM-CTP variant-treated mice, as shown in FIG. 6. The OXM peptide effect was abolished 4 h following injection, while all other OXM-CTP variants were effective for at least 24 h. The most significant effect was found for variant OXM-CTPX5, which reduced food intake for 5 days compared to vehicle. The percentage of food intake compared to vehicle, for various time intervals over the experiment is presented in FIG. 6B. The effect of native OXM disappeared after one hour, OXM-4/5 CTP maintained the inhibition for 2 hours and OXM-5CTP for about 80 hours (3 days). Of note, the superiority of variant OXM-CTPx5 in acute food intake study is in correlation to its improved PK profile. Surprisingly, although variant OXM-CTPx4 demonstrated an improved PK profile with $T_{1/2}$ of about 10 h, its effect did not last as long as OXM-CTPx5 or OXM-CTPx3.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A CTP-modified polypeptide comprising a dual GLP-1/glucagon receptor agonist and one to five chorionic gonadotropin carboxy terminal peptides (CTP) attached to the amino terminus or carboxy terminus of said agonist, wherein said CTP is from the beta-subunit of human chorionic gonadotropin and comprises amino acid positions 1-10 of SEQ ID NO:3.

2. The CTP-modified polypeptide of claim 1, wherein said GLP-1/glucagon receptor agonist is oxyntomodulin.

3. The CTP-modified polypeptide of claim 1, wherein the amino acid sequence of at least one CTP is selected from the group consisting of SEQ ID NO: 1 and SEQ ID NO: 2.

4. The CTP-modified polypeptide of claim 1, wherein at least one CTP is glycosylated or truncated.

5. The CTP-modified polypeptide of claim 1, wherein at least one CTP is attached to said agonist polypeptide via a linker.

6. The CTP-modified polypeptide of claim 5, wherein said linker is a peptide bond.

7. The CTP-modified polypeptide of claim 1, wherein two, three, four or five chorionic gonadotropin carboxy terminal peptides are attached to the carboxy terminus of said agonist.

8. The CTP-modified polypeptide of claim 1, wherein three chorionic gonadotropin carboxy terminal peptides are attached to said agonist, one CTP on the amino terminus and two CTP on the carboxy terminus of said agonist.

9. The CTP-modified polypeptide of claim 1, wherein two chorionic gonadotropin carboxy terminal peptides are attached to said agonist, one CTP on the carboxy terminus and one CTP on the amino terminus of said agonist.

10. The CTP-modified polypeptide of claim 1, wherein two chorionic gonadotropin carboxy terminal peptides are attached to said agonist on the amino terminus of said agonist.

11. The CTP-modified polypeptide of claim 1, wherein said CTP comprises the amino acid sequence set forth in SEQ ID NO: 3.

12. The CTP-modified polypeptide of claim 1, wherein said polypeptide lacks a signal peptide.

13. The CTP-modified polypeptide of claim 1, wherein the amino acid sequence of said CTP-modified polypeptide comprises SEQ ID NO: 9, 15,25, 27,29, amino acids 4-122 of SEQ ID NO: 21, or amino acids 1-119 of SEQ ID NO: 23.

14. The CTP-modified polypeptide of claim 13, wherein said polypeptide is the mature form of said CTP-modified polypeptide and wherein said mature CTP-polypeptide lacks a signal peptide.

15. A pharmaceutical composition comprising the CTP-modified polypeptide of 8.

16. The pharmaceutical composition of claim 15, wherein said GLP 1/glucagon receptor agonist is oxyntomodulin (OXM).

17. A method of producing a CTP-modified polypeptide comprising a dual GLP-1/glucagon receptor agonist and one to five chorionic gonadotropin carboxy terminal peptide (CTP) attached to said agonist, the method comprising the step of attaching one to five chorionic gonadotropin carboxy terminal peptides to the amino terminus or carboxy terminus of said agonist, wherein said CTP is from the beta-subunit of human chorionic gonadotropin and comprises amino acid positions 1-10 of SEQ ID NO:3.

18. The method of claim 17, wherein said GLP-1/glucagon receptor agonist is oxyntomodulin.

19. The method of claim 17, wherein two, three, four, or five chorionic gonadotropin carboxy terminal peptides are attached to the carboxy terminus of said agonist.

20. The method of claim 17, wherein three chorionic gonadotropin carboxy terminal peptides are attached to said agonist, one CTP on the amino terminus and two CTP on the carboxy terminus of said agonist.

21. The method of claim 17, wherein two chorionic gonadotropin carboxy terminal peptides are attached to said agonist, one CTP on the carboxy terminus and one CTP on the amino terminus of said agonist.

22. The method of claim 17, wherein two chorionic gonadotropin carboxy terminal peptides are attached to said agonist on the amino terminus of said agonist.

23. The method of claim 17, wherein the amino acid sequence of said one to five CTP is selected from the group consisting of SEQ ID NO: 1 and SEQ ID NO:2.

24. The method of claim 17, wherein at least one CTP is glycosylated or is truncated.

25. The method of claim 17, wherein at least one CTP is attached to said agonist via a linker.

26. The method of claim 25, wherein said linker is a peptide bond.

27. The method of claim 17, wherein producing said CTP-modified polypeptide extends the biological half-life of said agonist.

28. The method of claim 17, wherein producing said CTP-modified polypeptide improves the area under the curve (AUC) of said agonist.

29. The method of claim 17, wherein producing said CTP-modified polypeptide reduces the dosing frequency of said agonist.

30. The method of claim 17, wherein said CTP comprises the amino acid sequence set forth in SEQ ID NO: 3.

31. The method of claim 17, wherein said CTP-modified polypeptide lacks a signal peptide.

32. The method of claim 17, wherein the amino acid sequence of said CTP-modified polypeptide comprises SEQ ID NO: 9, 15, 25, 27, 29, amino acids 4-122 of SEQ ID NO: 21, or amino acids 1-119 of SEQ ID NO: 23.

33. The method of claim 32, wherein said polypeptide is the mature form of said CTP-modified polypeptide and wherein said mature CTP-polypeptide lacks a signal peptide.

* * * * *

SEQUENCE LISTING

```
<160> NUMBER OF SEQ ID NOS: 30

<210> SEQ ID NO 1
<211> LENGTH: 32
<212> TYPE: PRT
<213> ORGANISM: Homo sapiens

<400> SEQUENCE: 1

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30


<210> SEQ ID NO 2
<211> LENGTH: 28
<212> TYPE: PRT
<213> ORGANISM: Homo sapiens

<400> SEQUENCE: 2

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25


<210> SEQ ID NO 3
<211> LENGTH: 12
<212> TYPE: PRT
<213> ORGANISM: Homo sapiens

<400> SEQUENCE: 3

Ser Ser Ser Ser Lys Ala Pro Pro Pro Ser Leu Pro
1               5                   10


<210> SEQ ID NO 4
```

-continued

<211> LENGTH: 19
<212> TYPE: DNA
<213> ORGANISM: Artificial Sequence
<220> FEATURE:
<223> OTHER INFORMATION: Primer 25

<400> SEQUENCE: 4
ctctagagga catggccac 19

<210> SEQ ID NO 5
<211> LENGTH: 27
<212> TYPE: DNA
<213> ORGANISM: Artificial Sequence
<220> FEATURE:
<223> OTHER INFORMATION: Primer 85R

<400> SEQUENCE: 5
ctggctgtgc tggggcagaa tgggtgt 27

<210> SEQ ID NO 6
<211> LENGTH: 17
<212> TYPE: DNA
<213> ORGANISM: Artificial Sequence
<220> FEATURE:
<223> OTHER INFORMATION: Primer 86

<400> SEQUENCE: 6
ccccagcaca gccaggg 17

<210> SEQ ID NO 7
<211> LENGTH: 18
<212> TYPE: DNA
<213> ORGANISM: Artificial Sequence
<220> FEATURE:
<223> OTHER INFORMATION: Primer 74R

<400> SEQUENCE: 7
gcggccgcat ccagacct 18

<210> SEQ ID NO 8
<211> LENGTH: 391
<212> TYPE: DNA
<213> ORGANISM: Artificial Sequence
<220> FEATURE:
<223> OTHER INFORMATION: CTP-OXM-CTP

<400> SEQUENCE: 8
tctagaggac atggccaccg gcagcaggac cagcctgctg ctggccttcg gcctgctgtg 60
cctgccatgg ctgcaggagg gcagcgccag ctcttcttct aaggctccac ccccatctct 120
gcccagcccc agcagactgc cgggccccag cgacacaccc attctgcccc agcacagcca 180
gggcaccttc accagcgact acagcaagta cctggacagc agaagggccc aggacttcgt 240
ccagtggctg atgaacacca agaggaacag gaacaacatc gcttcctcta gctccaaggc 300
ccctccaccc tctctgccta gcccctctcg gctgcctggc ccatccgaca caccaatcct 360
gccacagtga tgaaggtctg gatgcggccg c 391

<210> SEQ ID NO 9
<211> LENGTH: 119
<212> TYPE: PRT
<213> ORGANISM: Artificial Sequence
<220> FEATURE:
<223> OTHER INFORMATION: CTP-OXM-CTP

<400> SEQUENCE: 9

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Ser Lys Ala
            20                  25                  30

Pro Pro Pro Ser Leu Pro Ser Pro Ser Arg Leu Pro Gly Pro Ser Asp
        35                  40                  45

Thr Pro Ile Leu Pro Gln His Ser Gln Gly Thr Phe Thr Ser Asp Tyr
    50                  55                  60

Ser Lys Tyr Leu Asp Ser Arg Arg Ala Gln Asp Phe Val Gln Trp Leu
65                  70                  75                  80

Met Asn Thr Lys Arg Asn Arg Asn Asn Ile Ala Ser Ser Ser Ser Lys
                85                  90                  95

Ala Pro Pro Pro Ser Leu Pro Ser Pro Ser Arg Leu Pro Gly Pro Ser
            100                 105                 110

Asp Thr Pro Ile Leu Pro Gln
        115
```

<210> SEQ ID NO 10
<211> LENGTH: 19
<212> TYPE: DNA
<213> ORGANISM: Artificial Sequence
<220> FEATURE:
<223> OTHER INFORMATION: Primer 25

<400> SEQUENCE: 10
ctctagagga catggccac 19

<210> SEQ ID NO 11
<211> LENGTH: 29
<212> TYPE: DNA
<213> ORGANISM: Artificial Sequence
<220> FEATURE:
<223> OTHER INFORMATION: Primer 87R

<400> SEQUENCE: 11
gctggagcta gcgatgttgt tcctgttcc 29

<210> SEQ ID NO 12
<211> LENGTH: 26
<212> TYPE: DNA
<213> ORGANISM: Artificial Sequence
<220> FEATURE:
<223> OTHER INFORMATION: Primer 88

<400> SEQUENCE: 12
acatcgctag ctccagcagc aaggcc 26

<210> SEQ ID NO 13
<211> LENGTH: 18
<212> TYPE: DNA
<213> ORGANISM: Artificial Sequence
<220> FEATURE:
<223> OTHER INFORMATION: Primer 74R

<400> SEQUENCE: 13
gcggccgcat ccagacct 18

<210> SEQ ID NO 14
<211> LENGTH: 475
<212> TYPE: DNA
<213> ORGANISM: Artificial Sequence
<220> FEATURE:

<223> OTHER INFORMATION: CTP-OXM-CTP-CTP

<400> SEQUENCE: 14

```
tctagaggac atggccaccg gcagcaggac cagcctgctg ctggccttcg gcctgctgtg     60

cctgccatgg ctgcaggagg gcagcgccag ctcttcttct aaggctccac ccccatctct    120

gcccagcccc agcagactgc cgggccccag cgacacaccc attctgcccc agcacagcca    180

gggcaccttc accagcgact acagcaagta cctggacagc agaagggccc aggacttcgt    240

ccagtggctg atgaacacca agaggaacag gaacaacatc gctagctcca gcagcaaggc    300

cctcccccg agcctgccct ccccaagcag gctgcctggg ccctccgaca caccaatcct    360

gccacagagc agctcctcta aggcccctcc tccatccctg ccatccccct cccggctgcc    420

tggcccctct gacaccccta tcctgcctca gtgatgaagg tctggatgcg gccgc         475
```

<210> SEQ ID NO 15
<211> LENGTH: 147
<212> TYPE: PRT
<213> ORGANISM: Artificial Sequence
<220> FEATURE:
<223> OTHER INFORMATION: CTP-OXM-CTP-CTP

<400> SEQUENCE: 15

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Ser Lys Ala
            20                  25                  30

Pro Pro Pro Ser Leu Pro Ser Pro Ser Arg Leu Pro Gly Pro Ser Asp
        35                  40                  45

Thr Pro Ile Leu Pro Gln His Ser Gln Gly Thr Phe Thr Ser Asp Tyr
    50                  55                  60

Ser Lys Tyr Leu Asp Ser Arg Arg Ala Gln Asp Phe Val Gln Trp Leu
65                  70                  75                  80

Met Asn Thr Lys Arg Asn Arg Asn Asn Ile Ala Ser Ser Ser Ser Lys
                85                  90                  95

Ala Pro Pro Pro Ser Leu Pro Ser Pro Ser Arg Leu Pro Gly Pro Ser
            100                 105                 110

Asp Thr Pro Ile Leu Pro Gln Ser Ser Ser Ser Lys Ala Pro Pro Pro
        115                 120                 125

Ser Leu Pro Ser Pro Ser Arg Leu Pro Gly Pro Ser Asp Thr Pro Ile
    130                 135                 140

Leu Pro Gln
145
```

<210> SEQ ID NO 16
<211> LENGTH: 20
<212> TYPE: DNA
<213> ORGANISM: Artificial Sequence
<220> FEATURE:
<223> OTHER INFORMATION: Primer 75

<400> SEQUENCE: 16

```
ctcccagttc aattacagct                                                 20
```

<210> SEQ ID NO 17
<211> LENGTH: 24
<212> TYPE: DNA
<213> ORGANISM: Artificial Sequence
<220> FEATURE:
<223> OTHER INFORMATION: Primer 89R -continued

<400> SEQUENCE: 17
gctgtgagcg ctgccctcct gcag 24

<210> SEQ ID NO 18
<211> LENGTH: 23
<212> TYPE: DNA
<213> ORGANISM: Artificial Sequence
<220> FEATURE:
<223> OTHER INFORMATION: Primer 90

<400> SEQUENCE: 18
gcgctcacag ccagggcacc ttc 23

<210> SEQ ID NO 19
<211> LENGTH: 18
<212> TYPE: DNA
<213> ORGANISM: Artificial Sequence
<220> FEATURE:
<223> OTHER INFORMATION: Primer 74R

<400> SEQUENCE: 19
gcggccgcat ccagacct 18

<210> SEQ ID NO 20
<211> LENGTH: 391
<212> TYPE: DNA
<213> ORGANISM: Artificial Sequence
<220> FEATURE:
<223> OTHER INFORMATION: OXM-CTP-CTP

<400> SEQUENCE: 20
tctagaggac atggccacag ggagcaggac cagcctgctg ctggctttcg gcctgctgtg 60
tctgccatgg ctgcaggagg gcagcgctca cagccagggc accttcacca gcgactacag 120
caagtacctg gacagcagaa gggcccagga cttcgtccag tggctgatga acaccaagag 180
gaacaggaac aacatcgcta gctccagcag caaggcccct cccccgagcc tgccctcccc 240
aagcaggctg cctgggccct ccgacacacc aatcctgcca cagagcagct cctctaaggc 300
ccctcctcca tccctgccat ccccctcccg gctgcctggc ccctctgaca cccctatcct 360
gcctcagtga tgaaggtctg gatgcggccg c 391

<210> SEQ ID NO 21
<211> LENGTH: 122
<212> TYPE: PRT
<213> ORGANISM: Artificial Sequence
<220> FEATURE:
<223> OTHER INFORMATION: OXM-CTP-CTP

<400> SEQUENCE: 21

Leu Glu Asp Met Ala Thr Gly Ser Arg Thr Ser Leu Leu Leu Ala Phe
1 5 10 15

Gly Leu Leu Cys Leu Pro Trp Leu Gln Glu Gly Ser Ala His Ser Gln
20 25 30

Gly Thr Phe Thr Ser Asp Tyr Ser Lys Tyr Leu Asp Ser Arg Arg Ala
35 40 45

Gln Asp Phe Val Gln Trp Leu Met Asn Thr Lys Arg Asn Arg Asn Asn
50 55 60

Ile Ala Ser Ser Ser Ser Lys Ala Pro Pro Pro Ser Leu Pro Ser Pro
65 70 75 80

Ser Arg Leu Pro Gly Pro Ser Asp Thr Pro Ile Leu Pro Gln Ser Ser

```
                85                  90                  95

Ser Ser Lys Ala Pro Pro Pro Ser Leu Pro Ser Pro Ser Arg Leu Pro
            100                 105                 110

Gly Pro Ser Asp Thr Pro Ile Leu Pro Gln
        115                 120
```

<210> SEQ ID NO 22
<211> LENGTH: 481
<212> TYPE: DNA
<213> ORGANISM: Artificial Sequence
<220> FEATURE:
<223> OTHER INFORMATION: CTPx2-OXM

<400> SEQUENCE: 22

```
ctatagggcg aattgaagga aggccgtcaa ggccgcatga gctctctaga ggacatggcc      60

accggcagca ggaccagcct gctgctggcc ttcggcctgc tgtgcctgcc atggctgcag     120

gagggcagcg ccagctccag cagcaaggcc cctcccccga gcctgccctc cccaagcagg     180

ctgcctgggc cctccgacac accaatcctg ccacagagca gctcctctaa ggcccctcct     240

ccatccctgc catcccctc  ccggctgcct ggcccctctg acacccctat cctgcctcag     300

cacagccagg gcaccttcac cagcgactac agcaagtacc tggacagcag aagggcccag     360

gacttcgtcc agtggctgat gaacaccaag aggaacagga acaacatcgc ttgatgaagg     420

tctggatgcg gccgcggtac cctgggcctc atgggccttc ctttcactgc ccgctttcca     480

g                                                                     481
```

<210> SEQ ID NO 23
<211> LENGTH: 140
<212> TYPE: PRT
<213> ORGANISM: Artificial Sequence
<220> FEATURE:
<223> OTHER INFORMATION: CTPx2-OXM

<400> SEQUENCE: 23

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Ser Lys Ala
            20                  25                  30

Pro Pro Pro Ser Leu Pro Ser Pro Ser Arg Leu Pro Gly Pro Ser Asp
        35                  40                  45

Thr Pro Ile Leu Pro Gln Ser Ser Ser Ser Lys Ala Pro Pro Pro Ser
    50                  55                  60

Leu Pro Ser Pro Ser Arg Leu Pro Gly Pro Ser Asp Thr Pro Ile Leu
65                  70                  75                  80

Pro Gln His Ser Gln Gly Thr Phe Thr Ser Asp Tyr Ser Lys Tyr Leu
                85                  90                  95

Asp Ser Arg Arg Ala Gln Asp Phe Val Gln Trp Leu Met Asn Thr Lys
            100                 105                 110

Arg Asn Arg Asn Asn Ile Ala Arg Ser Gly Cys Gly Arg Gly Thr Leu
        115                 120                 125

Gly Leu Met Gly Leu Pro Phe Thr Ala Arg Phe Pro
    130                 135                 140
```

<210> SEQ ID NO 24
<211> LENGTH: 481
<212> TYPE: DNA
<213> ORGANISM: Artificial Sequence
<220> FEATURE:

<223> OTHER INFORMATION: OXM-CTPx3

<400> SEQUENCE: 24
tctagactcg agcgatcgcc atggccaccg gctctaggac ctccctgctg ctggccttcg 60
gcctgctgtg cctgccctgg ctgcaggaag gcagcgctca ctcccagggc accttcacct 120
ccgactactc caagtacctg gactctcgga gagcccagga cttcgtgcag tggctgatga 180
acaccaagcg gaaccggaac aatatcgcct cctcaagctc caaggcacct ccaccttccc 240
tgcctagccc ttccagactc cctgggccca gtgacacccc tatcctgcct cagtccagct 300
ccagcaaggc cccacccccct agcctgcctt ctccttctcg gctgcctggc cccagcgata 360
ctccaattct gccccagtcc tccagcagta aggctccccc tccatctctg ccatccccca 420
gcagactgcc aggcccttct gatacaccca tcctcccaca gtgatgagga tccgcggccg 480
c 481

<210> SEQ ID NO 25
<211> LENGTH: 147
<212> TYPE: PRT
<213> ORGANISM: Artificial Sequence
<220> FEATURE:
<223> OTHER INFORMATION: OXM-CTPx3

<400> SEQUENCE: 25

Met Ala Thr Gly Ser Arg Thr Ser Leu Leu Leu Ala Phe Gly Leu Leu
1 5 10 15

Cys Leu Pro Trp Leu Gln Glu Gly Ser Ala His Ser Gln Gly Thr Phe
20 25 30

Thr Ser Asp Tyr Ser Lys Tyr Leu Asp Ser Arg Arg Ala Gln Asp Phe
35 40 45

Val Gln Trp Leu Met Asn Thr Lys Arg Asn Arg Asn Asn Ile Ala Ser
50 55 60

Ser Ser Ser Lys Ala Pro Pro Pro Ser Leu Pro Ser Pro Ser Arg Leu
65 70 75 80

Pro Gly Pro Ser Asp Thr Pro Ile Leu Pro Gln Ser Ser Ser Ser Lys
85 90 95

Ala Pro Pro Pro Ser Leu Pro Ser Pro Ser Arg Leu Pro Gly Pro Ser
100 105 110

Asp Thr Pro Ile Leu Pro Gln Ser Ser Ser Ser Lys Ala Pro Pro Pro
115 120 125

Ser Leu Pro Ser Pro Ser Arg Leu Pro Gly Pro Ser Asp Thr Pro Ile
130 135 140

Leu Pro Gln
145

<210> SEQ ID NO 26
<211> LENGTH: 565
<212> TYPE: DNA
<213> ORGANISM: Artificial Sequence
<220> FEATURE:
<223> OTHER INFORMATION: OXM-CTPx4

<400> SEQUENCE: 26
tctagactcg agcgatcgcc atggctaccg gctccagaac ctctctgctg ctggccttcg 60
gcctgctgtg tctgccttgg ctgcaagagg gcagcgctca ttcccagggc accttcacct 120
ccgactactc caagtacctg gactctcgca gagcccagga cttcgtgcag tggctgatga 180
acaccaagcg gaaccggaac aatatcgcct cctccagctc caaggcccct cctccatctc 240

```
tgccatcccc cagtagactg cctgggccct ctgacacccc tatcctgcct cagtccagct    300

cctctaaggc cccaccacct tccctgccta gcccttcaag actgccaggc cctagcgata    360

caccaattct gccccagtcc tccagcagca aggctccccc acctagcctg ccttctccat    420

caaggctgcc tggcccatcc gataccccaa ttttgcctca gagcagctct agcaaggcac    480

ctccccccag tctgccctct ccaagcagac tccctggccc ttcagacact cccattctgc    540

cacagtgatg aggatccgcg gccgc                                          565
```

```
<210> SEQ ID NO 27
<211> LENGTH: 175
<212> TYPE: PRT
<213> ORGANISM: Artificial Sequence
<220> FEATURE:
<223> OTHER INFORMATION: OXM-CTPx4

<400> SEQUENCE: 27

Met Ala Thr Gly Ser Arg Thr Ser Leu Leu Leu Ala Phe Gly Leu Leu
1               5                   10                  15

Cys Leu Pro Trp Leu Gln Glu Gly Ser Ala His Ser Gln Gly Thr Phe
            20                  25                  30

Thr Ser Asp Tyr Ser Lys Tyr Leu Asp Ser Arg Arg Ala Gln Asp Phe
        35                  40                  45

Val Gln Trp Leu Met Asn Thr Lys Arg Asn Arg Asn Asn Ile Ala Ser
    50                  55                  60

Ser Ser Ser Lys Ala Pro Pro Pro Ser Leu Pro Ser Pro Ser Arg Leu
65                  70                  75                  80

Pro Gly Pro Ser Asp Thr Pro Ile Leu Pro Gln Ser Ser Ser Ser Lys
                85                  90                  95

Ala Pro Pro Pro Ser Leu Pro Ser Pro Ser Arg Leu Pro Gly Pro Ser
            100                 105                 110

Asp Thr Pro Ile Leu Pro Gln Ser Ser Ser Ser Lys Ala Pro Pro Pro
        115                 120                 125

Ser Leu Pro Ser Pro Ser Arg Leu Pro Gly Pro Ser Asp Thr Pro Ile
    130                 135                 140

Leu Pro Gln Ser Ser Ser Ser Lys Ala Pro Pro Pro Ser Leu Pro Ser
145                 150                 155                 160

Pro Ser Arg Leu Pro Gly Pro Ser Asp Thr Pro Ile Leu Pro Gln
                165                 170                 175
```

```
<210> SEQ ID NO 28
<211> LENGTH: 650
<212> TYPE: DNA
<213> ORGANISM: Artificial Sequence
<220> FEATURE:
<223> OTHER INFORMATION: OXM-CTPx5

<400> SEQUENCE: 28

ctctagactc gagcgatcgc catggctacc ggctccagaa cctctctgct gctggccttc     60

ggcctgctgt gtctgccttg gctgcaagag ggcagcgctc attcccaggg caccttcacc    120

tccgactact ccaagtacct ggactctcgc agagcacagg acttcgtgca gtggctgatg    180

aacaccaagc ggaaccggaa caatatcgcc tcctccagct ccaaggcccc tcctccatct    240

ctgccatccc ccagtagact gcctgggccc tctgacaccc ctatcctgcc tcagtccagc    300

tcctctaagg ctccaccacc ttccctgcct agcccttcaa gactgccagg ccctagcgat    360

acaccaattc tgccccagtc ctccagcagc aaggctcccc cacctagcct gccttctcca    420
```

```
tcaaggctgc ctggcccatc cgatacccca atttgcctc agagcagctc tagcaaggca    480

cctcccccca gtctgccctc tccaagcaga ctccctggcc cttcagacac tccaatcctc    540

ccacagtcct ctagctctaa agctccacct cccagcctgc ccagccctag tagactcccc    600

ggaccttctg atacccccat cttgccccag tgatgaggat ccgcggccgc               650
```

<210> SEQ ID NO 29
<211> LENGTH: 203
<212> TYPE: PRT
<213> ORGANISM: Artificial Sequence
<220> FEATURE:
<223> OTHER INFORMATION: OXM-CTPx5

<400> SEQUENCE: 29

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala His Ser Gln Gly Thr Phe
            20                  25                  30

Thr Ser Asp Tyr Ser Lys Tyr Leu Asp Ser Arg Arg Ala Gln Asp Phe
        35                  40                  45

Val Gln Trp Leu Met Asn Thr Lys Arg Asn Arg Asn Asn Ile Ala Ser
    50                  55                  60

Ser Ser Ser Lys Ala Pro Pro Pro Ser Leu Pro Ser Pro Ser Arg Leu
65                  70                  75                  80

Pro Gly Pro Ser Asp Thr Pro Ile Leu Pro Gln Ser Ser Ser Ser Lys
                85                  90                  95

Ala Pro Pro Pro Ser Leu Pro Ser Pro Ser Arg Leu Pro Gly Pro Ser
            100                 105                 110

Asp Thr Pro Ile Leu Pro Gln Ser Ser Ser Ser Lys Ala Pro Pro Pro
        115                 120                 125

Ser Leu Pro Ser Pro Ser Arg Leu Pro Gly Pro Ser Asp Thr Pro Ile
    130                 135                 140

Leu Pro Gln Ser Ser Ser Ser Lys Ala Pro Pro Pro Ser Leu Pro Ser
145                 150                 155                 160

Pro Ser Arg Leu Pro Gly Pro Ser Asp Thr Pro Ile Leu Pro Gln Ser
                165                 170                 175

Ser Ser Ser Lys Ala Pro Pro Pro Ser Leu Pro Ser Pro Ser Arg Leu
            180                 185                 190

Pro Gly Pro Ser Asp Thr Pro Ile Leu Pro Gln
        195                 200
```

<210> SEQ ID NO 30
<211> LENGTH: 37
<212> TYPE: PRT
<213> ORGANISM: Homo sapiens

<400> SEQUENCE: 30

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```